(12) United States Patent
Bullerdiek et al.

(10) Patent No.: US 6,544,784 B1
(45) Date of Patent: *Apr. 8, 2003

(54) MULTIPLE-TUMOR ABERRANT GROWTH GENES

(75) Inventors: Jörn Bullerdiek, Bremen (DE); Willem Jan Marie Van de Ven, Leuven (BE); Henricus Franciscus Petrus Maria Schoenmakers, Geldrop (NL); Rafaël Mols, Hallaar (BE)

(73) Assignee: Vlaams Interuniversitair Instituut Voor Biotechnologie VZW (BE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/894,454

(22) PCT Filed: Feb. 19, 1996

(86) PCT No.: PCT/EP96/00716

§ 371 (c)(1),
(2), (4) Date: Sep. 20, 1997

(87) PCT Pub. No.: WO96/25493

PCT Pub. Date: Aug. 22, 1996

(30) Foreign Application Priority Data

Feb. 17, 1995 (EP) ............................................. 95200390
Jul. 14, 1995 (EP) ............................................. 95201951

(51) Int. Cl.[7] ............................................. C12M 5/12
(52) U.S. Cl. .................. 435/325; 435/252.3; 435/69.1; 435/320.1; 536/23.1; 536/23.5
(58) Field of Search ............................... 536/23.1, 23.5; 435/320, 69.1, 320.1, 325, 252.3

(56) References Cited

U.S. PATENT DOCUMENTS 5,389,526 A * 2/1995 Slade et al. ................. 435/69.1
5,756,307 A * 5/1998 Ulil et al. .................... 435/69.1

OTHER PUBLICATIONS

MPSRCH Search Report, US–08–894–454–162–copy1–1–1548. Rni, pp. 2–3, 2000.*
MPSRCH Search Report, US–08–894–454–162–copy 2034–4323–Rni–p. 2, 2000.*
MPSRCH Search Report, pp. 10–11, 2001.*
Sawbrook et al, Molecular Cloning, A Lab. Manual. Cold Spring Harbor Press, Cold Spring Harbor, pp. 10.51–10.53, 1999.*
Watson et al. Recombinant DNA, 2nd Edition. Scientific American Books. 1992.*
Wang et al. Biochem. Mol. Biol. Int., p. 1131–1136, 1994.*
Wang et al. Genbank Accession No. U15158, Oct. 1995.*
Schoenmakers, Eric et al., "Identification, molecular cloning and characterization of the chromosome 12 breakpoint cluster region of uterine leiomyomas", Chemical Abstracts, vol. 122, No. 7, p. 267, Columbus, OH, & Genes, Chromosomes Cancer, vol. 11, No. 2, 1994, pp. 106–118.
Manfioletti, G. et al., "cDNA cloning of the HMGI–C phosphoprotein, a nuclear protein associated with neoplastic and undifferentiated phenotypes", Nucleic Acids Research, vol. 19, No. 24, 1991 pp. 6793–6797, Oxford, GB.
Patel, Umesh A. et al., "Expression and cDNA cloning of human HMGI–C phosphoprotein", Biochemical and Biophysical Research Communications, vol. 201, No. 1, May 30, 1994, pp. 63–70, Orlando, FL.
Derwent Publications, Ltd., London, GB; Database WPI, Section Ch, Week 8735, 87–245773 & JP,A,62 166 897, Jul. 23, 1987.
Chau, Kai–Yin et al., "The gene for the human architectural transcription factor HMGI–C consists of five exons each coding for a distinct functional element", Nucleic Acid Research, vol. 23, No. 21, 1995, pp. 4262–4266.
Van De Ven, Wim J.M. et al., "Molecular characterization of MAR, a multiple aberration region on human chromosome segment 12q13–q15 implicated in various solid tumors", Chemical Abstracts, vol. 123, No. 1, Jul. 3, 1995, p. 721, Columbus, OH, & Genes, Chromosomes Cancer, vol. 12, No. 4, 1995, pp. 296–303.
Schoenmakers, Eric et al., "Recurrent rearrangements in the high mobility group protein gene, HMGI–C, in benign mesenchymal tumors", Chemical Abstracts, vol. 123, No. 15, Oct. 9, 1995, p. 885, Columbus, OH, & Nat. Genet., vol. 10, No. 4, 1995, pp. 436–444.

* cited by examiner

Primary Examiner—Susan Ungar
Assistant Examiner—Munh-Tam Davis
(74) Attorney, Agent, or Firm—Webb Ziesenheim Logsdon Orkin & Hanson, P.C.

(57) ABSTRACT

The present invention relates to the multi-tumor Aberrant Growth (MAG) gene having the nucleotide sequence of any one of the strands of any one of the members of the High Mobility Group protein genes or LIM protein genes, including modified versions thereof. The gene and its derivatives may be used in various diagnostic and therapeutic applications.

4 Claims, 26 Drawing Sheets

| CELL LINE | CHROMOSOME 12 ABERRATION * |
|---|---|
| LI-14/SV40 | t(3;12)(q28;q13-q15) |
| LI-136/SV40 | t(12;14)(q14;q14) |
| LI-166/SV40 | t(12;12)(q14;q23) |
| LI-167/SV40 | t(3;12)(q28;q14-q15) |
| LI-501/SV40 ** | der(12)t(12;16;?)(q14-q15;q22;?) |
| LI-502/SV40 | t(7;13;12)(p15-p21;q14-q21;q13) |
| LI-506/SV40 | Inv(12)(p12q13-q14) |
| LI-538/SV40 | t(3;12)(q28;q13-q15) |
| LM-5.1/SV40 | t(12;14)(q15;q24) |
| LM-30.1/SV40 | t(12;14)(q15;q24) |
| LM-65/SV40 | t(12;14)(q15;q24) |
| LM-67/SV40 | t(12;14)(q14-q15;q24) |
| LM-100/SV40 | t(12;14)(q15;q24) |
| LM-168.1/SV40 | t(X;12)(q22;q15) |
| LM-192.1/SV40 | t(2;3;12)(q35;p21;q14) |
| LM-605/SV40 | Ins(12;11)(q14;q21qter) |
| LM-608/SV40 | t(12;14)(q15;24) |
| LM-609/SV40 | t(12;14)(q15;q24) |
| Ad-211/SV40 | t(8;12)(q21.2-21.3;q13-15) |
| Ad-248/SV40 | Ins(12;6)(q15;q18q21) |
| Ad-263/SV40 | Ins(12)(q15q24.1) |
| Ad-295/SV40 | t(8;12;18)(p12q14;p11.2) |
| Ad-302/SV40 | t(7;12)(q31;q14) |
| Ad-312/SV40 | t(1;12)(p22;q15) |
| Ad-366/SV40 | Inv(12)(p13q15) |
| Ad-366/SV40 | t(12;14)(q13-15;q13-q15) |

\* CYTOGENETIC UPDATE
\*\* FISH ANALYSIS INDICATED A SEGMENT OF THE MAR REGION TO BE PRESENT IN A CYTOGENETICALLY NORMAL CHROMOSOME 3

FIG. 3A

```
                              PRIMER ←┐
          CG  CTT CAG AAG AGA GGA CGC GGC CGC CCC AGG AAG CAG CAG CAA A     45
              L   Q   K   R   G   R   G   R   P   R   K   Q   Q   Q   K
          AA  CCA ACC GGT GAG CCC TCC CCT AAG AGA CCC AGG GGA AGA CCC A     90
              P   T   G   E   P   S   P   K   R   P   R   G   R   P   X
          AA  GGC AGC AAA AAC AAG AGT CCC TCT AAA GCA GCT CAA GAG GAA G    135
              G   S   K   N   K   S   P   S   K   A   A   Q   E   E   A
          CA  GAA GCC ACT GAA GAA AAA CGG CCA AGG GGC AGA CCT AGG AAA T    180
HMG ←────┐   E   A   T   E   E   K   R   P   R   G   R   P   R   K   W
         └LPP
          GG  GGT GGC CAT TCA GGG CAA CTG GGG CCT TCG TCA GTT GCC CCT T    225
              G   G   H   S   G   Q   L   G   P   S   S   V   A   P   S
          CA  TTC CGC CCA GAG GAT GAG CTT GAG CAC CTG ACC AAA AAG ATG C    270
              F   R   P   E   D   E   L   E   H   L   T   K   K   M   L
          TG  TAT GAC ATG GAA AAT CCA CCT GCT GAC GAA TAC TTT GGC GGC T    315
              Y   D   M   E   N   P   P   A   D   E   Y   F   G   G   C
          GT  GCT CGC TGT GGA GAA AAC GTA GTT GGG GAA GGT ACA GGA TGC A    360
              A   R   C   G   E   N   V   V   G   E   G   T   G   C   T
          CT  GCC ATG GAT CAG GTC TTC CAC GTG GAT TGT TTT ACC TGC ATC A    405
              A   M   D   Q   V   F   H   V   D   C   F   T   C   I   I
          TC  TGC AAC AAC AAG CTC CGA GGG CAG CCA TTC TAT GCT GTG GAA A    450
              C   N   N   K   L   R   G   Q   P   F   Y   A   V   E   K
          AG  AAA GCA TAC TGC GAG CCC TGC TAC ATT AAT ACT CTG GAG CAG T    495
              K   A   Y   C   E   P   C   Y   I   N   T   L   E   Q   C
          GC  AAT GTG TGT TCC AAG CCC ATC ATG GAG CGG ATT CTC CGA GCC A    540
              N   V   C   S   K   P   I   M   E   R   I   L   R   A   T
          CC  GGG AAG GCC TAT CAT CCT CAC TGT TTC ACC TGC GTG ATG TGC C    585
              G   K   A   Y   H   P   H   C   F   T   C   V   M   C   H
          AC  CGC AGC CTG GAT GGG ATC CCA TTC ACT GTG GAT GCT GGC GGG C    630
              R   S   L   D   G   I   P   F   T   V   D   A   G   G   L
          TC  ATT CAC TGC ATT GAG GAC TTC CAC AAG AAA TTT GCC CCG CGG T    675
              I   H   C   I   E   D   F   H   K   K   F   A   P   R   C
          GT  TCT GTG TGC AAG GAG CCT ATT ATG CCA GCC CCG GGC CAG GAG G    720
              S   V   C   K   E   P   I   M   P   A   P   G   Q   E   E
          AG  ACT GTC CGT ATT GTG GCT TTG GAT CGA GAT TTC CAT GTT CAC T    765
              T   V   R   I   V   A   L   D   R   D   F   H   V   H   C
          GC  TAC CGA TGC GAG GAT TGC GGT GGT CTC CTG TCT GAA GGA GAT A    810
              Y   R   C   E   D   C   G   G   L   L   S   E   G   D   N
          AC  CAA GGC TGC TAC CCC TTG GAT GGG CAC ATC CTC TGC AAG ACC T    855
              Q   G   C   Y   P   L   D   G   H   I   L   C   K   T   C
          GC  AAC TCT GCC CGC ATC AGC GTG TTG ACC GCC AAG GCG AGC ACT G    900
              N   S   A   R   I   R   V   L   T   A   K   A   S   T   D
          AC  CTT TAG ATT CAG TCA CCT GTT CAG CCG GCA CTG AGA AGA ACG A    945
              L   *   I   Q   S   P   V   Q   P   A   L   R   R   T   N
          AC  ACA AGA AAA AGA TAA GAA ATA CTA GAG TAA AGG CCA TCA AAC T    990
              T   R   K   R   E   I   L   E   *   R   P   S   N   Y
                         └→PRIMER
          AC  GCG AAA AAA AAA AAA AAA AAA AAA GAT GTC GAC GGA TCC TT      1033
              A   K   K   K   K   K   K   K   D   V   D   G   S   *
```

FIG. 4

"GEN3" → partial cDNA sequence

```
GTCACTTTTA TTTGGGGGTG TGGACAGCTG CTTTCCCAGG GGAGTACTTC TTACAGTGGG    60
ATTTCAAGAC AAGATCGGCC TGAAGAAAAA TTATATTTGT ATATTTTTTA AAAAGTGGGA   120
ACTTTGAGGC TCAGAGACAG AGCAGAAGAC AGAACCTGGT CTTCTGATTC CCTGTGTTCT   180
GCTTTTTTCA TTGTTCCACT GGACGCTCAT CAGAGGGAAG ATCTTTTTCC TCAATTGATT   240
CCAACAATGT CTCACCCATC TTGGCTGCCA CCCAAAAGCA CTGGTGAGCC CCTCGGCCAT   300
GTGCCTGCAC GGATGGAGAC CACCCATTCC TTTGGGAACC CCAGCATTTC AGTGTCTACA   360
CAACAGCCAC CCAAAAAGTT TGCCCCGGTA GTTGCTCCAA AACCTAAGTA CAACCCATAC   420
AAACAACCTG GAGGTGAGGG TGATTTTCTT CCACCCCCAC CTCCACCTCT AGATGATTCC   480
AGTGCCCTTC CATCTATCTC TGGAAACTTT CCTCCTCCAC CACCTCTTGA TGAAGAGGCT   540
TTCAAAGTAC AGGGGAATCC CGGAGGCAAG ACACTTGAGG AGAGGCGCTC CAGCCTGGAC   600
GCTGAGATTG ACTCCTTGAC CAGCATCTTG GCTGACCTTG AGTGCAGCTC CCCCTATAAG   660
CCTCGGCCTC CACAGAGCTC CACTGGTTCA ACAGCCTCTC CTCCAGTTTC GACCCCAGTC   720
ACAGGACACA AGAGAATGGT CATCCCGAAC CAACCCCCTC TAACAGCAAC CAAGAAGTCT   780
ACATTGAAAC CACAGCCTGC ACCCCAGGCT GGACCCATCC CTGTGGCTCC AATCGGAACA   840
CTCAAACCCC AGCCTCAGCC AGTCCCAGCC TCCTACACCA CGGCCTCCAC TTCTTCAAGG   900
CCTACCTTTA ATGTGCAGGT GAAGTCAGCC CAGCCCAGCC CTCATTATAT GGCTGCCCCT   960
TCATCAGGAC AAATTTATGG CTCAGGGCCC CAGGGCTATA CACTCAGCC AGTTCCTGTC   1020
TCTGGGCAGT GTCCACCTCC TTCAACACGG GGAGGCATGG ATTATGCCTA CATTCCACCA  1080
CCAGGACTTC AGCCGGAGCC TGGGTATGGG TATGCCCCCA ACCAGGGACG CTATTATGAA  1140
GGCTACTATG CAGCAGGGCC AGGCTATGGG GGCAGAAATG ACTCTGACCC TACCTATGGT  1200
CAACAAGGTC ACCCAAATAC CTGGAAACGG GAACCAGGGT ACACTCCTCC TGGAGCAGGG  1260
AACCAGAACC CTCCTGGGAT GTATCCAGTC ACTGGTCCCA AGAAGACCTA TATCACAGAT  1320
CCTGTTTCAG CCCCCTGTGC GCCACCATTG CAGCCAAAGG GTGGCCATTC AGGGCAACTG  1380
GGGCCTTCGT CAGTTGCCCC TTCATTCCGC CCAGAGGATG AGCTTGAGCA CCTGACCAAA  1440
AACATGCTGT ATGACATGGA AAATCCACCT GCTGACGAAT ACTTTGGCCG CTGTGCTCGC  1500
TGTGCAGAAA ACGTAGTTGG GGAAGGTACA GGATGCACTG CCATGGATCA GGTCTTCCAC  1560
GTGGATTGTT TTACCTGCAT CATCTGCAAC AACAAGCTCC GAGGGCAGCC ATTCTATGCT  1620
```

FIG.5A

```
GTGGAAAAGA AAGCATACTG CGAGCCCTGC TACATTAATA CTCTGGAGCA GTGCAATGTG  1680
TGTTCCAAGC CCATCATGGA GCGGATTCTC CGAGCCACCG GGAAGGCCTA TCATCCTCAC  1740
TGTTTCACCT GCGTGATGTG CCACCGCAGC CTGGATGGGA TCCCATTCAC TGTGGATGCT  1800
GGCGGGCTCA TTCACTGCAT TGAGGACTTC CACAAGAAAT TTGCCCCGCG GTGTTCTGTG  1860
TGCAAGGAGC CTATTATGCC AGCCCCGGGC CAGGAGGAGA CTGTCCGTAT TGTGGCTTTG  1920
GATCGAGATT CCATGTTCA CTGCTACCGA TGCGAGGATT GCGGTGGTCT CCTGTCTGAA  1980
GGAGATAACC AAGGCTGCTA CCCCTTGGAT GGGCACATCC TCTGCAAGAC CTGCAACTCT  2040
GCCCGCATCA GGGTGTTCAC CGCCAAGGCG AGCACTGACC TTTAGATTCA GTCACCTGTT  2100
CAGCCGGCAC TGAGAAGAAC GAACACAAGA AAAGATAAG AAATACTAGA GTAAAGGCCA  2160
TCAAACTACG CGATAGTCTC TGTTCTTCAT CTGCTATTAA CCTTGCCTTA GAAACACATA  2220
AATTATGAGA TTTTTTTTTA AAAGTTGTTA CCAAATACAC ATTTCACATT GAATCATGTA  2280
GGATCTTGAT GGGCCTTTGT TCCCAAGGAC TTCCACATTT TTGCACAGAT TATGCTCCAT  2340
CCCTTCACTT CTGCATTCCT GTAACTTTTA ATCCCTATGT TTGTCTCACT TTTCATCTGG  2400
TTGAATGGCT TTTCTTAGTG TGGTATTTGC TGTCACATAG TTTTTTCCTG GGTGAGTCTG  2460
CCAACTCACA GGTGCTTTTA GGCTTGAAAT CTCCATCCTA TCATTTCCGT TTTGCCTGTG  2520
ACTGTAAAGA GTAGCCATTC TTTTCCCATG TATTGAAGAG GATATTCTTC TCTTGCTTTA  2580
TACTACTCAC GTCCTTGGGG AGGGAAATGC ACAATTTTTT TTTGTTAGCG TGTAAAGAAT  2640
TTAAGCTGTA AATTACATAA GTTAGAACAA GCCCAAATTT AATTTGCAAC CATCAGAATT  2700
CAGAATCTAT AGTGACCAGT GATCAAGGCT AATTGGAAAA GAGTTATCGG CCCATAGCTA  2760
ATAAGTAGTG ACAGACAACC AAGCTTCAAT ATTTTTCTAA AGAAATTACA GGTGGGATAT  2820
GCTAGAAAAG GCATTTTGGG GTTATGTTTA AAAAAACATT ATTGTCCCAC AATATTACCT  2880
TAAGATTTTT CTTTTCCGCA CTACCTGAAC ATTGTAATAC AGACAAACTT GATTTCTTCT  2940
AGAAGATAAC ATTTTCAATA CTGTCCCACT TCTCATCTTA AAAATATTGT CATGTTTATT  3000
CTAATATCCA ACGCAACTAT CAAAATTGCC TTTTTCTCTA GAGGATGAAG GCTGTGAAAA  3060
AACCGTTCAA ATTCTCTTCT TTTTCTTTTT TATTACCAGG TCCATTTTGC CTGACAATTG  3120
CAAATCAGAG CATACAAAAT AAAACTGTGC AGTTTTGTTT GGTTTACTTT CAAAAGAGTA  3180
GAAAGCTTGA AAAGATTCTG AAACCACAGT TTCATTATTC TCATAATCCT TCTGCAACTG  3240
AAATTACATA TTGCAGGAGA CATTTTCATA TCATCAATGT GACATTTACA CCACACTTTC  3300
AAAGACAATC ACTGAAACAA AAATTGTCTT TATGAGCTAA AAATATGCAG AATCTCTGCC  3360
```

*FIG.5B*

```
TAGAATCTTT ATTCAAACTT TTATTAGCCA GTGAAACACT TGCTTGCCAA CTGCCAAGCC    3420
ATACTTATTA AGTTCGAACA TGTTTCACTT AAGGAGAGAC ACCTAGCTTA GTCATGGCAA    3480
GTTGCCATTT TGTAAACTAA GGATTTTGGA CTGAGATTTC TTAAATCTTT CTTCAAATCT    3540
CCCACAAGTA TATACTTTTA AATTATGGAG TATTTTAAGT CTACAAAAAG GTATAAATAA    3600
TAATATAATG AATTCCTATA TACCTAATAC CCAGTTTAAG ACACCAAATA TAACAAGTAT    3660
AATTACATCC TCCAATGTAC CGTTTCCTTA TTCCACAGAT ATCTTTTTCA TTATTGTGAA    3720
GTGATGTTCA GATTTCTAGT TTTTTTTTCT AGTTTTTAAT TTAACATCA GAACTGAAAT     3780
AAAAAATTAT GGATACGTGT TTTGAATTGC AAACTATTCC TCAGGAATTC CAATTAAATT    3840
TATTTTACTT GAATAGGAAT GATCATAAAA GTGATTCTTT TTTTGTGACT AGAAATTCTT    3900
AAGCCGATGG TCACTATAGC TCATCCTTAA TGTATGGCTC ATTTGCTTTT GTCACTAAAC    3960
GGTTTTGTGT TAGAACCACC AAAATTATAG CTTTTAAGAG CTTCCTTTGA CCACTGTCTT    4020
TTTCTTACCC TACTTCTCTT ATCTTTGATC GTATATTTCT CATAATGTGA AATATGATGA    4080
GATTCACTTA GGGGCAGCAT GTTAGTTTTG CGAGGCAATG TCAACTGTGT CTCTGAATTC    4140
CTGTCTTCCA AATTGAAGCC AGACCATGCT GATGACCTCA AGTAGCACTG ACTATTTGAC    4200
AATAGGGCTG ATAATGTAAT CGGCTTGAAT TTTGACTTAG TAACTTTTTA TGTAATACTT    4260
TCGGAGAAAT TCTCTTTAGG ACAAAGCAGA GAGTCCAATT TATTGAGGGA TAGATTGTAT    4320
CTC                                                                 4323
```

*FIG.5C*

MSHPSWLPPKSTGEPLGHVPARMETTHSFGNPSISVSTQQPPKKFAPVVAPKPKY
NPYKQPGGEGDFLPPPPPPLDDSSALPSISGNFPPPPPLDEEAFKVQGNPGGKTL
EERRSSLDAEIDSLTSILADLECSSPYKPRPPQSSTGSTASPPVSTPVTGHKRMV
IPNQPPLTATKKSTLKPQPAPQAGPIPVAPIGTLKPQPQPVPASYTTASTSSRPT
FNVQVKSAQPSPHYMAAPSSGQIYGSGPQGYNTQPVPVSGQCPPPSTRGGMDYAY
IPPPGLQPEPGYGYAPNQGRYYEGYYAAGPGYGGRNDSDPTYGQQGHPNTWKREP
GYTPPGAGNQNPPGMYPVTGPKKTYITDPVSAPCAPPLQPKGGHSGQLGPSSVAP
SFRPEDELEHLTKKMLYDMENPPADEYFGRCARCGENVVGEGTGCTAMDQVFHVD
  LIM 1
CFTCIICNNKLRGQPFYAVEKKAYCEPCYINTLEQCNVCSKPIMERILRATGKAY
  LIM 2
HPHCFTCVMCHRSLDGIPFTVDAGGLIHCIEDFHKKFAPRCSVCKEPIMPAPGQE
  LIM 3
ETVRIVALDRDFHVHCYRCEDCGGLLSEGDNQGCYPLDGHILCKTCNSARIRVLT
AKASTDL*

```
3721 acagtaagaa catcataaaa tttttatata tatagtttat ttttgtggga gataaatttt
3781 ataggactgt totttgctgt tgttggtcgc agctacataa gactggacat ttaactttc
3841 taccatttct gcaagttagg tatgtttgca ggagaaaagt atcaagacgt ttaactgcag
3901 ttgactttct ccctgttcct ttgagtgtct tctaacttta ttctttgttc tttatgtaga
3961 attgctgtct atgattgtac tttgaatcgc ttgcttgttg aaaatattto tctagtgtat
4021 tatcactgtc tgttctgcac aataaacata acagcctctg tgatccc
```

*FIG. 7B*

*FIG.10A*
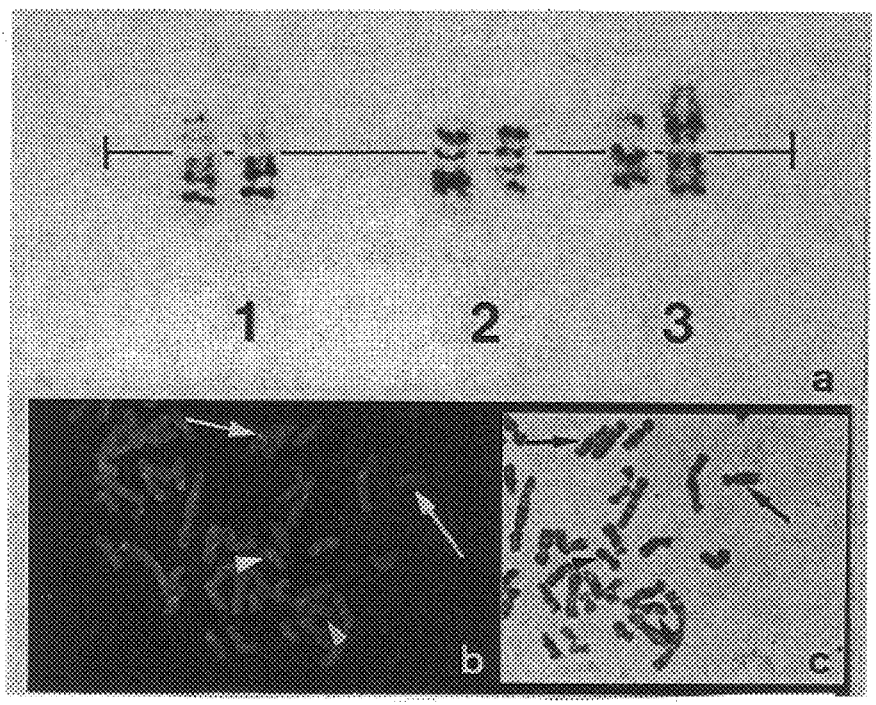
*FIG.10B*  *FIG.10C*
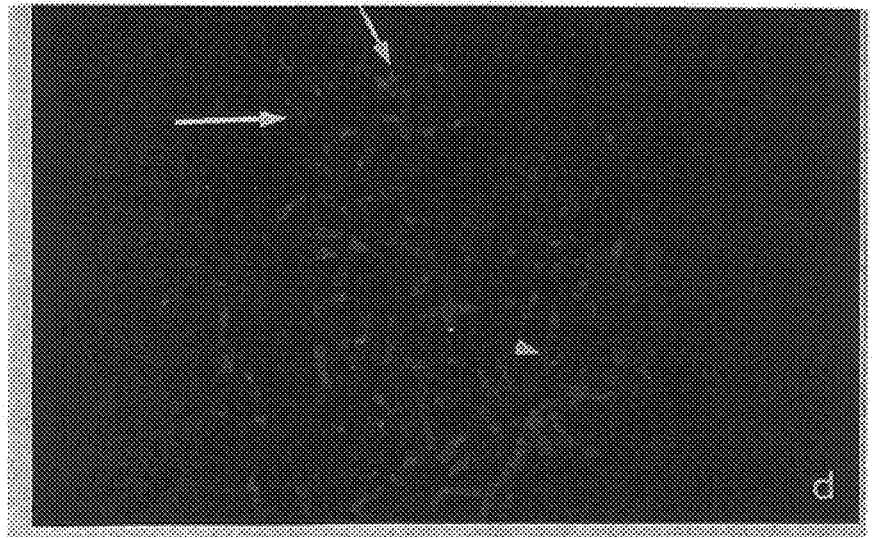
*FIG.10D*

MULTIPLE-TUMOR ABERRANT GROWTH GENES

This application is a 371 of International Patent Application No. PCT/EP96/00716, filed Feb. 19, 1996, which claims priority from application EPO 9521951.1, Jul. 14, 1995 and application EPO 95200390.3, filed Feb. 17, 1995.

The present invention relates to the identification of the High Mobility Group (HMG) protein gene family as a family of genes frequently associated with aberrant cell growth as found in a variety of both benign and malignant tumors. The invention in particular relates to the identification of a member of the HMG gene family as the broadly acting chromosome 12 breakpoint region gene involved in a number of tumors, including but not limited to the mesenchymal tumors hamartomas (e.g. breast and lung), lipomas, pleomorphic salivary gland adenomas, uterine leiomyomas, angiomyxomas, fibroadenomas of the breast, polyps of the endometrium, atherosclerotic plaques, and other benign tumors as well as various malignant tumors, including but not limited to sarcomas (e.g. rhabdomyosarcoma, osteosarcoma) and carcinomas (e.g. of breast, lung, skin, thyroid), as well as leukemias and lymphomas. The invention also relates to another member of the HMG gene family that was found to be implicated in breaks in chromosome 6.

Furthermore, the invention concerns the identification of members of the LIM protein family as another type of tumor-type specific breakpoint region genes and frequent fusion partners of the HMG genes in these tumors. The LPP (Lipoma-Preferred Partner) gene of this family is found to be specific for lipomas. The invention relates in particular to the use of the members of the HMG and LIM gene family and their derivatives in diagnosis and therapy.

Multiple independent cytogenetic studies have firmly implicated region q13-q15 of chromosome 12 in a variety of benign and malignant solid tumor types. Among benign solid tumors, involvement of 12q13-q15 is frequently observed in benign adipose tissue tumors [1], uterine leiomyomas [2, 3], and pleomorphic adenomas of the salivary glands [4, 5]. Involvement of the same region has also been reported for endometrial polyps [6, 7] for hemangiopericytoma [8], and for chondromatous tumors [9, 10, 11, 12]. Recently, the involvement of chromosome 12q13-q15 was reported in pulmonary chondroid hamartoma [13, 14]. Finally, several case reports of solid tumors with involvement of chromosome region 12q13-q15 have been published; e.g. tumors of the breast [15, 16), diffuse astrocytomas [17], and a giant-cell tumor of the bone [18]. Malignant tumor types with recurrent aberrations in 12q13-q15 include myxoid liposarcoma [19], soft tissue clear-cell sarcoma [20, 21, 22], and a subgroup of rhabdomyosarcoma [23].

Although these studies indicated that the same cytogenetic region of chromosome 12 is often involved in chromosome aberrations, like translocations, in these solid tumors, the precise nature of the chromosome 12 breakpoints in the various tumors is still not known. Neither was it established which genes are affected directly by the translocations.

In previous physical mapping studies [39], the chromosome 12q breakpoints in lipoma, pleomorphic salivary gland adenoma, and uterine leiomyoma were mapped between locus D12S8 and the CHOP gene and it was shown that D12S8 is located distal to CHOP. Recently, it was also found by FISH analysis that the chromosome 12q breakpoints in a hamartoma of the breast, an angiomyxoma and multiple pulmonary chondroid hamartomas are mapping within this DNA interval. In an effort to molecularly clone the genes affected by the chromosome 12q13-q15 aberrations in the various tumors, the present inventors chose directional chromosome walking as a structural approach to define the DNA region encompassing these breakpoints.

As a starting point for chromosome walking, locus D12S8 was used. During these walking studies, it was shown that the chromosomal breakpoints as present in a number of uterine leiomyoma-derived cell lines are clustered within a 445 kb chromosomal segment which has been designated Uterine Leiomyoma Cluster Region on chromosome 12 (ULCR12) [24]. Subsequently, it was found that a 1.7 Mb region on chromosome 12 encompasses the chromosome 12 breakpoints of uterine leiomyoma-, lipoma-, and salivary gland adenoma-cells, with the breakpoint cluster regions of the various tumor types overlapping [25, "ANNEX 1"]. This 1.7 Mb region on the long arm of chromosome 12, which contains ULCR12 obviously, was designated Multiple Aberration Region (MAR) to reflect this feature. In a regional fine mapping study, MAR was recently assigned to 12q15.

It has thus been found that essentially all breakpoints of chromosome 12 map in a 1.7 Mb region indicated herein as the "Multiple Aberration Region" or MAR. Further research revealed that in this region a member of the High Mobility Group gene family, the HMGI-C gene, can be identified as a postulated multi-tumor aberrant growth gene (MAG). The same applies to members of the LIM family which are also found to be involved in chromosome aberrations. Of these the chromosome 3-derived Lipoma-Preferred Partner (LPP) gene is particularly implicated in lipomas.

LIM proteins are proteins carrying cystein-rich zinc-binding domains, so-called LIM domains. They are involved in protein-protein interactions [for a review see ref. 80]. One of the members of the protein family is the now disclosed LPP protein mapping at chromosome 3.

According to the present invention the aberrations in the HMGI-C gene on chromosome 12 and the LPP gene on chromosome 3 have been used as a model to reveal the more general concept of the involvement of members of the HMG and LIM gene families in both benign and malignant tumors. To demonstrate that there exists a more general concept of gene families, which, when affected by chromosome rearrangements, lead to a particular group of tumor growth, the present inventors demonstrated that the HMGI(Y) gene, which is a member of the HMG family, is involved in breaks in chromosome 6.

Although both the HMG and LIM gene families are known per se, up till the present invention the correlation between these families and tumor inducing chromosome aberrations, like translocations, deletions, insertions and inversions, has not been anticipated. Furthermore, until now it was not previously demonstrated that alterations in the physiological expression level of the members of the gene family are probably also implicated in tumor development. According to the invention it was demonstrated that in normal adult cells the expression level of the HMGI-C gene is practically undetectable, whereas in aberrantly growing cells the expression level is significantly increased.

SUMMARY OF THE INVENTION

Based on these insights the present invention now provides for the members of the gene families or derivatives thereof in isolated form and their use in diagnostic and therapeutic applications. Furthermore the knowledge on the location and nucleotide sequence of the genes may be used to study their rearrangements or expression and to identify a possible increase or decrease in their expression level and the effects thereof on cell growth. Based on this information diagnostic tests or therapeutic treatments may be designed.

BRIEF DESCRIPTION OF THE DRAWINGS

FIG. 4 is a sequence of 3'-RACE product comprising the junction between part of the HMGI-C gene and part of the LPP gene;

FIG. 5 is a partial cDNA sequence of the LPP gene;

FIG. 6 is an amino acid sequence of the LPP gene;

Figure 7A:
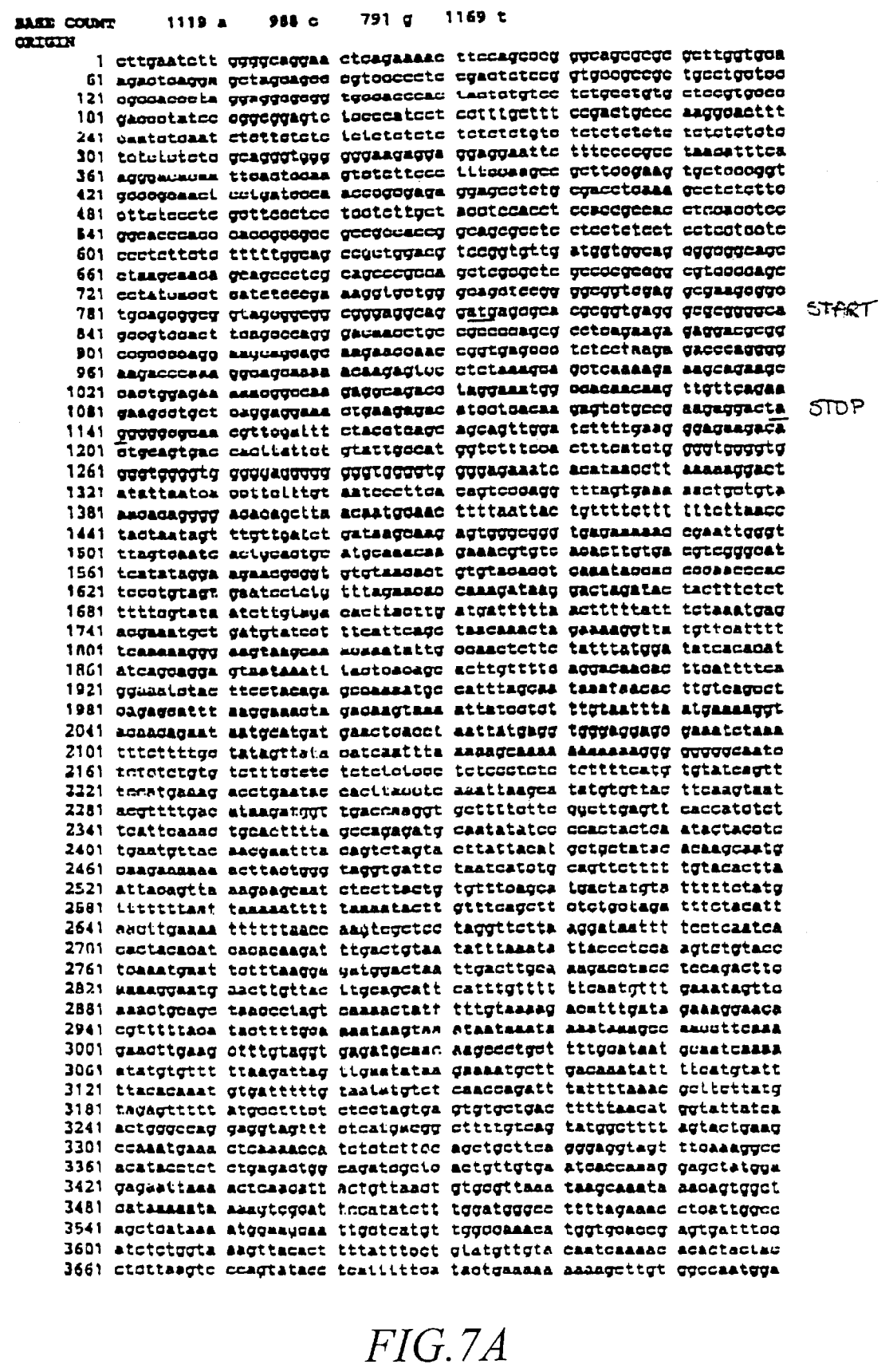

FIG. 7 is a nucleotide sequence of HMGI-C (U28749); and

FIG. 10 is a schematic representation of a partial karyotype of Ad-295/SV40, and depiction of FISH analysis of metaphase chromosomes of Ad-295/SV40 cells;

DETAILED DESCRIPTION OF THE PREFERRED EMBODIMENTS

Figure 1A:
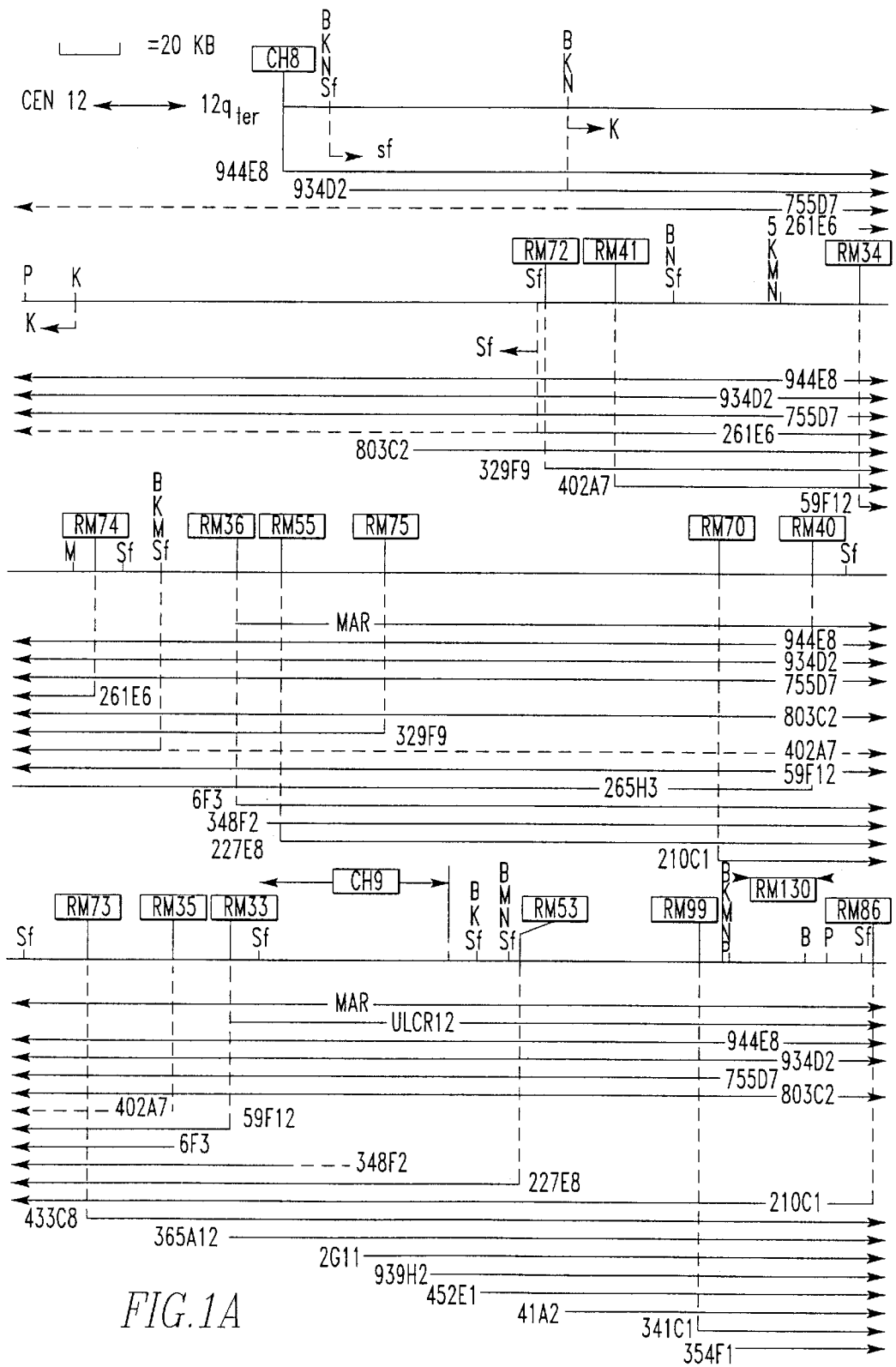
FIG. 1 is a long range physical map of a 6 Mb region on the long arm of human chromosome 12 deduced from a YAC contig consisting of 75 overlapping CEPH YAC clones and spanning the chromosome 12q breakpoints present in a variety of benign solid tumors.
Figure 1B:
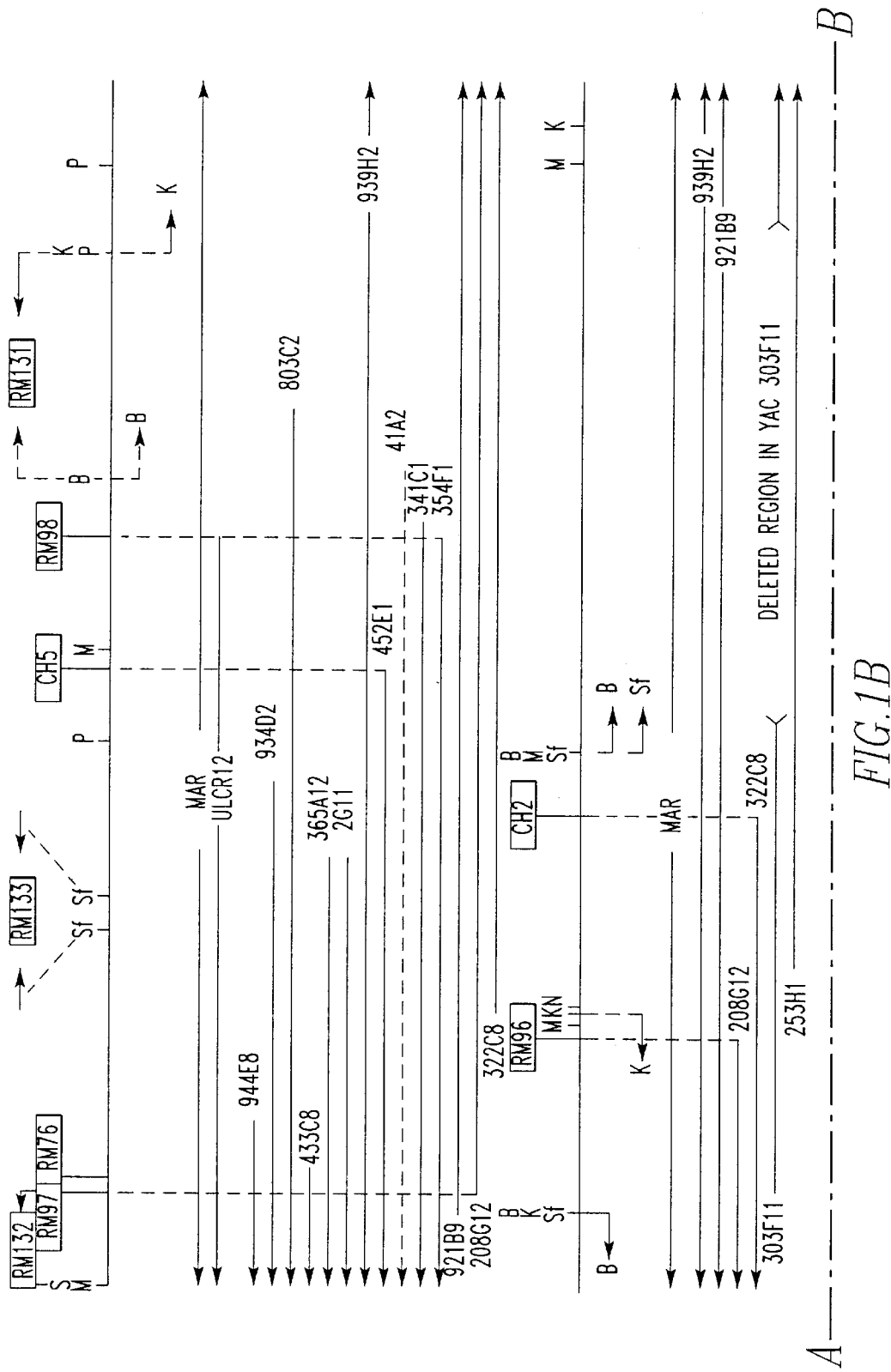
Figure 1B:
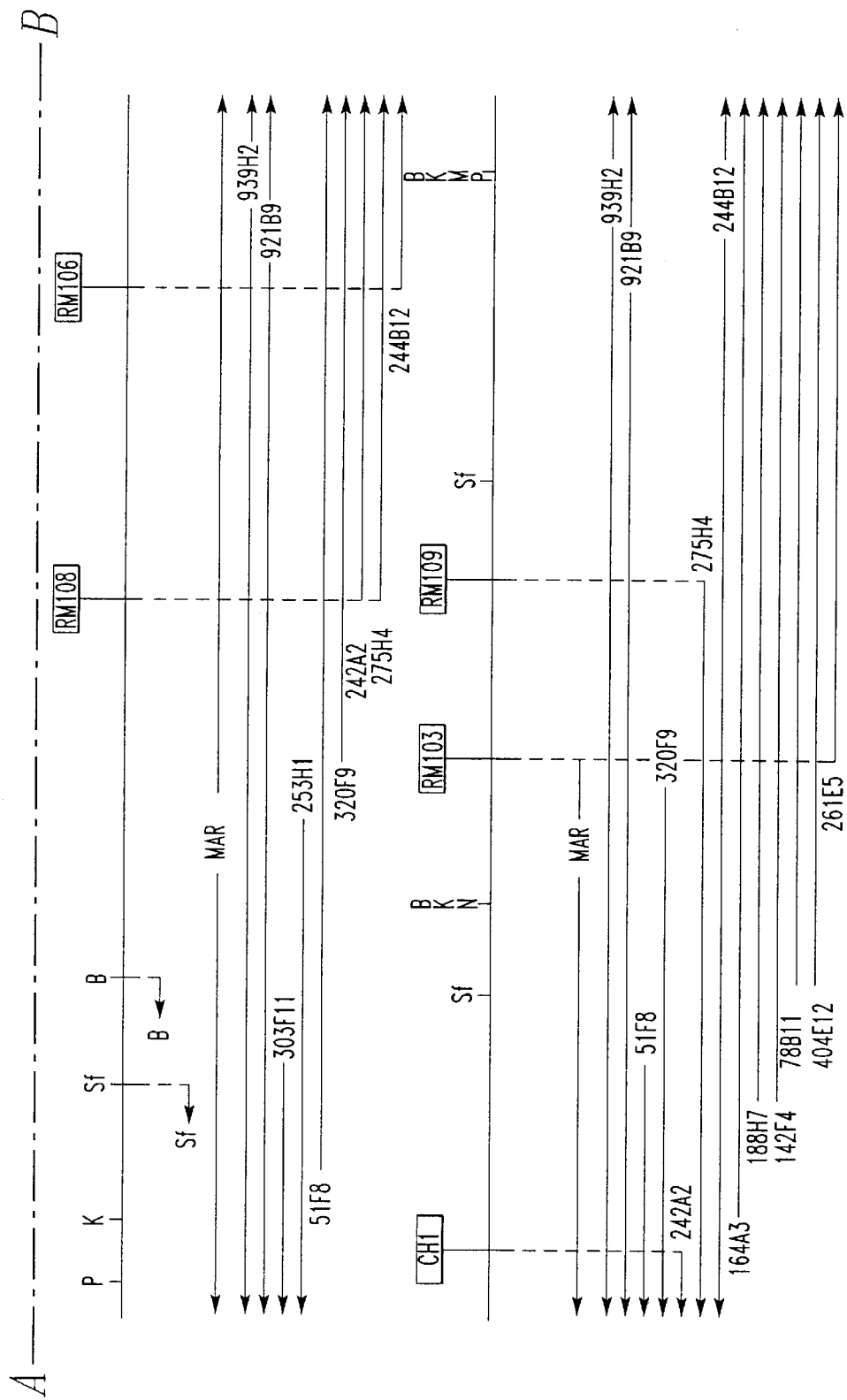
Figure 1C:
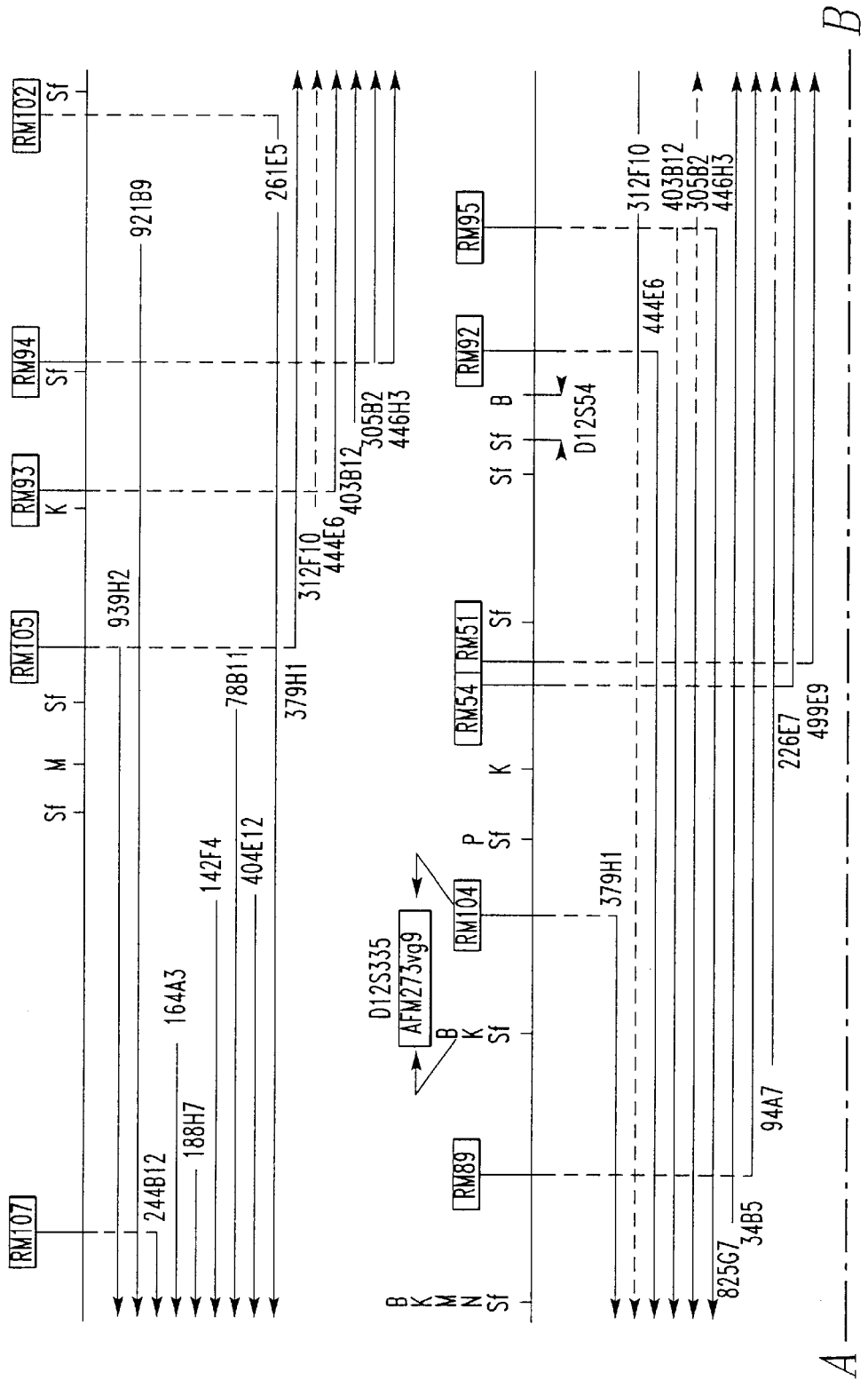
Figure 1C:
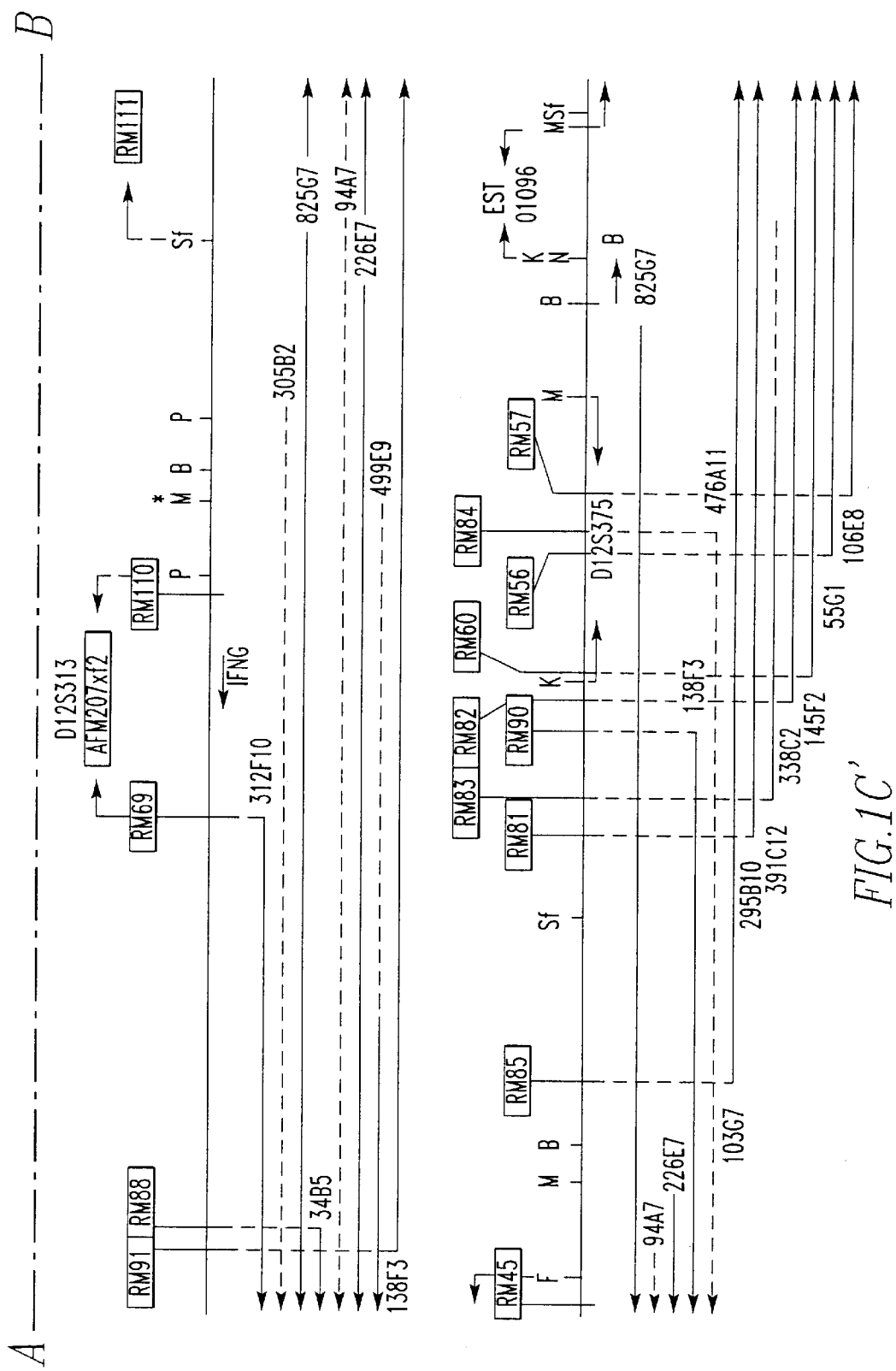
Figure 1D:
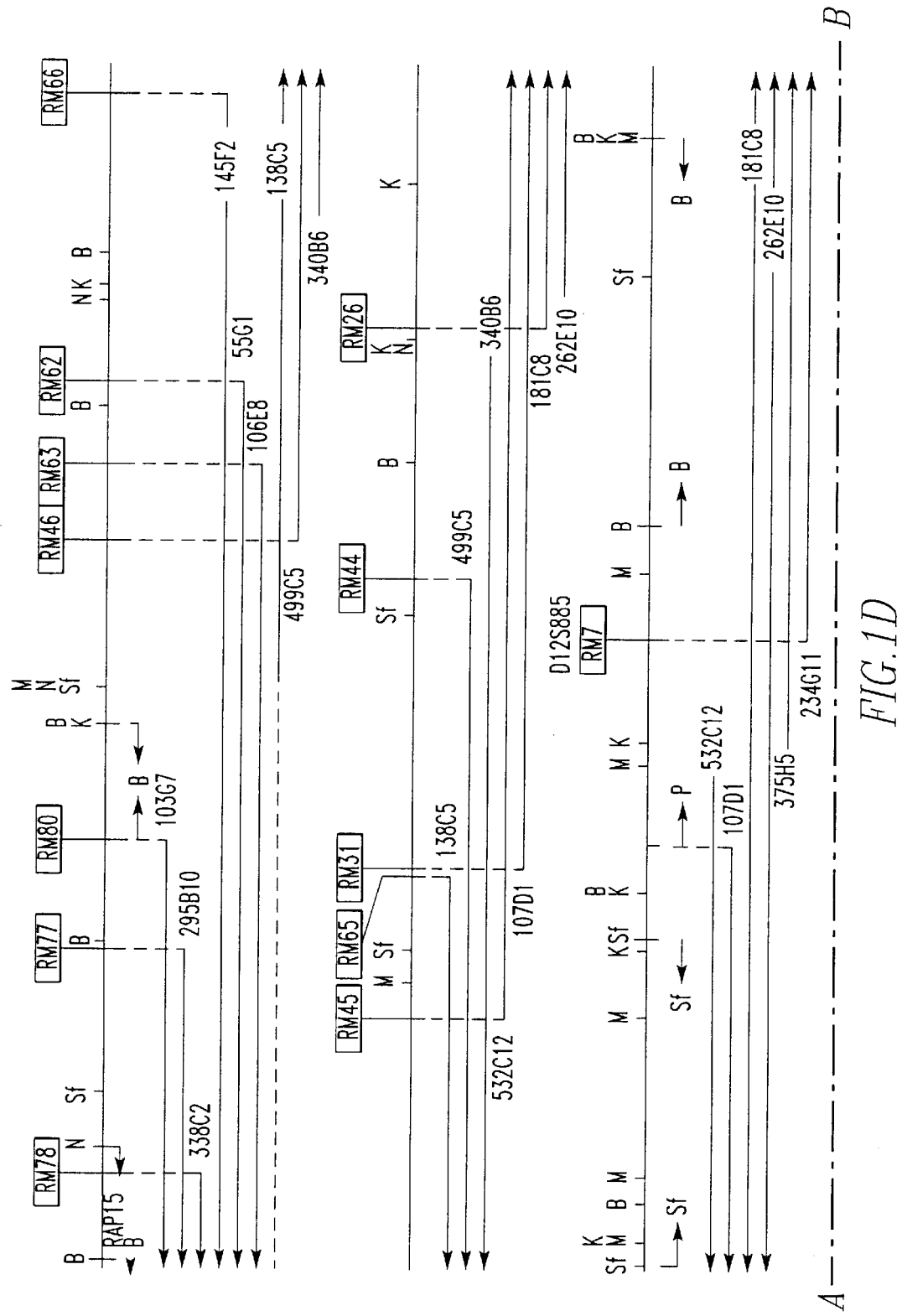
Figure 1D:
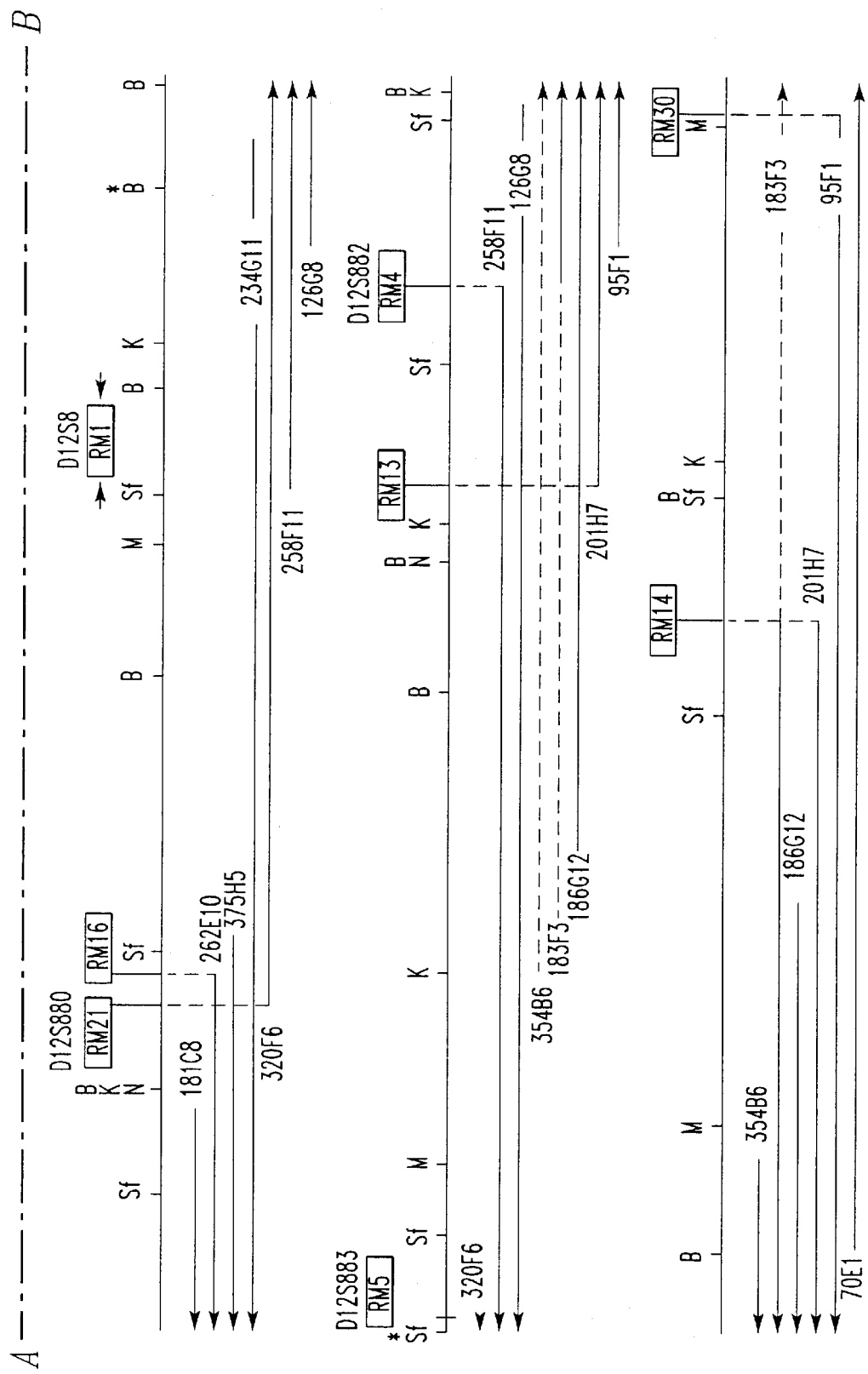

In this application the term "Multi-tumor Aberrant Growth (or MAG) gene" will be used to indicate the involvement of these types of genes in various types of cancer. The term refers to all members of the HMG and LIM gene families involved in non-physiological proliferative growth, and in particular involved in malignant or benign tumors, including atherosclerotic plaques. However, according to the invention it was furthermore found that even breaks outside the actual gene but in the vicinity thereof might result in aberrant growth. The term MAG gene is therefore also intended to include the immediate vicinity of the gene. The skilled person will understand that the "immediate vicinity" should be understood to include the surroundings of the gene in which breaks or rearrangements will result in the above defined non-physiological proliferative growth.

The term "wildtype cell" is used to indicate the cell not harbouring an aberrant chromosome or to a cell having a physiological expression level of the relevant gene. "Wildtype" or "normal" chromosome refers to a non-aberrant chromosome.

The present invention provides for various diagnostic and therapeutic applications that are based on the information that may be derived from the genes. This information not only encompasses its nucleotide sequence or the amino acid sequence of the gene product derived from the gene, but also involves the levels of transcription or translation of the gene.

The invention is thus two-fold. On the one hand the aberration in cell growth may be directly or indirectly caused by the physical breaks that occur in the gene or its vicinity. On the other hand the aberration in cell growth may be caused by a non-physiological expression level of the gene. This non-physiological expression level may be caused by the break, or may be due to another stimulus that activates or deactivates the gene. At present the exact mechanism or origin of the aberrant cell growth is not yet unraveled. However, exact knowledge on this mechanism is not necessary to define methods of diagnosis or treatment.

Diagnostic methods according to the invention are thus based on the fact that an aberration in a chromosome results in a detectable alteration in the chromosomes' appearance or biochemical behaviour. A translocation, for example will result in a first part of the chromosome (and consequently of the MAG gene) having been substituted for another (second) part (further referred to as "first and second substitution parts"). The first part will often appear someplace else on another chromosome from which the second part originates. As a consequence hybrids will be formed between the remaining parts of both (or in cases of triple translocations, even more) chromosomes and the substitution parts provided by their translocation partners. Since it has now been found that the breaks occur in a MAG gene this will result in hybrid gene products of that MAG gene. Markers, such as hybridising molecules like RNA, DNA or DNA/RNA hybrids, or antibodies will be able to detect such hybrids, both on the DNA level, and on the RNA or protein level.

For example, the transcript of a hybrid will still comprise the region provided by the remaining part of the gene/chromosome but will miss the region provided by the substitution part that has been translocated. In the case of inversions, deletions and insertions the gene may be equally afflicted.

Translocations are usually also cytogenetically detectable. The other aberrations are more difficult to find because they are often not visible on a cytogenetical level. The invention now provides possibilities for diagnosing all these types of chromosomal aberrations.

In translocations markers or probes based on the MAG gene for the remaining and substitution parts of a chromosome in situ detect the remaining part on the original chromosome but the substitution part on another, the translocation partner.

In the case of inversions for example, two probes will hybridise at a specific distance in the wildtype gene. This distance might however change due to an inversion. In situ such inversion may thus be visualized by labeling a set of suitable probes with the same or different detectable markers, such as fluorescent labels. Deletions and insertions may be detected in a similar manner.

According to the invention the above in situ applications can very advantageously be performed by using FISH techniques. The markers are e.g. two cosmids one of which comprises exons 1 to 3 of the MAG gene, while the other comprises exons 4 and 5. Both cosmids are labeled with different fluorescent markers, e.g. blue and yellow. The normal chromosome will show a combination of both labels, thus giving a green signal, while the translocation is visible as a blue signal on the remaining part of one chromosome (e.g. 12) while the yellow signal is found on another chromosome comprising the substitution part. In case the same labels are used for both probes, the intensity of the signal on the normal chromosome will be 100%, while the signal on the aberrant chromosomes is 50%. In the case of inversions one of the signals shifts from one place on the normal chromosome to another on the aberrant one.

In the above applications a reference must be included for comparison. Usually only one of the two chromosomes is afflicted. It will thus be very convenient to use the normal chromosome as an internal reference. Furthermore it is important to select one of the markers on the remaining or unchanging part of the chromosome and the other on the substitution or inverted part. In the case of the MAG gene of chromosome 12, breaks are usually found in the big intron between exons 3 and 4 as is shown by the present invention. Furthermore breaks were detected between exons 4 and 5. Probes based on exons 1 to 3 and 4 and 5, or probes based on either exon 4 or on exon 5 are thus very useful. As an-alternative a combination of probes based on boththranslocation or fusion partners may be used. For example, for the identification of lipomas one may use probes based on exons 1 to 3 of the HMGI-C gene on the one hand and based on the LIM domains of the LPP gene on the other hand.

Furthermore it was found that breaks might also occur outside the gene, i.e. 5' or 3' thereof. The choice of the probes will then of course include at least one probe hybrising to a DNA sequence located 5' or 3' of the gene.

"Probes" as used herein should be widely interpreted and include but are not limited to linear DNA or RNA strands, Yeast Artificial Chromosomes (YACs), or circular DNA forms, such as plasmids, phages, cosmids etc.

These in situ methods may be used on metaphase and interphase chromosomes.

Besides the above described in situ methods various diagnostic techniques may be performed on a more biochemical level, for example based on alterations in the DNA, RNA or protein, or on changes in the physiological expression level of the gene.

Basis for the methods that are based on alterations in the chromosome's biochemical behaviour is the fact that by choosing suitable probes, variations in the length or composition in the gene, transcript or protein may be detected on a gel or blot. Variations in length are visible because the normal gene, transcript(s) or protein(s) will appear in another place on the gel or blot then the aberrant one(s). In case of a translocation more than the normal number of spots will appear.

Based on the above principle the invention may thus for example relate to a method of diagnosing cells having a non-physiological proliferative capacity, comprising the steps of taking a biopsy of the cells to be diagnosed, isolating a suitable MAG gene-related macromolecule therefrom, and analysing the macromolecule thus obtained by comparison with a reference molecule originating from cells not showing a non-physiological proliferative capacity, preferably from the same individual. The MAG gene-related macromolecule may thus be a DNA, an RNA or a protein. The MAG gene may be either a member of the HMG family or of the LIM family.

In a specific embodiment of this type of diagnostic method the invention comprises the steps of taking a biopsy of the cells to be diagnosed, extracting total RNA thereof, preparing a first strand cDNA of the mRNA species in the total RNA extract or poly-A-selected fraction(s) thereof, which cDNA comprises a suitable tail; performing a PCR using a MAG gene specific primer and a tail-specific primer in order to amplify MAG gene specific cDNA's; separating the PCR products on a gel to obtain a pattern of bands; evaluating the presence of aberrant bands by comparison to wildtype bands, preferably originating from the same individual.

As an alternative amplification may be performed by means of the Nucleic Acid Sequence-Based Amplification (NASBA) technique [81] or variations thereof.

In another embodiment the method comprises the steps of taking a biopsy of the cells to be diagnosed, isolating total protein therefrom, separating the total protein on a gel to obtain essentially individual bands, optionally transferring the bands to a Western blot, hybridizing the bands thus obtained with antibodies directed against a part of the protein encoded by the remaining part of the MAG gene and against a part of the protein encoded by the substitution part of the MAG gene; visualising the antigen-antibody reactions and establishing the presence of aberrant bands by comparison with bands from wildtype proteins, preferably originating from the same individual.

In a further embodiment the method comprises taking a biopsy of the cells to be diagnosed; isolating total DNA therefrom; digesting the DNA with one or more so-called "rare cutter" restriction enzymes (typically "6- or more cutters"); separating the digest thus prepared on a gel to obtain a separation pattern; optionally trangsfering the separation pattern to a Southern blot; hybridizing the separation pattern in the gel or on the blot with a set of probes under hybridizing conditions; visualising the hybridizations and establishing the presence of aberrant bands by comparison to wildtype bands, preferably originating from the same individual.

Changes in the expression level of the gene may be detected by measuring mRNA levels or protein levels by means of a suitable probe.

Diagnostic methods based on abnormal expression levels of the gene may comprise the steps of taking a sample of the cells to be diagnosed; isolating mRNA therefrom; and establishing the presence and/or the (relative) quantity of mRNA transcribed from the MAG gene of interest in comparison to a control. Establishing the presence or (relative) quantity of the mRNA may be achieved by amplifying at least part of the mRNA of the MAG gene by means of RT-PCR or similar amplification techniques. In an alternative embodiment the expression level may be established by determination of the presence or the amount of the gene product (e.g. protein) by means of for example monoclonal antibodies.

The diagnostic methods of the invention may be used for diseases wherein cells having a non-physiological proliferative capacity are selected from the group consisting of benign tumors, such as the mesenchymal tumors hamartomas (e.g. breast and lung), adipose tissue tumors (e.g. lipomas), pleomorphic salivary gland adenomas, uterine leiomyomas, angiomyxomas, fibroadenomas of the breast, polyps of the endometrium, atherosclerotic plaques, and other benign tumors as well as various malignant tumors, including but not limited to sarcomas (e.g. rhabdomyosarcoma, osteosarcoma) and carcinomas (e.g. of breast, lung, skin, thyroid). The invention is not limited to the diagnosis and treatment of so-called benign and malignant solid tumors, but the principles thereof have been found to also apply to haematological malignancies like leukemias and lymphomas.

Recent publications indicate that atherosclerotic plaques also involve abnormal proliferation [26] of mainly smooth muscle cells and it was postulated that atherosclerotic plaques constitute benign tumors [27]. Therefore, this type of disorder is also to be understood as a possible indication for the use of the MAG gene family, in particular in diagnostic and therapeutic applications.

As already indicated above it has been found that in certain malignant tumors the expression level of the HMG genes is increased [28]. Until now the relevance of this observation was not understood. Another aspect of the invention thus relates to the implementation of the identification of the MAG genes in therapy. The invention for example provides anti-sense molecules or expression inhibitors of the MAG gene for use in the treatment of diseases involving cells having a non-physiological proliferative capacity by modulating the expression of the gene. A non-physiological high expression may thus be normalised by means of antisense RNA that is either administered to the cell or expressed thereby and binds to the mRNA, or antibodies directed to the gene product, which in turn may result in a normalization of the cell growth. The examples will demonstrate that expression of antisense RNA in leukemic cells results in a re-differentiation of the cells back to normal.

The invention thus provides derivatives of the MAG gene and/or its immediate environment for use in diagnosis and the preparation of therapeutical compositions, wherein the derivatives are selected from the group consisting of sense and anti-sense cDNA or fragments thereof, transcripts of the gene or fragments thereof, antisense RNA, triple helix inducing molecule or other types of "transcription clamps", fragments of the gene or its complementary strand, proteins encoded by the gene or fragments thereof, protein nucleic acids (PNA), antibodies directed to the gene, the cDNA, the transcript, the protein or the fragments thereof, as well as antibody fragments. Besides the use of direct derivatives of the genes and their surroundings (flanking sequences) in diagnosis and therapy, other molecules, like expression inhibitors or expression enhancers, may be used for therapeutic treatment according to the invention. An example of this type of molecule are ribozymes that destroy RNA molecules.

Besides the above described therapeutic and diagnostic methods the principles of the invention may also be used for producing a transgenic animal model for testing pharmaceuticals for treatment of MAG gene related malignant or benign tumors and atherosclerotic plaques. One of the examples describes the production of such an animal model.

It is to be understood that the principles of the present invention are described herein for illustration purposes only with reference to the HMGI-C gene mapping at chromosome 12 and the HMGI(Y) gene mapping at chromosome 6 and the LPP gene on chromosome 3. Based on the information provided in this application the skilled person will be able to isolate and sequence corresponding genes of the gene family and apply the principles of this invention by using the gene and its sequence without departing from the scope of the general concept of this invention.

The present invention will thus be further elucidated by the following examples which are in no way intended to limit the scope thereof.

EXAMPLES

Example 1

1. Introduction

This example describes the isolation and analysis of 75 overlapping YAC clones and the establishment of a YAC contig (set of overlapping clones), which spans about 6 Mb of genomic DNA around locus D12S8 and includes MAR. The orientation of the YAC contig on the long arm of chromosome 12 was determined by double-color FISH analysis. On the basis of STS-content mapping and restriction enzyme analysis, a long range physical map of this 6 Mb DNA region was established. The contig represents a useful resource for cDNA capture aimed at identifying genes located in 12q15, including the one directly affected by the various chromosome 12 aberrations.

2. Materials and Methods 2.1. Cell Lines

Cell lines PK89-12 and LIS-3/SV40/A9-B4 were used for Chromosome Assignment using Somatic cell Hybrids (CASH) experiments. PK89-12, which contains chromosome 12 as the sole human chromosome in a hamster genetic background, has been described before [29]. PK89-12 cells were grown in DME-F12 medium supplemented with 10% fetal bovine serum, 200 IU/ml penicillin, and 200 $\mu$g/ml streptomycin. Somatic cell hybrid LIS-3/SV40/A9-B4 was obtained upon fusion of myxoid liposarcoma cell line LIS-3/SV40, which carries a t(12;16)(q13;p11.2), and mouse A9 cells and was previously shown to contain der(16), but neither der(12) nor the normal chromosome 12 [30]. LIS-3/SV40/A9-B4 cells were grown in selective AOA-medium (AOA-medium which consisted of DME-F12 medium supplemented with 10% fetal bovine serum, 0.05 mM adenine, 0.05 mM ouabain, and 0.01 mM azaserine). Both cell lines were frequently assayed by standard cytogenetic techniques.

2.2. Nucleotide Sequence Analysis and Oligonucleotides.

Nucleotide sequences were determined according to the dideoxy chain termination method using a T7 polymerase sequencing kit (Pharmacia/LKB) or a dsDNA Cycle Sequencing System (GIBCO/BRL). DNA fragments were subcloned in pGEM-3Zf(+) and sequenced using FITC-labelled standard SP6 or T7 primers, or specific primers synthesized based upon newly obtained sequences. Sequencing results were obtained using an Automated Laser Fluorescent (A.L.F.) DNA sequencer (Pharmacia Biotech) and standard 30 cm, 6% Hydrolink$^R$, Long Range™ gels (AT Biochem). The nucleotide sequences were analyzed using the sequence analysis software Genepro (Riverside Scientific), PC/Gene (IntelliGenetics), the IntelliGenetics Suite software package (IntelliGenetics, Inc.), and oligo [31]. All oligonucleotides were purchased from Pharmacia Biotech.

2.3. Chromosome Preparations and Fluorescence in situ Hybridization (FISH)

FISH analysis of YAC clones was performed to establish their chromosomal positions and to identify chimeric clones. FISH analysis(of cosmid clones corresponding to STSs of YAC insert ends were performed to establish their chromosomal positions. Cosmids were isolated from human genomic library CMLW-25383 [32] or the arrayed chromosome 12-specific library constructed at Lawrence Livermore.National Laboratory (LL12NC01, ref. 33) according to standard procedures [34]. Routine FISH analysis was performed essentially as described before [30, 35]. DNA was labelled with biotin-11-dUTP (Boehringer) using the protocol of Kievits et al. [36]. Antifade medium, consisting of DABCO (2 g/100 ml, Sigma), 0.1 M Tris-HCL pH 8, 0.02%

Thimerosal, and glycerol (90%), and containing propidium iodide (0.5 μg/ml, Sigma) as a counterstain, was added 15 min before specimens were analyzed on a Zeiss Axiophot fluorescence microscope using a double band-pass filter for FITC/Texas red (Omega Optical, Inc.). Results were recorded on Scotch (3M) 640 ASA film.

For the double colour FISH experiments, LLNL12NCO1-96C11 was labelled with digoxygenin-11-dUTP (Boehringer) and cosmids LLNL12NCO1-1F6 and -193F10, with biotin-11-dUTP. Equal amounts of each probe were combined and this mixture was used for hybridization. After hybridization, slides were incubated for 20 min with Avidin-FITC and then washed as described by Kievits et al. [36]. Subsequent series of incubations in TNB buffer (0.1 M Tris-HCl pH 7.5, 0.15 M NaCl, 0.5% Boehringer blocking agent (Boehringer)) and washing steps were performed in TNT buffer (0.1 M Tris-HCl pH 7.5, 0.15 M NaCl, 0.05% Tween-20); all incubations were performed at 37° C. for 30 min. During the second incubation, Goat-α-Avidin-biotin (Vector) and Mouse-α-digoxygenin (Sigma) were applied simultaneously. During the third incubation, Avidin-FITC and Rabbit-α-Mouse-TRITC (Sigma) were applied. During the last incubation, Goat-α-Rabbit-TRITC (Sigma) was applied. After a last wash in TNT buffer, samples were washed twice in 1×PBS and then dehydrated through an ethanol series (70%, 90%, 100%). Antifade medium containing 75 ng/μl DAPI (Serva) as counterstain was used. Specimens were analyzed on a Zeiss Axiophot fluorescence microscope as described above.

2.4. Screening of YAC Libraries.

YAC clones were isolated from CEPH human genomic YAC libraries mark 1 and 3 [37, 38] made available to us by the Centre d'Étude du Polyphormisme Humain (CEPH). Screening was carried out as previously described [39]. Contaminating *Candida parapsylosis*, which was sometimes encountered, was eradicated by adding terbinafin (kindly supplied by Dr. Dieter Römer, Sandoz Pharma LTD, Basle, Switzerland) to the growth medium (final concentration: 25 μg/ml). The isolated YAC clones were characterized by STS-content mapping, contour-clamped homogeneous electric field (CHEF) gel electrophoresis [40], restriction mapping, and hybridization- and FISH analysis.

2.5. PCR Reactions

PCR amplification was carried out using a Pharmacia/LKB Gene ATAQ Controller (Pharmacia/LKB) in final volumes of 100 μl containing 10 mM Tris-HCl pH 8.3, 50 mM KCl, 1.5 mM MgCl$_2$, 0.01% gelatine, 2 MM dNTP's, 20 pmole of each amplimer, 2.5 units of Amplitaq (Perkin-Elmer Cetus), and 100 ng (for superpools) or 20 ng (for pools) of DNA. After initial denaturation for 5 min at 94° C., 35 amplification cycles were performed each consisting of denaturation for 1 min at 94° C., annealing for 1 min at the appropriate temperature (see Table I) and extension for 1 min at 72° C. The PCR reaction was completed by a final extension at 72° C. for 5 min. Results were evaluated by analysis of 10 μl of the reaction product on polyacrylamide minigels.

2.6. Pulsed-field Gel Electrophoresis and Southern Blot Analysis

Pulsed-field gel electrophoresis and Southern blot analysis were performed exactly as described by Schoenmakers et al. [39]. Agarose plugs containing high-molecular weight YAC DNA (equivalent to about 1×10$^8$ yeast cells) were twice equilibrated in approximately 25 ml TE buffer (pH 8.0) for min at 50° C. followed by two similar rounds of equilibration at room temperature. Plugs were subsequently transferred to round-bottom 2 ml eppendorf tubes and equilibrated two times for 30 min in 500 μl of the appropriate 1×restriction-buffer at the appropriate restriction temperature. Thereafter, DNA was digested in the plugs according to the suppliers (Boehringer) instructions for 4 h using 30 units of restriction endonuclease per digestion reaction. After digestion, plugs along with appropriate molecular weight markers were loaded onto a 1% agarose/0.25×TBE gel, sealed with LMP-agarose and size fractionated on a CHEF apparatus (Biorad) for 18 h at 6.0 V/cm using a pulse angle of 120 degrees and constant pulse times varying from 10 sec (separation up to 300 kbp) to 20 sec (separation up to 500 kbp). In the case of large restriction fragments, additional runs were performed, aiming at the separation of fragments with sizes above 500 kbp. Electrophoresis was performed at 14° C. in 0.25×TBE. As molecular weight markers, lambda ladders (Promega) and home-made plugs containing lambda DNA cut with restriction endonuclease HindIII were used. After electrophoresis, gels were stained with ethidium bromide, photographed, and UV irradiated using a stratalinker (Stratagene) set at 120 mJ. DNA was subsequently blotted onto Hybond N$^+$ membranes (Amersham) for 4–16 h using 0.4 N NaOH as transfer buffer. After blotting, the membranes were dried for 15 min at 80° C., briefly neutralised in 2×SSPE, and prehybridised for at least 3 h at 42° C. in 50 ml of a solution consisting of 50% formamide, 5×SSPE, 5×Denhardts, 0.1% SDS and 200 μg/ml heparin. Filters were subsequently hybridised for 16 h at 42° C. in 10 ml of a solution consisting of 50% formamide, 5×SSPE, 1×Denhardts, 0.1% SDS, 100 μg/ml heparin, 0.5% dextran sulphate and 2–3×10$^6$ cpm/ml of labelled probe. Thereafter, membranes were first washed two times for 5 min in 2×SSPE/0.1% SDS at room temperature, then for 30 min in 2×SSPE/0.1% SDS at 42° C. and, finally, in 0.1×SSPE/0.1% SDS for 20 min at 65° C. Kodak XAR-5 films were exposed at −80° C. for 3–16 h, depending on probe performance. Intensifying screens (Kyokko special 500) were used.

2.7. Generation of STSs from YAC Insert Ends

STSs from YAC insert ends were obtained using a vectorette-PCR procedure in combination with direct DNA sequencing analysis, essentially as described by Geurts et al. [41]. Primer sets were developed and tested on human genomic DNA, basically according to procedures described above. STSs will be referred to throughout this application by their abbreviated names (for instance: RM1 instead of STS 12-RM1) for reasons of convenience.

3. Results 3.1. Assembly of a YAC Contig Around Locus D12S8

In previous studies [39], a 800 kb YAC contig around D12S8 was described. This contig consisted of the following three partially overlapping, non-chimeric CEPH YAC clones: 258F11, 320F6, and 234G11. This contig was used as starting point for a chromosome walking project to define the DNA region on the long arm of chromosome 12 that encompasses the breakpoints of a variety of benign solid tumors, which are all located proximal to D12S8 and distal to CHOP. Initially, chromosome walking was performed bidirectionally until the size of the contig allowed reliable determination of the orientation of it. In the bidirectional and subsequent unidirectional chromosome walking steps, the following general procedure was used. First, rescuing and sequencing the ends of YAC clones resulted in DNA markers characterizing the left and right sides of these (Table I). Based on sequence data of the ends of forty YAC inserts, primer sets were developed for specific amplification of DNA; establishing STSs (SEQ ID Nos:17–102) (Table II). Their localization to 12q13-qter was determined by CASH as well as FISH after corresponding cosmid clones were isolated. It should be noted that isolated YAC clones were often evaluated by FISH analysis too, thus not only revealing the chromosomal origin of their inserts but also, for a number of cases, establishing and defining their chimeric nature. Moreover, it should be emphasized that data obtained by restriction endonuclease analysis of overlapping YAC clones were also taken into account in the YAC clone evaluation and subsequent alignment. With the sequentially selected and evaluated primer sets, screening of the YAC and cosmid libraries was performed to isolate the building blocks for contig-assembly. Therefore, contig-assembly was performed using data derived from FISH- and STS-content mapping as well as restriction endonuclease analysis. Using this approach, we established a YAC contig consisting of 75 overlapping YAC clones, covering approximately 6 Mb of DNA (FIG. 1). This contig appeared to encompass the chromosome 12 breakpoints of all tumor-derived cell lines studied [39]. Characteristics of the YACs that were used to build this contig are given in Table I.

3.2. Establishment of the Chromosomal Orientation of the YAC Contig

To allow unidirectional chromosome walking towards the centromere of chromosome 12, the orientation of the DNA region flanked by STSs RM14 and RM26 (approximate size: 1450 kb) was determined by double-color interphase FISH analysis. Cosmid clones corresponding to these STSs (i.e. LL12NC01-1F6 (RM14) and LL12NC01-96C11 (RM26)) were differentially labelled to show green or red signals, respectively. As a reference locus, cosmid LL12NC01-193F10 was labelled to show green signals upon detection. LL12NC01-193F10 had previously been mapped distal to the breakpoint of LIS-3/SV40 (i.e. CHOP) and proximal to the chromosome 12q breakpoints in lipoma cell line Li-14/SV40 and uterine leiomyoma cell line LM-30.1/SV40. LL12NC01-1F6 and LL12NC01-96C11 were found to be mapping distal to the 12q breakpoints in lipoma cell line Li-14/SV40 and uterine leiomyoma cell line LM-30.1/SV40. Therefore, LL12NC01-193F10 was concluded to be mapping proximal to both RM14 and RM26 (unpublished results). Of 150 informative interphases scored, 18% showed a signal-order of red-green-green whereas 72% showed a signal order of green-red-green. Based upon these observations, we concluded that RM26 mapped proximal to RM14, and therefore we continued to extend the YAC contig from the RM26 (i.e. proximal) side of our contig only. Only the cosmids containing RM14 and RM26 were ordered by double-color interphase mapping; the order of all others was deduced from data of the YAC contig. Finally, it should be noted that the chromosomal orientation of the contig as proposed on the basis of results of the double-color interphase FISH studies was independently confirmed after the YAC contig had been extended across the chromosome 12 breakpoints as present in a variety of tumor cell lines. This confirmatory information was obtained in extensive FISH studies in which the positions of YAC and cosmid clones were determined relative to the chromosome 12q13-q15 breakpoints of primary lipomas, uterine leiomyomas, pleomorphic salivary gland adenomas, and pulmonary chondroid hamartomas or derivative cell lines [24, 42, 25, 43].

3.3. Construction of a Rare-Cutter Physical Map from the 6 Mb YAC Contig Around D12S8

Southern blots of total yeast plus YAC DNA, digested to completion with rare-cutter enzymes (see Materials and Methods) and separated on CHEF gels, were hybridized sequentially with i) the STS used for the initial screening of the YAC in question, ii) pYAC4 right arm sequences, iii) pYAC4 left arm sequences, and iv) a human ALU-repeat probe (BLUR-8). The long-range restriction map that was obtained in this way, was completed by probing with PCR-isolated STSs/YAC end probes. Occasionally double-digests were performed.

Restriction maps of individual YAC clones were aligned and a consensus restriction map was established. It is important to note here that the entire consensus rare-cutter map was supported by at least two independent clones showing a full internal consistency.

3.4. Physical Mapping of CA Repeats and Monomorphic STSs/ESTs

Based upon integrated mapping data as emerged from the Second International Workshop on Human Chromosome 12 [44], a number of published markers was expected to be mapping within the YAC contig presented here. To allow full integration of our mapping data with those obtained by others, a number of markers were STS content-mapped on our contig, and the ones found positive were subsequently sublocalized by (primer-)hybridization on YAC Southern blots. Among the markers that were found to reside within the contig presented here were CA repeats D12S313 (AFM207f2) and D12S335 (AFM273vg9) [45], D12S375 (CHLC GATA3F02), and D12S56 [46]. Furthermore, the interferon gamma gene (IFNG) [47], the ras-related protein gene Rap1B [48], and expressed sequence tag EST01096 [49] were mapped using primer sets which we developed based on publicly available sequence data (see Table II). Markers which were tested and found negative included D12S80 (AFM102d6), D12S92 (AFM203va7), D12S329 (AFM249h9) and D12S344 (AFM296d9).

4. Discussion

In the present example the establishment of a YAC contig and rare-cutter physical map covering approximately 6 Mb on 12q15, a region on the long arm of human chromosome 12 containing MAR in which a number of recurrent chromosomal aberrations of benign solid tumors are known to be mapping was illustrated.

The extent of overlap between individual YACs has been carefully determined, placing the total length of the contig at approximately 6 Mb (FIG. 1). It should be noted that our sizing-data for some of the YAC clones differ slightly from the sizes determined by CEPH [50]. It is our belief that this is most probably due to differences in the parameters for running the pulsed-field gels in the different laboratories.

Using restriction mapping and STS-content analysis, a consensus long range physical map (FIG. 1) was constructed. The entire composite map is supported by at least two-fold coverage. In total over 30 Mb of YAC DNA was characterized by restriction and STS content analysis, corresponding to an average contig coverage of about 5 times. Although the "inborn" limited resolution associated with the technique of pulsed-field electrophoresis does not allow very precise size estimations, comparison to restriction mapping data obtained from a 500 kb cosmid contig contained within the YAC contig presented here showed a remarkable good correlation. Extrapolating from the cosmid data, we estimate the accuracy of the rare-cutter physical map presented here at about 10 kb.

The results of our physical mapping studies allowed integration of three gene-specific as well as five anonymous markers isolated by others (indicated in between arrows in FIG. 1). The anonymous markers include one monomorphic and four polymorphic markers. Five previously published YAC-end-derived single copy STSs (RM1, RM4, RM5, RM7, and RM21) as well as four published CA repeats (D12S56, D12S313, D12S335, and D12S375) and three published gene-associated STSs/ESTs (RAPLB, EST01096, and IFNG) have been placed on the same physical map and this will facilitate (linkage-) mapping and identification of a number of traits/disease genes that map in the region. Furthermore, we were able to place onto the same physical map, seventy two YAC-end-derived (Table I) and eight cosmid-end- or inter-ALU-derived DNA markers (CH9, RM1, RM110, RM111, RM130, RM131, RM132, and RM133), which were developed during the process of chromosome walking. The PYTHIA automatic mail server at PYTHIA@anl.gov was used to screen the derived sequences of these DNA markers for the presence of repeats. For forty three of these seventy two DNA markers (listed in Table II), primer sets were developed and the corresponding STSs were determined to be single copy by PCR as well as Southern blot analysis of human genomic DNA. The twenty nine remaining DNA markers (depicted in the yellow boxes) represent YAC-end-derived sequences for which we did not develop primer sets. These YAC-end sequences are assumed to be mapping to chromosome 12 on the basis of restriction mapping. The final picture reveals an overall marker density in this region of approximately one within every 70 kb.

The analysis of the contig presented here revealed many CpG-rich regions, potentially HTF islands, which are known to be frequently associated with housekeeping genes. These CpG islands are most probably located at the 5' ends of as yet unidentified genes: it has been shown that in 90% of cases in which three or more rare-cutter restriction sites coincide in YAC DNA there is an associated gene [51]. This is likely to be an underestimate of the number of genes yet to be identified in this region because 60% of tissue-specific genes are not associated with CpG islands [52] and also because it is possible for two genes to be transcribed in different orientations from a single island [53].

While several of the YAC clones that were isolated from the CEPH YAC library mark 1 were found to be chimeric, overlapping YAC clones that appeared to be non-chimeric based on FISH, restriction mapping and STS content analysis could be obtained in each screening, which is in agreement with the reported complexity of the library. The degree of chimerism for the CEPH YAC library mark 1 was determined at 18% (12 out of 68) for the region under investigation here. The small number of YACs from the CEPH YAC library mark 3 (only 7 MEGA YACs were included in this study) did not allow a reliable estimation of the percentage of chimeric clones present in this library. The average size of YACs derived from the mark 1 library was calculated to be 381 kb ; non-chimeric YACs (n=58) had an average size of 366 kb while chimeric YACs (n=12) were found to have a considerable larger average size; i.e. 454 kb.

In summary, we present a 6 Mb YAC contig corresponding to a human chromosomal region which is frequently rearranged in a variety of benign solid tumors. The contig links over 84 loci, including 3 gene-associated STSs. Moreover, by restriction mapping we have identified at least 12 CpG islands which might be indicative for genes residing there. Finally, four CA repeats have been sublocalized within the contig. The integration of the genetic, physical, and transcriptional maps of the region provides a basic framework for further studies of this region of chromosome 12. Initial studies are likely to focus on MAR and ULCR12, as these regions contain the breakpoint cluster regions of at least three distinct types of solid tumors. The various YAC clones we describe here are valuable resources for such studies. They should facilitate the search for genes residing in this area and the identification of those directly affected by the chromosome 12q aberrations of the various benign solid tumors.

Example 2

1. Introduction

It was found that the 1.7 Mb Multiple Aberration Region on human chromosome 12q15 harbors recurrent chromosome 12 breakpoints frequently found in different benign solid tumor types. In this example the identification of an HMG gene within MAR that appears to be of pathogenetical relevance is described. Using a positional cloning approach, the High Mobility Group protein gene HMGI-C was identified within a 175 kb segment of MAR and its genomic organization characterized. By FISH, within this gene the majority of the breakpoints of seven different benign solid tumor types were pinpointed. By Southern blot and 3'-RACE analysis, consistent rearrangements in HMGI-C and/or expression of altered HMGI-C transcripts were demonstrated. These results indicate a link between a member of the HMG gene family and benign solid tumor development.

2. Materials and Methods 2.1. Cell Culture and Primary Tumor Specimens.

Figure 3B:
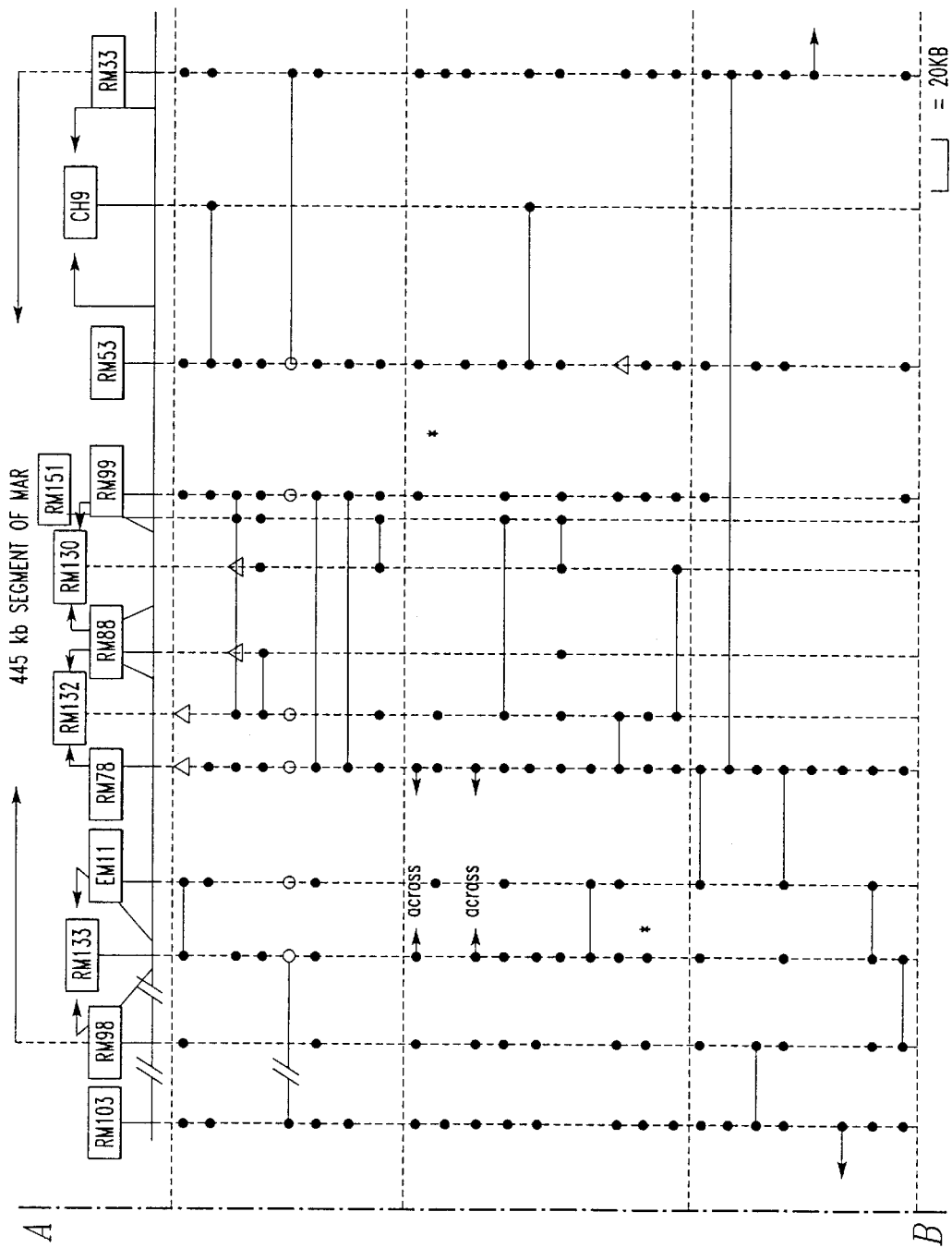
FIG. 3 is a schematic representation of FISH mapping data obtained for tumor cell lines with chromosome 12q13–q15 aberrations.

Tumor cell lines listed in FIG. 3 were established by a transfection procedure [54] and have been described before in [39, 24] and in an article of Van de Ven et al., Genes Chromosom. Cancer 12, 296–303 (1995) enclosed with this application as ANNEX 1. Cells were grown in TC199 medium supplemented with 20% fetal bovine serum and were assayed by standard cytogenetic techniques at regular intervals. The human hepatocellular carcinoma cell lines Hep 3B and Hep G2 were obtained from the ATCC (accession numbers ATCC HB 8064 and ATCC HB 8065) and cultured in DMEM/F12 supplemented with 4% Ultroser (Gibco/BRL). Primary solid tumors were obtained from various University Clinics.

2.2. YAC and Cosmid Clones

YAC clones were isolated from the CEPH mark 1 [57] and mark 3 [58] YAC libraries using a combination of PCR-based screening [59] and colony hybridization analysis. Cosmid clones were isolated from an arrayed human chromosome 12-specific cosmid library (LL12NC01) [60] obtained from Lawrence Livermore National Laboratory (courtesy P. de Jong). LL12NC01-derived cosmid clones are indicated by their microtiter plate addresses; i.e. for instance 27E12.

Cosmid DNA was extracted using standard techniques involving purification over Qiagen tips (Diagen). Agarose plugs containing high-molecular weight yeast+YAC DNA (equivalent to $1\times10^9$ cells ml$^{-1}$) were prepared as described before [61]. Plugs were thoroughly dialysed against four changes of 25 ml $T_{10}E_1$ (pH 8.0) followed by two changes of 0.5 ml 1×restriction buffer before they were subjected to either pulsed-field restriction enzyme mapping or YAC-end rescue. YAC-end rescue was performed using a vectorette-PCR procedure in combination with direct solid phase DNA sequencing, as described before in reference 61. Inter-Alu PCR products were isolated using published oligonucleotides TC65 or 517 [62] to which SalI-tails were added to facilitate cloning. After sequence analysis, primer pairs were developed using the OLIGO computer algorithm [61].

2.3. DNA Labelling

DNA from YACs, cosmids, PCR products and oligonucleotides was labelled using a variety of techniques. For FISH, cosmid clones or inter-Alu PCR products of YACs were biotinylated with biotin-11-dUTP (Boehringer) by nick translation. For filter hybridizations, probes were radio-labelled with $\alpha$-$^{32}$P-dCTP using random hexamers [62]. In case of PCR-products smaller than 200 bp in size, a similar protocol was applied, but specific oligonucleotides were used to prime labelling reactions. Oligonucleotides were labelled using $\gamma$-$^{31}$P-ATP.

2.4. Nucleotide Sequence Analysis and PCR Amplification

Nucleotide sequences were determined as described in Example 1. Sequencing results were analyzed using an A.L.F. DNA sequencer™ (Pharmacia Biotech) on standard 30 cm, 6% Hydrolink$^R$, Long Range™ gels (AT Biochem). PCR amplifications were carried out essentially as described before [39].

2.5. Rapid Amplification of cDNA Ends (RACE)

Rapid amplification of 3' cDNA-ends (3'-RACE) was performed using a slight.modification of part of the GIBCO/BRL 33-ET protocol. For first strand cDNA synthesis, adapter primer (AP2) AAG GAT CCG TCG ACA TC(T)$_{17}$ (SEQ ID NO:1) was used. For both initial and secondary rounds of PCR, the universal amplification primer (UAP2) CUA CUA CUA CUA AAG GAT CCG TCG ACA TCA (SEQ ID NO:2) was used as "reversed primer". In the first PCR round the following specific "forward primers" were used: i) 5'-CTT CAG CCC AGG GAG AAC-3' (exon 1)(SEQ ID NO:3), ii) 5'-CAA GAG GCA GAC CTA GGA-3' (exon 3)(SEQ ID NO:4), or iii) 5' -AAC AAT GCA ACT TTT AAT TAC TG-3' (3'-UTR)(SEQ ID NO:5), In the second PCR round the following specific forward primers (nested primers as compared to those used in the first round) were used: i) 5'-CAU CAU CAU CAU CGC CTC AGA AGA GAG GAC-3' (exon 1)(SEQ ID NO:6), ii) 5'-CAU CAU CAU CAU GTT CAG AAG AAG CCT GCT-3' (exon 4)(SEQ ID NO:7), or iii) 51-CAU CAU CAU CAU TTG ATC TGA TAA GCA AGA GTG GG-3' (3'-UTR)(SEQ ID NO:8). CUA/CAU-tailing of the nested, specific primers allowed the use of the directional CloneAmp cloning system (GIBCO/BRL).

3. Results 3.1. Development of Cosmid Contig and STS Map of MAR Segment

Figure 2A:
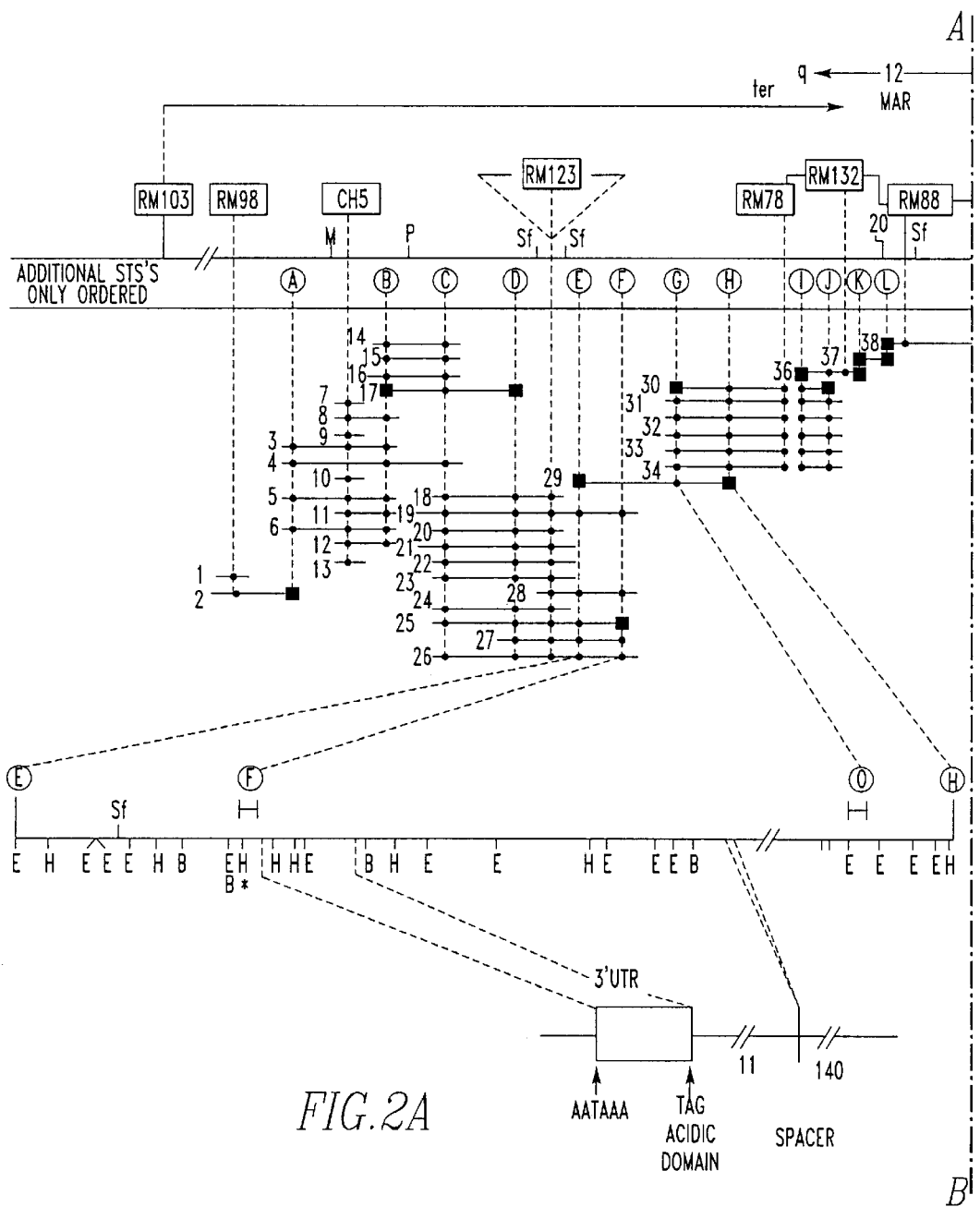
FIG. 2 is a contig of overlapping cosmids, long range restriction and STS map spanning a segment of MAR of about 445 kb.
Figure 2B:
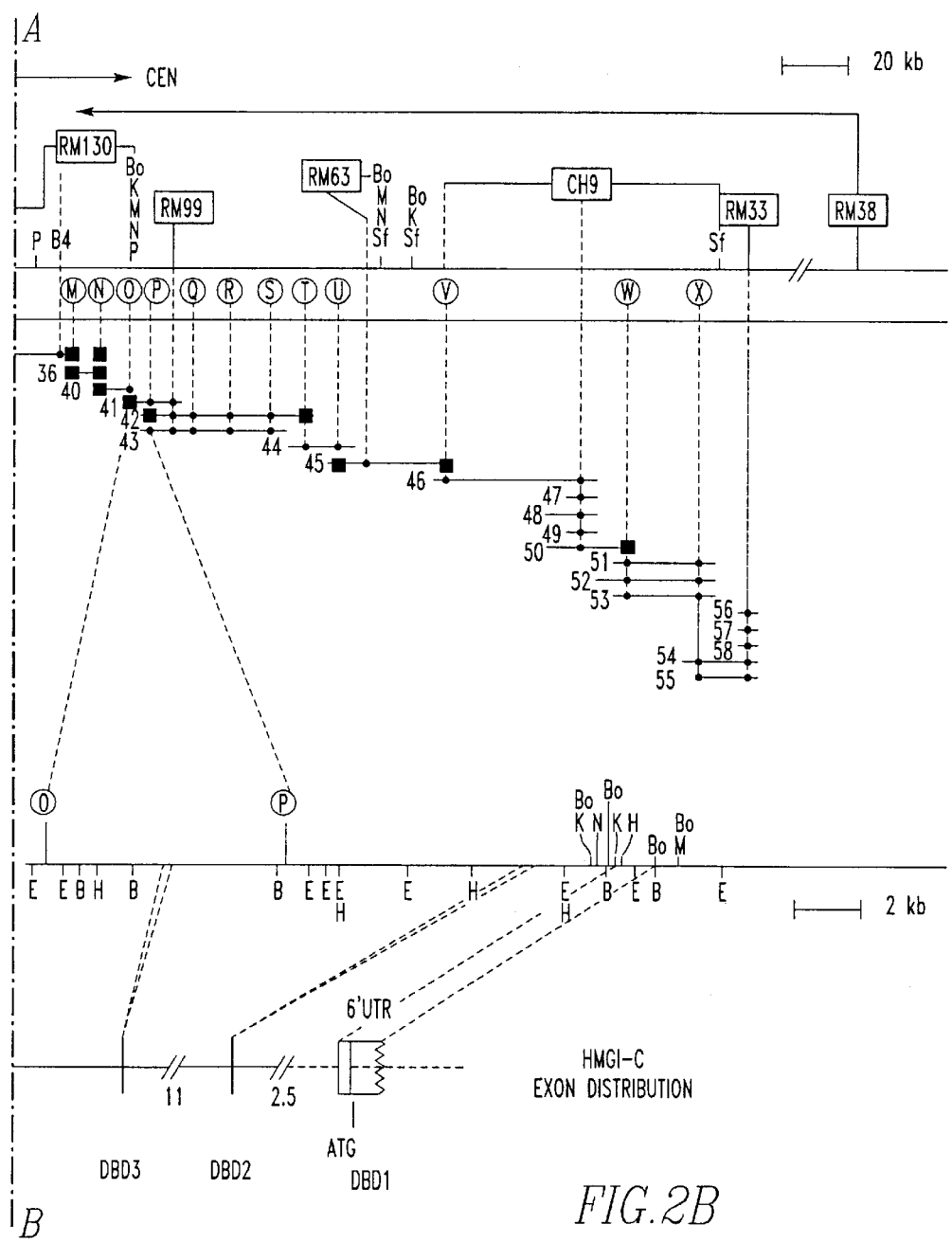

During the course of a positional cloning effort focusing on the long arm of human chromosome 12, we constructed a yeast artificial chromosome (YAC) contig spanning about 6 Mb and consisting of 75 overlapping YACS. For a description thereof reference is made to Example 1. This contig encompasses MAR (see also FIG. 2), in which most of the chromosome 12q13-q15 breakpoints as present in a variety of primary benign solid tumors (34 tumors of eight different types tested sofar; Table 5) and tumor cell lines (26 tested sofar, derived from lipoma, uterine leiomyoma, and pleomorphic salivary gland adenoma; FIG. 3) appear to cluster. We have developed both a long-range STS and rare cutter physical map of MAR and found, by FISH analysis, most of the breakpoints mapping within the 445 kb subregion of MAR located between STSs RM33 and RM98 (see FIG. 2 and 3). FISH experiments, including extensive quality control, were performed according to routine procedures as described before [25, 39, 24, 42, 36] To further refine the distribution of breakpoints within this 445 kb MAR segment, a cosmid contig consisting of 54 overlapping cosmid clones has been developed and a dense STS map (FIG. 2) established.

The cosmid contig was double-checked by comparison to the rare cutter physical map and by STS content mapping.

3.2. Clustering of the Chromosome 12q Breakpoints Within a 175 kb DNA Segment of MAR The chromosome 12q breakpoints in the various tumor cell lines studied was pinpointed within the cosmid contig by FISH (FIG. 3). As part of our quality control FISH experiments [25, 39, 24, 423, selected cosmids were first tested on metaphase spreads derived from normal lymphocytes. FISH results indicated that the majority (atleast 18 out of the 26 cases) of the chromosome 12 breakpoints in these tumor cell lines were found to be clustering within the 175 kb DNA interval between RM99 and RM133, indicating this interval to constitute the main breakpoint cluster region. FISH results obtained with Li-501/SV40 indicated that part of MAR was translocated to an apparently normal chromosome 3; a chromosome aberration overseen by applied cytogenetics. Of interest to note, finally, is the fact that the breakpoints of uterine leiomyoma cell lines LM-5.1/SV40, LM-65/SV40, and LM-608/SV40 were found to be mapping within the same cosmid clone; i.e. cosmid 27E12.

We also performed FISH experiments on eight different types of primary benign solid tumors with chromosome 12q13-q15 aberrations (Table 4). A mixture of cosmid clones 27E12 and 142H1 was used as molecular probe. In summary, the results of the FISH studies of primary tumors were consistent with those obtained for the tumor cell lines. The observation that breakpoints of each of the seven different tumor types tested were found within the same 175 kb DNA interval of MAR suggested that this interval is critically relevant to the development of these tumors and, therefore, might harbor the putative MAG locus or critical part(s) of it.

3.3. Identification of Candidate Genes Mapping Within MAR

In an attempt to identify candidate genes mapping within the 175 kb subregion of MAR between STSs RM99 and RM133, we used 3'-terminal exon trapping and genomic sequence sampling (GSS) [63]. Using the GSS approach, we obtained DNA sequence data of the termini of a 4.9 kb BamHI subfragment of cosmid 27E12, which was shown by FISH analysis to be split by the chromosome 12 aberrations in three of the uterine leiomyoma cell lines tested. A BLAST [64] search revealed that part of these sequences displayed sequence identity with a publicly available partial cDNA sequence (EMBL accession #. Z31595) of the high mobility group (HMG) protein gene HMGI-C [65], which is a member of the HMG gene family [66]. In light of these observations, HMGI-C was considered a candidate MAG gene and studied in further detail.

3.4. Genomic Organization of HMGI-C and Rearrangements in Benign Solid Tumors

Since only 1200 nucleotides of the HMGI-C transcript (reported size approximately 4 kb [65, 67]) were publicly available, we first determined most of the remaining nucleotide sequences of the HMGI-C transcript (Gensank, #U28749). This allowed us to subsequently establish the genomic organization of the gene. Of interest to note about the sequence data is that a CT-repeat is present in the 5'-UTR of HMGI-C and a GGGGT-pentanucleotide repeat in the 3'-UTR, which might be of regulatory relevance. Comparison of transcribed to genomic DNA sequences (GenBank, #U28750, U28751, U28752, U28753, and U28754) of the gene revealed that HMGI-C contains at least 5 exons (FIG. 2). Transcriptional orientation of the gene is directed towards the telomere of the long arm of the chromosome. Each of the first three exons encode a putative DNA binding domain (DBD), and exon 5 encodes an acidic domain, which is separated from the three DBDs by a spacer domain encoded by exon 4. The three DBD-encoding exons are positioned relatively close together and are separated by a large intron of about 140 kb from the two other exons, which in turn are separated about 11 kb from each other. Of particular interest to emphasize here is that the five exons are dispersed over a genomic region of at least 160 kb, thus almost covering the entire 175 kb main MAM breakpoint cluster region described above. Results of molecular cytogenetic studies, using a mixture of cosmids 142H1 (containing exons 1–3) and 27E12 (containing exons 4 and 5) as molecular probe, clearly demonstrate that the-HMGI-C gene is directly affected by the observed chromosome 12 aberrations in the majority of the tumors and tumor cell lines that were evaluated (FIG. 3; Table 4). These cytogenetic observations were independently confirmed by Southern blot analysis in the case of LM-608/SV40 (results not shown) LM-30.1/SV40 [24], and Ad-312/SV40; probes used included CH76, RM118-A, and EM26. The failure to detect the breakpoints of LM-65/SV40, LM-609/SV40, Ad-211/SV40, Ad-263/SV40, Ad-302/SV40, Li-14/SV40, and Li-538/SV40 with any of these three probes was also consistent with the FISH data establishing the relative positions of the breakpoints in MAR (cf. FIG. 3). These results made HMGI-C a prime candidate to be the postulated MAG gene.

3.5. Expression of Aberrant HMGI-C Transcripts in Benign Solid Tumor Cells.

In the context of follow-up studies, it was of interest to test for possible aberrant HMGI-C expression. Initial Northern blot studies revealed that transcripts of MGI-C could not be detected in a variety of normal tissues (brain, heart, lung, liver, kidney, pancreas, placenta, skeletal muscle) tested as well as in a number of the tumor ell lines listed in FIG. 3 (data not shown). It is known hat HMGI-C mRNA levels in normal differentiated tissues are very much lower than in malignant tissues [65, 67]. As a control in our Northern studies, we included hepatoma cell line Hep 3B, which is known to express relatively high levels of HMGI-C. We readily detected two major HMGI-C transcripts, approximately 3.6 and 3.2 kb in size; with the differences in molecular weight most likely due to differences in their 5'-noncoding regions. In an alternative and more sensitive approach to detect HMGI-C or 3'-aberrant HMGI-C transcripts, we have performed 3'-RACE experiments. In control experiments using a number of tissues with varying HMGI-C transcription levels (high levels in Hep 3B hepatoma cells, intermediate in Hep G2 hepatoma cells, and low in myometrium, normal fat tissue, and pseudomyxoma), we obtained 3'-RACE clones which, upon molecular cloning and nucleotide sequence analysis, appeared to represent perfect partial cDNA copies of 3'-HMGI-C mRNA sequences; no matter which of the three selected primer sets was used (see Methodology). RACE products most likely corresponding to cryptic or aberrantly spliced HMGI-C transcripts were occasionally observed; their ectopic sequences were mapped back to HMGI-C intron 3 or 4.

In similar 3'-RACE analysis of ten different primary tumors or tumor cell lines derived from lipoma, uterine leiomyoma, and pleomorphic salivary gland adenoma, we detected both constant and unique PCR products. The constant PCR products appeared to represent, in most cases, perfect partial cDNA copies of 3'-HMGI-C mRNA sequences. They most likely originated from a presumably unaffected HMGI-C allele and might be considered as internal controls. The unique PCR products of the ten tumor cell samples presented here appeared to contain ectopic sequences fused to HMGI-C sequences. In most cases, the ectopic sequences were found to be derived from the established translocation partners, thus providing independent evidence for translocation-induced rearrangements of the HMGI-C gene. Information concerning nucleotide sequences (SEQ ID Nos: 103–159), diversion points, and chromosomal origins of the ectopic sequences of these RACE products is summarized in Table 5. It should be noted that chromosomal origins of ectopic-sequences was established by CASH (Chromosome Assignment using Somatic cell Hybrids) analysis using the NIGMS Human/Rodent Somatic Hybrid Mapping Panel 2 obtained from the Coriell Cell Repositories. Chromosomal assignment was independently confirmed by additional data for cases pCH1111, pCH172, pCH174, pCH193, and pCH117, as further outlined in Table 5. Taking into account the limitations of conventional cytogenetic analysis, especially in cases with complex karyotypes, the chromosome assignments of the ectopic sequences are in good agreement with the previous cytogenetic description of the translocations.

Somewhat unexpected were the data obtained with Ad-312/SV40, as available molecular cytogenetic analysis had indicated its chromosome 12 breakpoint to map far outside the HMGI-C gene; over 1 Mb [42]. The ectopic sequences appeared to originate from chromosome 1 (more precisely from a segment within M.I.T. YAC contig WC-511, which is partially mapping at 1p22), the established translocation partner (FIG. 2). Further molecular analysis is required to precisely define the effect on functional expression of the aberrant HMGI-C gene in this particular case. Of further interest to note here, is that the sequences coming from chromosome 1 apparently remove the GGGGT repeat observed in the 3'-UTR region of HMGI-C, as this repeat is not present in the RACE product. In contrast, in primary uterine leiomyoma LM-#58 (t(8;12)(q24;q14-q15)), which was shown to have its breakpoint also in the 3'-UTR, this repeat appeared to be present in the RACE product. Therefore, removal of this repeat is most probably not critical for tumor development. The results with primary tumor LM-#168.1, in which the X chromosome is the cytogenetically assigned translocation partner, revealed that the ectopic sequences were derived from chromosome 14; the preferential translocation partner in leiomyoma. It is possible that involvement of chromosome 14 cannot be detected by standard karyotyping in this particular case, as turned out to be the case for Li-501/SV40. In primary lipoma Li-#294 (t(8;12)(q22;q14)), two alternative ectopic sequences were detected. Additional CASH analysis using a hybrid cell mapping panel for regional localization of probes to human chromosome 8 [68] revealed that these were both derived from chromosome 8q22-qter (Table 5). It is very well possible that these RACE products correspond to alternatively spliced transcripts. Finally, in four of the cases (Table 5, cases pCH114, pCH110, pCH109, pCH116), the RACE products appeared to correspond to cryptic or aberrantly spliced HMGI-C transcripts, as the corresponding ectopic sequences were found to be derived from either HMGI-C intron 3 or 4. Such RACE products have also been observed in the control experiments described above. In conclusion, the detection of aberrant HMGI-C transcripts in the tumor cells provides additional strong support of HMGI-C being consistently rearranged by the various chromosome 12 aberrations. It should be noted that the aberrant HMGI-C transcripts in the various cases should be characterized in full length before any final conclusion can be drawn about biological implications.

A first and preliminary evaluation of isolated ectopic sequences revealed in phase open reading frames of variable length. In the case of primary tumor LM-#25, for instance, already the second codon in the ectopic sequences appeared to be a stop codon (Table 5). A note of caution is appropriate here, as sequence data have been obtained only for clones that were produced via two rounds of extensive (probably mutations inducing) PCR. For Li-501/SV40, it is of interest to note that, in Northern blot analysis, the isolated ectopic sequences detected a transcript of over 10 kb in a variety of tissues, including heart, kidney, liver, lung, pancreas, placenta, and skeletal muscle, but not in brain (data not shown). As chromosome 3 is the preferred partner in the chromosome 12q13-q15 translocations in lipomas and the chromosome 3 breakpoints of various lipomas were found to be spanned by YAC clone CEPH192B10, the detected transcript might correspond to a putative lipoma-preferred partner gene (LPP).

4. Discussion

In ANNEX 1 it was demonstrated that the chromosome 12q13-q15 breakpoints of lipoma, pleomorphic salivary gland adenoma, and uterine leiomyoma, irrespective of their cytogenetic assignments in the past to segment q13, q14, or q15 of chromosome 12, all cluster within the 1.7 Mb DNA interval designated MAR. In support of the claimed clustering of breakpoints is a recent study by Schoenberg Fejzo et al. [14], identifying a CEPH mega-YAC spanning the chromosome 12 translocation breakpoints in two of the three tumor types. In the present study, we have conclusively demonstrated by FISH analysis that chromosome 12 breakpoints of seven different solid tumor types are clustering within a relatively small (175 kb) segment of MAR. For some tumor cell lines, Southern blot data were obtained and these were always in support of the FISH results. From all these observations, we conclude that this segment of MAR constitutes a major target area for the chromosome 12 aberrations in these tumors and that it is likely to represent the postulated MAG locus: the multi-tumor aberrant growth locus that might be considered as common denominator in these tumors.

Within the 175 kb MAR segment, we have identified the HMGI-C gene and determined characteristics of its genomic organization. Structurally, the HMGI-C-encoded phosphoprotein consists of three putative DNA binding domains, a spacer region, and an acidic carboxy-terminal domain, and contains potential sites of phosphorylation for both casein kinase II and p34/cdc2 [65, 67]. We have provided strong evidence that HMGI-C is a prime candidate target gene involved in the various tumor types studied here. In FISH studies, the breakpoints of 29 out of 33 primary tumors were found to be mapping between two highly informative cosmids 142H1 and 27E12; the first one containing the three DBD-encoding exons and the second one, the remaining exons that code for the two other domains. Therefore, the majority of the breakpoints map within the gene, most of them probably within the 140 kb intron (intron 3), which is also in line with FISH results obtained with the 26 tumor cell lines that were evaluated. It should also be noted that the 5'-end of the HMGI-C gene is not yet fully characterized. As HMGI(Y), another member of this gene family, is known to possess various alternative first exons (69], the size of the HMGI-C gene might be larger than yet assumed. Further support that HMGI-C is affected by the chromosome 12 aberrations can be deduced from the results of the 3'-RACE experiments. Aberrant HMGI-C transcripts were detected in tumor cells, consisting of transcribed HMGI-C sequences fused to newly acquired sequences, in most cases clearly originating from the chromosomes that were cytogenetically identified as the translocation partners. It is noteworthy that many chromosomes have been found as translocation partner in the tumors studied. This observed heterogeneity in the reciprocal breakpoint regions involved in these translocations resembles that of a variety of hematological malignancies with chromosome 11q23 rearrangements involving the MLL gene [70], the translational product of which carries an amino-terminal motif related to the DNA-binding motifs of HMGI proteins.

An intriguing issue pertains to the effect of the chromosome 12 aberrations on expression of the HMGI-C gene and the direct physiological implications. Some functional characteristics of HMGI-C are known or may be deduced speculatively from studies of other family members. As it binds in the minor groove of DNA, it has been suggested that HMGI-C may play a role in organising satellite chromatin or act as a transcription factor (71, 72]. Studies on HMGI(Y), which is the member most closely related to HMGI-C, have suggested that HMGI(Y) may function as a promoter-specific accessory factor for NF-κ B transcriptional activity [73]. MGI(Y) has also been shown to stimulate or inhibit DNA inding of distinct transcriptional factor ATF-2 isoforms [74]. Both studies indicate that the protein may simply constitute a structural component of the transcriptional apparatus functioning in promoter/enhancer contexts. In a recent report on high mobility group protein 1 (HMG1), yet another member of the HMG gene family with a similar domain structure as HMGI-C and acting as a quasi-transcription factor in gene transcription, a truncated HMG1 protein lacking the acidic carboxy-terminal region was shown to inhibit gene transcription [75]. It was put forward that the acidic terminus of the HMG1 molecule is essential for the enhancement of gene expression in addition to elimination of the repression caused by the DNA binding. As most of the chromosome 12 breakpoints seem to occur in the 140 kb intron, separation of the DBDs from the acidic carboxy-terminal domain seems to occur frequently. In case the acidic domain in HMGI-C has a similar function as the one in HGMI(Y), the result of the chromosome 12 aberrations is likely to affect gene expression. Finally, it should be noted that the fate of the sequences encoding the acidic carboxy-terminal region is not yet known. As HMGI-C is the first member of the HMG gene family that might be implicated in the development of benign tumors, the question arises as to whether other members of this family could also be involved. The HMG protein family consists of three subfamilies: i) the HMG1 and 2 type proteins, which have been found to enhance transcription in vitro and may well be members of a much larger class of regulators with HMG boxes; ii) the random-coil proteins HMG14 and 17 with an as yet unknown function; iii) the HMGI-type proteins, which bind to the minor groove and include HMGI-C, HMGI, and HMGI-Y; the latter two are encoded by the same gene. It is of interest to note that published mapping positions of members of the HMG family coincide with published chromosome breakpoints of benign solid tumors such as those studied here. The HMGI(Y) gene, for instance, has been mapped to human chromosome 6p21 [69], which is known to be involved in recurrent translocations observed in uterine leiomyoma, lipoma, and pleomorphic salivary gland adenoma [76]. As listed in the Human Genome Data Base, not all known members of the HMG family have been chromosomally assigned yet, although for some of them a relatively precise mapping position has been establisher. For instance, HMG17 to chromosome 1p36.1-p35, HMG1L to 13q12, and HMG14 to 21q22.3; all chromosome segments in which chromosome breakpoints of the tumor types studied here have been reported [76]. Whether HMGI(Y) or any other of these HMG members are indeed affected in other subgroups of these tumors remains to be established. Of interest to mention, furthermore, are syndromes such as Bannayan-Zonana (McKusick #153480), Proteus (McKusick #176920), and Cowden (McKusick #158350); the latter syndrome is also called multiple hamartoma syndrome. In 60% of the individuals with congenital Bannayan-Zonana syndrome, a familial macrocephaly with mesodermal hamartomas, discrete lipomas and hemangiomas were found [70].

Finally, one aspect of our results should not escape attention. All the tumors that were evaluated in this study were of mesenchymal origin or contained mesenchymal components. It would be of great interest to find out whether the observed involvement of HMGI-C is mesenchyme-specific or may be found also in tumors of non-mesenchymal origin. The various DNA clones we describe here are valuable resources to address this important issue and should facilitate studies to conclusively implicate the HMGI-C gene in tumorigenesis.

Example 3

Rearrangements of Another Member of the HMG Gene Family

1. Introduction

This example clearly demonstrates that within a given tumor entity (e.g. pulmonary chondroid hamartomas, uterine leiomyomas, endometrial polyps) tumors, histologically practically indistinguishable from each other, arise if either the HMGI-C gene or the HMGI(Y) gene is affected by chromosomal rearrangements. Thus, indeed a group of genes leading to aberrant mesenchymal growth including but not restricted to HMGI-C and HMGI(Y) can be defined.

2. Material and Methods 2.1. Chromosome Preparation

Chromosome preparation followed routine methods. Cells were treated with 30 µl colcemide (10 µg/ml) for 2–3 h and then harvested using the trypsin method (0.05% trypsin, 0.02% EDTA) followed by a hypotonic shock in six fold diluted medium TC 199 for 20 minutes at room temperature and methanol:acetic acid (3:1) fixation. Chromosomes were then GTG-banded.

2.2. In situ Hybridization

In situ hybridisation was performed as outlined in one of the previous examples.

2.3. PAC Library Screening

The PAC library (Genome Systems Library Screening Service, St. Louis, Mo., USA) was screened by PCR with a primer set specific for the HMGI(Y) gene. For screening we designed the forward primer with the sequence:

5'-CTC CAA GAC AGG CCT CTG ATG T-3' (intron 3)(SEQ ID No:9) and the reverse primer:

5'-ACC ACA GGT CCC CTT CAA ACT A-3' (intron 3)(SEQ ID No:10) giving rise to a fragment of 338 bp. For amplification the following thermal cycling was used: 94° C., 5 min, (94° C., 1 min, 59° C., 1 min, 72° C., 2 min)×30, 72° C., 10 min.

2.4. DNA Preparations From PAC Clones

Bacterial colonies containing single PAC clones were inoculated into LB medium and grown overnight at 37° C. 660 µl of the overnight culture were diluted into 25 ml of LB medium and grown to an $OD_{550}$ of 0.05–0.1. By addition of IPTG to a final concentration of 0.5 mM the P1 lytic replicon was induced. After addition of IPTG, growth was continued to an $OD_{550}$ of 0.5–1.5, and plasmid DNA was extracted using the alkaline lysis procedure recommended by Genome Systems.

3. Results

The primer set for screening the human PAC library was designed from sequences belonging to intron 3 of HMGI(Y). Because of sequence homology between HMGI-C and HMGI(Y) the amplified sequence of 338 bp was tested by homology search to be specific exclusively for HMGI(Y). Library screening resulted in three positive PAC clones that had an average insert length of approximately 100 kb. Two of these clones (Pac604, Pac605) were used for the following FISH studies. In order to prove if HMGI(Y) is rearranged in tumors with translocations involving 6p21.3 in either simple or complex form we performed FISH analysis on metaphase spreads from four primary pulmonary chondroid hamartomas and two endometrial polyps all with 6p21.3 abnormalities. For each case 20 metaphases were scored. At least one of the two PAC clones Pac604 and Pac605 described above was across the breakpoint in all six cases analyzed. These results clearly show that the breakpoints of the tumors with 6p21 aberrations investigated herein are clustered either within the HMGI(Y) gene or its close vicinity.

Example 4

Hybrid HMGI-C in Lipoma Cells

CDNA clones of the chromosome 3-derived lipoma-preferred partner gene LPP (>50 kb) were isolated and the nucleotide sequence thereof established. Data of a composite cDNA are shown in FIG. 4. An open reading frame for a protein (612 amino acids (aa)) with amino acid sequence similarity (over 50%) to zyxin of chicken was identified. Zyxin is a member of the LIM protein family, whose members all possess so-called LIM domains [78]. LIM domains are cysteine-rich, zinc-binding protein sequences that are found in a growing number of proteins with divers functions, including transcription regulators, proto-oncogene products, and adhesion plaque constituents. Many of the LIM family members have been postulated to play a role in cell signalling and control of cell fate during development. Recently, it was demonstrated that LIM domains are modular protein-binding interfaces [79]. Like zyxin, which is present at sites of cell adhesion to the extracellular matrix and to other cells, the deduced LPP-encoded protein (FIG. 6) possesses three LIM domains and lacks classical DNA-binding homeodomains.

In 3'-RACE analysis of Li-501/SV40, a HMG1-C containing fusion transcript was identified from which a hybrid protein (324 aa) could be predicted and which was subsequently predicted to consist of the three DBDs (83 aa) of HMG1-C and, carboxy-terminally of these, the three LIM domains (241 aa) encoded by LPP. In PCR analysis using appropriate nested amplimer sets similar HMGI-C/LPP hybrid transcripts were detected in various primary lipomas and lipoma cell lines carrying a t(3;12) and also in a cytogenetically normal lipoma. These data reveal that the cytogenetically detectable and also the hidden t(3;12) translocations in lipomas seem to result consistently in the in-phase fusion of the DNA-binding molecules of HMG1-C to the presumptive modular protein-binding interfaces of the LPP-encoded protein, thereby replacing the acidic domain of HMG1-C by LIM domains. Consequently, these protein-binding interfaces are most likely presented in the nuclear environment of these lipoma cells, where they might affect gene expression, possibly leading to aberrant growth control. Out of the large variety of benign mesenchymal tumors with chromosome 12q13-q15 aberrations, this is the first example of a chromosome translocation partner contributing recurrently and consistently to the formation of a well-defined tumor-associated HMG1-C fusion protein.

FIG. 5 shows the cDNA sequence of the complete isolated LPP gene.

Example 5

Diagnostic Test for Lipoma

A biopsy of a patient having a lipoma was taken. From the material thus obtained total RNA was extracted using the standard TRIZOL™ LS protocol from GIBCO/BRL as described in the manual of the manufacturer. This total RNA was used to prepare the first strand of CDNA using reverse transcriptase (GIBCO/BRL) and an oligo dT(17) primer containing an attached short additional nucleotide stretch. The sequence of the primer used is as described in Example 2, under point 2.5. RNase H was subsequently used to remove the RNA from the synthesized DNA/RNA hybrid molecule. PCR was performed using a gene specific primer (Example 2, point 2.5. ) and a primer complementary to the attached short additional nucleotide stretch. The thus obtained PCR product was analysed by gel electroforesis. Fusion constructs were detected by comparing them with the background bands of normal cells of the same individual.

In an additional experiment a second round of hemi-nested PCR was performed using one internal primer and the primer complementary to the short nucleotide stretch. The sensitivity of the test was thus significantly improved.

Figure 8:
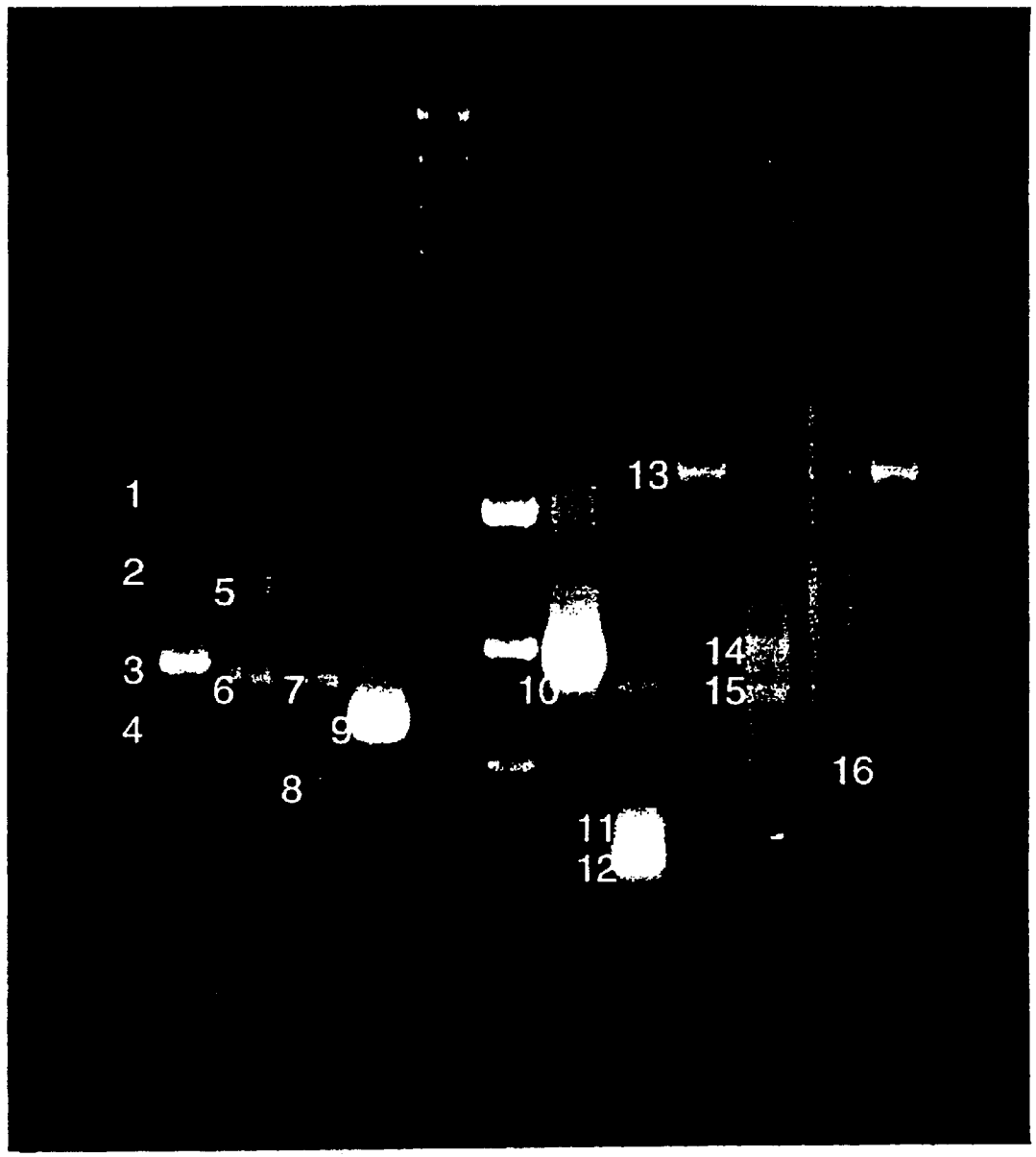
FIG. 8 is a photograph of a gel of PCR products obtained as described in Example 5.

FIG. 8 shows a typical gel.

Example 6

Aberrations of 12q14-15 and 6p21 in Pulmonary Chondroid Hamartomas

1. Introduction

Pulmonary chondroid hamartomas (PCH) are often detected during X-ray examination of the lung as so-called coin lesions. However, lung metastases of malignant tumors and rarely lung cancers can also present as coin lesions. This example shows that FISH requiring a minimal amount of tumor cells can be used to correctly distinguish between the majority of PCHs and malignant tumors. Thus the test can successfully be applied e.g. to tumor cells obtained by fine needle aspiration.

2. Materials and Methods

Samples from a total of 80 histologically characterized PCHs were included in this study. Cell cultures, chromosome preparations and FISH were obtained or performed as described in the previous examples.

3. Results

Cytogenetic studies revealed that of the 80 PCHs studied cytogenetically 51 revealed detectable aberrations involving either 12q14-15 or 6p21. By FISH using either a pool of cosmids belonging to the HMGI-C gene or using the PAC clones of HMGI(Y) described in the previous example we were able to detect hidden structural rearrangements of those regions in 4 additional cases (3 with 12q and one with 6p involvement). Therefore, the FISH test alone can be used for a kit to precisely detect the rearrangement of either the HMGI-C or the HMGI(Y) gene rearrangements in more than 50% of the PCHs and is thus a valuable additonal tool for the diagnosis of these tumors (without being restricted to this type of tumors as shown in two of the other examples).

Example 7

Diagnosis of Soft Tissue Tumors Particularly of Adipocytic Origin

1. Introduction

Adipocyte tissue tumors often cause diagnostic difficulties particularly when material taken from fine needle aspiration biopsies or cryosections has to be evaluated. This examples demonstrates the validity of the FISH test for the differential diagnosis of adipocyte tissue tumors and rare soft tissue tumors.

2. Materials and Methods 2.1. Tumor Samples

Tumor samples from three soft tissue tumors were investigated by FISH. Sample one (1) was from a adipocytic tumor and histologically it was either an atypical lipoma or a well-differentiated liposarcoma. The second case (tumor 2) was diagnosed to be most likely a myxoid liposarcoma but other types of malignant soft tissue tumors including aggressive angiomyxoma were also considered. The third tumor (tumor 3) was also of adipocytic origin and both a lipoma and a well differentiated liposarcoma were considered.

2.2. Isolation of Cells and FISH

The tumor samples were enzymatically disaggregated following routine methods. The resulting single cell suspensions were centrifuged and the suspensions were fixed using methanol:glacial acetic acid (3:1) at room temperature for 1 hour. The cell suspensions were then dropped on clean dry slides and allowed to age for 6 hours at 60° C. FISH was performed using molecular probes from the HMGI-C gene as described in the previous examples.

3. Results

At the interphase level tumor 1 and 2 both showed split signals for one of the alleles. These findings are compatible with the diagnosis of benign tumors i.e. an atypical lipoma in the first case and an aggressive angiomyxoma in the second case. They allowed to rule out the presence of malignant adipocytic tissue tumors.

In the third case the FISH revealed a high degree of amplification of the MAR region or part of it. Since the amplification units observed in giant marker or ring chromosomes in well-differentiated liposarcomas can involve the MAR region these findings leads to the diagnosis of a well-differentiated liposarcoma. The three cases presented within this example show the usefulness of the DNA probes described. They can be used in a kit for a relatively simple and fast interphase FISH experiment offering an additional tool for the diagnosis of soft tissue tumors.

Example 8

Expression of the HMGI-C Gene in Normal Tissue

1. Introduction

It is the aim of this example to show that the expression of the HMGI-C gene is mainly restricted to human tissues during embryonic and fetal development. In contrast, in most normal tissues of the adult particularly, including those tissues and organs tumors with HMGI-C rearrangements can arise from, on expression can be noted. This indicates that even the transcriptional re-activation of the gene can inititate tumorigenesis. On the other hand it underlines the usefulness of antisense strategies (including those antisense molecules directed towards the normal HMGI-C mRNA) to inhibit or stop tumor growth.

2. Materials and Methods 2.1. Tissue Samples

All adult tissue samples used for this study were taken from surgically removed tissue frozen in liquid nitrogen within a period of 15 min after removal. Most of the samples were from adjacent normal tissue removed during tumor surgery. In detail we have used 8 samples taken from fat tissues at various anatomical sites, 20 samples taken from myometrial tissue, 8 samples taken from lung tissue, 4 samples taken from the salivary glands (Glandula parotis and Glandula submandibularis), one tissue sample taken from the heart muscle, 25 samples taken from breast tissue from patients of different ages, 2 samples from the brain, 3 liver samples, 7 samples taken from renal tissue, and embryonic/fetal tissue (extremeties, 6 samples) from embryos/fetuses (10–14th gestational week) after abortion from socio-economic reasons.

In addition, three cell lines were used: As a control for HMGI-C expression we used the hepatoma cell line Hep 3B and the cell line L14 established from a lipoma with the typical translocation t(3;12). HeLa cells were used as a negative control because RT experiments reproduced for 10 times did not reveal HMGI-C expression in our own studies.

2.2. RT-PCR for the Expression of HMGI-C 100 mg of tissue sample was homogenized, and RNA was isolated using the trizol reagent (GibcoBRL, Eggenstein, Germany) containing phenol and isothiocyanate. cDNA was synthesized using a poly(A)-oligo(dt)17 primer and M-MLV reverse transcriptase (GibcoBRL, Eggenstein, Germany). Then, a hemi-nested PCR was performed.

For first and second PCR the same lower primer (Revex 4) (5'-TCC TCC TGA GCA GGC TTC-3' (exon 4/5))(SEQ ID No:11) was used. In the first round of PCR the specific upper primer (SE1) (5'-CTT CAG CCC AGG GAC AAC-3' (exon 1)(SEQ ID No:12), and in the second round of PCR the nested upper primer (P1) (5'-CGC CTC AGA AGA GAG GAC-3' (exon 1)(SEQ ID No:13) was used. Both rounds of PCR were performed in a 100 µl volume containing 10 mM Tris/HCl pH 8.0, 50 mM KCl, 1.5 mM $MgCl_2$, 0.001% gelatin, 100 µM DATP, 100 µM dTTP, 100 µM dGTP, 100 µM dCTP, 200 nM upper primer, 200 nM lower primer, and 1 unit/100 µl AmpliTaq polymerase (Perkin Elmer, Weiterstadt, Germany). Amplification was performed for 30 cycles (1 min 94° C., 1 min 53° C., 2 min 72° C.). As template in the first round of PCR cDNA derived from 250 ng total RNA, and in the second round of PCR 1 µl of the first PCR reaction mix was used.

2.3. Control Assay for Intact mRNA/cDNA

As control reaction for intact RNA and cDNA PCR a test based on the amplification of the cDNA of the housekeeping gene glyceraldehyde 3-phosphate dehydrogenase (GAPDH). PCR reaction was performed for 35 cycles under the same conditions as described above for the first round of PCR of HMGI-C expression.

3. Results

As for the expression studies all experiments were repeated at least twice. To assure that all RNA and cDNA preparations used for the RT-PCRs were intact (otherwise resulting in false negative results) routinely a RT-PCR for expression of the housekeeping gene GAPDH was performed. A positive GAPDH RT-PCR results in a 299 bp fragment. Only samples revealing a positive GAPDH RT-PCR were included in this study. As the result of RT-PCR in HMGI-C positive cells such as Hep 3B and L14 a specific 220 bp fragment is detectable. HeLa cells did not show an expression of HMGI-C. Except for two myometrial samples (most likely due to myomas at a submicroscopic level) all normal tissue samples taken from adult individuals did not show any detectable level of HMGI-C expression. In contrast, all fetal/embryonic tissues tested revealed HMGI-C expression.

Example 9

Expression of the HMGI-C Gene as a Diagnostic Tool for the Early Detection of Leukemias 1. Introduction Cytogenetically detectable aberrations affecting the HMGI-C gene have been found in a variety of benign solid tumors of mesenchymal origin. Apparently, the aberrations also lead to the transcriptional activation of the gene. Since blood cells are also of mesenchymal origin, it was tempting to check leukemic cells for HMGI-C expression. The present example shows that the activation of the gene in cells of the peripheral blood is a suitable marker indicating immature cells/abnormal stem cells found in leukemias. Since the expression of HMGI-C can be determined with a high degree of sensitivity the RT-PCR for the expression of the gene can be used for a very early detection of various hematological diseases.

2. Materials and Methods

Samples from peripheral blood of 27 patients with different types of leukemias including 19 patients with Philadelphia-chromosome positive CML, 5 patients with AML, and 3 patients with ALL were used for determination of HMGI-C expression. Blood samples from 15 healthy probands served as controls.

RT-PCR for the expression of HMGI-C was performed as outlined in example 8.

3. Results

Whereas expression of HMGI-C was clearly detectable in all blood samples from leukemic patients there was no expression noted in any of the blood samples taken from the control persons. There is no evidence that the transcriptional activation of the gene is due to mutations affecting the gene or its surroundings. It is more reasonable to assume that the activation is rather a secondary effect related to the immaturity of the cells or their abnormal proliferation. However, the high and even improvable sensitivity makes e.g. a kit based on the RT-PCR for the expression of the HMGI-C gene a very suitable diagnostic tool.

Example 10

The Transcriptional Re-expression of the HMGI-C Gene can Lead to the Initiation of the Tumors 1. Introduction This example clearly shows that for some tumor entities chromosomal breakpoints located 5' of the HMGI-C gene do also exist indicating that the transcriptional up-regulation of the gene is sufficient to initiate growth of the corresponding tumor types.

2. Materials and Methods 2.1. Cell Culture

After surgery the tumor samples (three pulmonary chondroid hamartomas, one uterine leiomyoma) were washed with Hank's solution supplemented with penicillin (200 IU/ml) and streptomycin (200 µg/ml). Tumors were disaggregated with collagenase for 5–6 h at 37° C. The suspension containing small fragments and single cells was resuspended in culture medium TC 199 with Earle's salts supplemented with 20% fetal bovine serum, 200 IU/ml penicillin, and 200 µg/ml streptomycin.

2.2. Chromosome Preparations

Chromosome preparation followed routine methods. Cells were treated with 30 µl colcemide (10 µg/ml) for 2–3 h and then harvested using the trypsin method (0.05% trypsin, 0.02% EDTA) followed by a hypotonic shock in six fold diluted medium TC 199 for 20 minutes at room temperature and methanol:acetic acid (3:1) fixation. Chromosomes were then GTG-banded.

2.3. FISH Studies

To identify the chromosomes unambiguously, FISH was performed after GTG-banding of the same metaphase spreads. As DNA probes we used five cosmids belonging to a YAC-contig overspanning the HMGI-C gene as described in the Legenda of FIG. 2. Three of these cosmids (27E12, 185H2, 142H1) are mapping to the third intron of HMGI-C, whereas cosmids 260C7 and 245E8 are localized at the 3' or the 5' end respectively. The slides were analyzed using a Zeiss (Zeiss, Oberkochem, Germany) Axioplan fluorescence microscope. Results were processed and recorded with the Power Gene Karyotyping System (PSI, Halladale, Great Britain). Rapid amplification of cDNA ends (RACE) was performed as described in one of the former examples.

3. Results

All four tumors showed the same type of cytogenetic abnormality, i.e. the presence of 47 chromosomes including two apparently normal chromosomes 12 and an additional derivative 14 der(14)t(12;14)(q14-15;q24) but without a corresponding der(12). Since the 3'–55' orientation of the HMGI-C is towards the centromere a single break within the HMGI-C gene would have led to the loss of its 5' part along with the loss of the der(12). We have therefore performed a series of FISH experiments in order to determine the breakpoints more precisely. Using the five cosmids 260C7, 27E12, 185H2, 142H1, and 245E8 hybridization signals of the same intensity were observed at both normal chromosomes 12 and at the additional der(14). The FISH results revealed that in all four cases chromosomal breakpoints were located 5' of the HMGI-C gene.

The breakpoint assignment in all four cases 5' of the HMGI-C gene fits well with the results of the RACE-PCR. In addition to the normal HMGI-C transcripts we were able to detect aberrant transcripts in all three tumors. Sequences showed that they were not derived from chromosome 14 but from intron 3 of HMGI-C probably due to cryptic splice sites. However, the RACE results revealed that there was indeed HMGI-C expression in all four cases.

Example 11

Re-differentiation of Leukemic Cells

1. Introduction

Expression of the HMGI-C gene is frequently strongly elevated in a wide variety of tumors, solid tumors as well as leukemias. It was speculated that the HMGI-C protein might play a key role in transformation of cells. This example shows that expression of the HMGI-C gene can be strongly reduced by expressing antisense HMGI-C sequences and that reduction of HMGI-C levels in tumor cells results in reversion of the transformed phenotype. Thus the expression or administration of antisense molecules can be successfully applied therapeutically.

2. Materials and Methods 2.1. Tumor Cell Lines

Tumor cell lines were generated from a primary malignant salivary gland tumor and a primary breast carcinoma. Cell lines were established as described by Kazmierczak, B., Thode, B., Bartnitzke, S., Bullerdiek, J. and Schloot, W., "Pleomorphic adenoma cells vary in their susceptibility to SV40 transformation depending on the initial karytotype.", Genes Chrom. Cancer 5:35–39 (1992).

2.2. Assay of the Transformed State

Soft agar colony assays were performed as described by Macpherson and Montagnier, "Agar suspension culture for the selective assays of cells transformed by polyoma virus." Virology 23, 291–294 (1964).

Salivary gland and breast tumor cells were propagated in TC199 culture medium with Earle's salts, supplemented with 20% fetal bovine serum (GIBCO), 200 IU/ml penicillin, and 200 µg/ml streptomycin.

Tumorigenicity of the transfected salivary gland (AD64) and breast cell lines was tested by injecting cells subcutaneously into athymic mice.

2.3. Transfection Assay

Transfections were performed using various protocols, namely:

1. The calcium phosphate procedure of Graham and Van der Eb ("A new technique for the assay of the infectivity of human adenovirus." Virology 52, 456–467 (1973) ).

2. Lipofection: Transfections were carried out using liposome-mediated DNA transfer (lipofectamine, GibcoBRL) according to the guidelines of the manufacturer.

2.4. Antisense Constructs

Sense and antisense constructs of the HMGI-C gene were obtained by inserting human HMGI-C CDNA sequences in both the sense and antisense orientation in expression vectors under the transcriptional control of various promoter contexts, e.g. the long terminal repeat of Moloney murine leukemia virus, a CMV promoter, or the early promoter of SV40. For example, the CMV/HMGI-C plasmid was constructed by cloning a human HMGI-C cDNA fragment containing all coding sequences of human HMGI-C in pRC/CMV (Invitogen) allowing expression under control of the human cytomegalovirus early promoter and enhancer, and selection for G418 resistance.

3. Results 3.1. Reversion of the Transformed Phenotype

Reversion of the transformed phenotype was observed in breast and salivary gland tumors cells after induction of antisense HMGI-C expression in these tumor cells. A strong reduction in tumorigenicity was observed as measured by soft agar colony assay and in vivo in athymic mice. Immunoprecipitation and Western blot analysis indicated a strong reduction of HMGI-C protein levels in the cells expressing antisense HMGI-C sequences. Therefore, this approach can be used therapeutically in tumors with involvement of HMGI-C.

Example 12

Animal Tumor Models Involving HMGI-C as Tools in in vivo Therapeutic Drug Testing On the basis of the acquired HMGI-C knowledge, animal tumor models can be developed as tools for in vivo drug testing. To achieve this objective (for instance for uterine leiomyoma), two approaches can be used, namely gene transfer (generation of transgenic animals) on the one hand and gene targeting technology (mimicking in vivo of a specific genetic aberration via homologous recombination in embryonic stem cells (ES cells)) on the other.

These technologies allow manipulation of the genetic constitution of complex living systems in specific and pre-designed ways. For extensive technical details, see B. Hogan, R. Beddington, F. Constantini, and E. Lacy; In: Manipulating the mouse embryo, A Laboratory Manual. Cold Spring Harbor Press, 1994; ISBN 0-87969-384-3.

To aim at the inactivation or mutation of the HMGI-C gene, specifically in selected cell types and selected moments in time, the recently described Cre/LoxP system can be used (Gu, H. et al. Deletion of a DNA polymerase β gene segment in T cells using cell type-specific gene targeting. Science 265, 103–106, 1994). The Cre enzyme is a recombinase from bacteriophage P1 whose physiological role is to separate phage genomes that become joined to one another during infection. To achieve so, Cre lines up short sequences of phage DNA, called loxP sites and removes the DNA between them, leaving one loxP site behind. This system has now been shown to be effective in mammalian cells in excising at high efficiency chromosomal DNA. Tissue-specific inactivation or mutation of a gene using this system can be obtained via tissue-specific expression of the Cre enzyme.

As an example, the development of animal model systems for uterine leiomyoma using a member of the MAG gene family will be outlined below, such that the models will be instrumental in in vivo testing of therapeutic drugs.

Two approaches may be followed:
a) in vivo induction of specific genetic aberrations as observed in human patients ((conditional) gene (isogenic) targeting approach); and
b) introduction of DNA constructs representative for the genetic aberrations observed in patients (gene transfer approach).

DNA constructs to be used in gene transfer may be generated on the basis of observations made in patients suffering from uterine leiomyoma as far as structure and expression control are concerned; e.g. HMGI-C fusion genes with various translocation partner genes, especially the preferential translocation partner gene of chromosome 14 located in the YAC contig represented by CEPH YACs 6C3, 89C5, 308H7, 336H12, 460A6, 489F4, 902F10, 952F5, 958C2, 961E1, and 971F5, truncated genes encoding basically the three DNA binding domains of HMGI-C, and complete HMGI-C or derivatives of HMGI-C under control of a strong promoter.

Example 13

The Preparation of Antibodies Against HMGI-C

One type of suitable molecules for use in diagnosis and therapy are antibodies directed against the MAG genes. For the preparation of rabbit polyclonal antibodies against HMGI-C use was made of the following three commercially available peptides:

(H-ARGEGAGQPSTSAQGQPAAPAPQKR) 8-Multiple Antigen Peptide (SEQ ID No:14)
(H-SPSKAAQKAEATGEK)8-MAPA (SEQ ID No: 15)
(H-PRKWPQQVVQKKPAQEE)8-MAP (SEQ ID No:16)

obtainable from Research Genetics Inc., Huntsville, Ala., USA. The polyclonal antibodies were made according to standard techniques.

TABLE I

ANALYSIS OF YAC CLONES

| CEPH-Code | Size (kb) | Landmark left | # | Landmark right | # | Chimeric |
|---|---|---|---|---|---|---|
| 183F3 | 715 | | | [RM10] | | YES (L + R) |
| 70E1 | 450 | RM29 | U27125 | | | ND |
| 95F1 | 390 | | | RM30 | U29054 | ND |
| 201H7 | 320 | RM23 | U29051 | RM14 | U29053 | ND |
| 185G12 | 320 | | | | | ND |
| 354B6 | 280 | | | | | YES (R) |
| 126G8 | 410 | | | | | ND |
| 258F11 | 415 | RM4 | U29052 | | | ND |
| 320F5 | 290 | RM5 | U29050 | RM21 | U29047 | ND |
| 234G11 | 475 | RM7 | U29046 | | | ND |
| 375H5 | 290 | | | | | ND |
| 262E10 | 510 | [RM15] | | RM16 | U29048 | YES (L) |
| 181C8 | 470 | | | RM26 | U29045 | ND |
| 107D1 | 345 | RM31 | U29043 | | | Nb |
| 499C5 | 320 | RM44 | U29044 | RM46 | U29337 | ND |
| 340B6 | 285 | | | | | ND |
| 532C12 | 400 | RM45 | U29041 | | | ND |
| 138C5 | 510 | [RM59] | | RM65 | U29342 | YES (L) |
| 145F2 | 490 | RM60 | U29030 | RM66 | U29340 | ND |
| 106E8 | 340 | RM57 | U29033 | RM63 | U29038 | ND |
| 55G1 | 365 | RM56 | U29031 | RM62 | U29039 | ND |
| 103G7 | 370 | RM85 | U29025 | RM60 | U29335 | ND |
| 295B10 | 295 | RM77 | U29035 | RM61 | U29026 | ND |
| 338C2 | 200 | RM78 | U29034 | RM82 | U29029 | ND |
| 391C12 | 160 | [RM79] | | RM83 | U29027 | YES (L) |
| 476A11 | 225 | [RM87] | | RM84 | U25032 | YES (L) |
| 138F3 | 460 | RM90 | U29028 | RM91 | U29019 | ND |
| 226E7 | 500 | RM48 | U29024 | RM54 | U29015 | ND |
| 499E9 | 375 | RM51 | U29016 | | | YES (R) |
| 312F10 | 580 | [RM50] | | RM69 | U29021 | YES (L) |
| 825G7 | 950 | | | | | ND |
| 34B5 | 315 | RM88 | U29020 | RM89 | U29013 | ND |
| 94A7 | 610 | | | | | YES (R) |
| 305B2 | 660 | | | | | YES (L) |
| 379H1 | 280 | RM204 | U29014 | RM105 | U29009 | ND |
| 444E6 | 350 | RM92 | U29017 | RM93 | U29010 | ND |
| 446H3 | 370 | RM94 | U29011 | RM95 | U29018 | ND |
| 403B12 | 380 | | | | | ND |
| 261E5 | 500 | RM102 | U29012 | RM103 | U26689 | ND |
| 78B11 | 425 | | | | | ND |
| 921B9 | 1670 | | | | | ND |
| 939H2 | 1750 | | | | | ND |
| 188H7 | 360 | | | | | ND |
| 142F4 | 390 | | | | | ND |
| 404E12 | 360 | | | | | ND |
| 164A3 | 375 | | | | | ND |
| 244B12 | 415 | RM106 | U29307 | RM107 | U29008 | ND |
| 275H4 | 345 | RM108 | U29004 | RM109 | U29005 | ND |
| 320F9 | 370 | | | | | ND |

TABLE I-continued

ANALYSIS OF YAC CLONES

| CEPH-Code | Size (kb) | Landmark left | # | Landmark right | # | Chimeric |
|---|---|---|---|---|---|---|
| 51F8 | 450 | | | | | ND |
| 242A2 | 160 | CH1 | U29005 | | | ND |
| 253H1 | 400 | | | | | ND |
| 303F11 | 320 | | | | | ND |
| 322C8 | 410 | | | CH2 | U29003 | ND |
| 208G12 | 370 | RM96 | U29002 | RM97 | U27125 | ND |
| 341C1 | 270 | RM98 | U26847 | RM99 | U27130 | ND |
| 354F1 | 270 | | | | | ND |
| 452E1 | 270 | CH5 | U27136 | | | ND |
| 41A2 | 310 | | | | | ND |
| 934D2 | 1370 | | | | | ND |
| 944E8 | 1290 | | | CH8 | U23792 | ND |
| 2G11 | 350 | | | | | ND |
| 755D7 | 1390 | | | | | YES (L) |
| 365A12 | 370 | | | | | ND |
| 803C2 | 1080 | | | | | ND |
| 210C1 | 395 | RM70 | U28998 | RM86 | U27133 | ND |
| 433C8 | 360 | RM73 | U29000 | RM76 | U27132 | ND |
| 402A7 | 500 | RM41 | U28994 | [RM42] | | YES (R) |
| 227E8 | 465 | RM53 | U27134 | RM55 | U28995 | ND |
| 329F9 | 275 | RM72 | U28793 | RM75 | U28997 | ND |
| 261E5 | 395 | [RM71] | | RM74 | U28995 | YES (L) |
| 348F2 | 370 | | | [RM136] | | YES (R) |
| 6F3 | 320 | RM35 | U27140 | RM36 | U27141 | |
| 59F12 | 430 | RM34 | U26794 | RM33 | U27131 | |
| 255H3 | 300 | | | RM40 | U28999 | |

YAC clonees were isolated from CEPH YAC libraries as described in Materials and Methods. ND: not detected by methods used. Landmarks not mapping within the 6 Mb contig have been bracketed. GenBank accession numbers are given (#).

TABLE II

PCR Primers (SEQ ID Nos: 17—18)

| STS name (STS 12-) | Nucleotide sequence 5'—3' | Product size (bp) | $T_{ann}$ (°C.) |
|---|---|---|---|
| CH1 | TGGGACTAACGGATTTTCAA TGTGGTTCATTCATGCATTA | 213 | 58 |
| CH2 | TCCATCATCATCTCAAAACA CTCTACCAAATGGAATAAACAG | 145 | 58 |
| CH5 | GCAGCTCAGGCTCCTTCCCA TGGCTTCCTGAAACGCGAGA | 143 | 58 |
| CH8 | TCTCCACTGCTTCCATTCAC ACACAAAACCACTGGGGTCT | 147 | 58 |
| CH9 | CAGCTTTGGAATCAGTGAGG CCTGGGGAAGAGGAGTAAAG | 262 | 58 |
| RM1 | GAGCTTCCTATCTCATCC ATGCTTGTGTGTGAGTGG | 308 | 60 |
| RM4 | TTTGCTAAGCTAGGTGCC AGCTTCAAGACCCATGAG | 236 | 60 |
| RM5 | CAGTTCTGAGACTGCTTG TAATAGCAGGGACTCAGC | 324 | 60 |
| RM7 | CTTGTCTCATTCTTTTAAAGGG CACCCCTTTTTAGATCCTAC | 538 | 58 |
| RM13 | GAATGTTCATCACAGTGCTG AATGTGAGGTTCTGCTGAAG | ±500 | 58 |
| RM14 | TTCTCATGGGGTAAGGACAG AAAGCTGCTTATATAGGGAATC | 158 | 58 |
| RM16 | CCTTGGCTTAGATATGATACAC GCTCTTCAGAAATATCCTATGG | 252 | 58 |
| RM21 | CCTTAGCAGTTGCTTGTCTG TCGTCACAGGACATAGTCAC | 290 | 58 |
| RM26 | TCTATGGTATGTTATACAAGATG CAGTGAGATCCTGTCTCTA | 102 | 58 |
| RM31 | TCTGTGATGTTTTAAGCCACTTAG AATTCTGTGTCCCTGCCACC | 239 | 56 |
| RM33 | ATTCTTCCTCACCTCCCACC AATCTGCAGAGAGGTCCAGC | ±600 | 60 |
| RM34 | AATTCTCCATCTGGGCCTGG GAACGCTAAGCATGTGGGAG | ±600 | 60 |
| RM36 | CTCCAACCATGGTCCAAAAC GACCTCCAGTGGCTCTTTAG | 296 | 60 |

TABLE II-continued

PCR Primers (SEQ ID Nos: 17—18)

| STS name (STS 12-) | Nucleotide sequence 5'—3' | Product size (bp) | $T_{ann}$ (° C.) |
|---|---|---|---|
| RM46 | ACCATCAGATCTGGCACTGA TTACATTGGAGCTGTCATGC | 241 | 57 |
| RM48 | TCCAGGACATCCTGAAAATG AGTATCCTGCACTTCTGCAG | 391 | 58 |
| RM51 | GATGAACTCTGAGGTGCCTTC TCAAACCCAGCTTTGACTCC | 311 | 60 |
| RM53 | GTCTTCAAAACGCTTTCCTG TGGTTTGCATAATGGTGATG | 333 | 60 |
| RM60 | TACACTACTCTGCAGCACAC TCTGAGTCAATCACATGTCC | 94 | 58 |
| RM69 | CTCCCCAGATGATCTCTTTC CGGTAGGAAATAAAGGAGAG | 236 | 58 |
| RM72 | TATTTACTAGCTGGCCTTGG CATCTCAGGCACACACAATG | 101 | 62 |
| RM76 | ATTCAGAGAAGTGGCCAAGT GGGATAGGTCTTCTGCAATC | 496 | 58 |
| RM85 | TCCAACAATACTGAGTGACC TCCATTTCACTGTAGCACTG | 435 | 58 |
| RM86 | GTAATCAACCATTCCCCTGA AAAATAGCTGGTATGGTGGC | 203 | 56 |
| RM90 | ACTGCTCTAGTTTTCAAGGA AATTTACCTGACAGTTTCCT | 257 | 58 |
| RM93 | GCATTTGACGTCCAATATTG ATTCCATTGGCTAACACAAG | 347 | 60 |
| RM98 | GCAAAACTTTGACTGAAACG CACAGAGTATCGCACTGCAT | 356 | 58 |
| RM99 | AAGAGATTTCCCATGTTGTG CTAGTGCCTTCACAAGAACC | 240 | 58 |
| RM103 | AATTCTTGAGGGGTTCACTG TCCACACTGAGAGCTTTTCA | 199 | 60 |
| RM108 | GTGGTTCTGTACAGCAGTGG TGAGAAAATGTCTGCCAAAT | 439 | 60 |
| RM110 | GCTCTACCAGGCATACAGTG ATTCCTAGCATCTTTTCACG | 328 | 58 |
| RM111 | ATATGCATTAGGCTCAACCC ATCCCACAGGTCAACATGAC | 312 | 58 |
| RM130 | ATCCTTACATTTCCAGTGGCATTCA CCCAGAAGACCCACATTCCTCAT | 336 | 58 |
| RM131 | TTTTAAGTTTCTCCAGGGAGGAGAC AATAGGCTCTTTGGAAAGCTGGAGT | 226 | 58 |
| RM132 | TCTCAGCTTAATCCAAGAAGGACTTC GGCATATTCCTCAACAATTTATGCTT | 376 | 58 |
| RM133 | TGGAGAAGCTATGGTGCTTCCTATG TGACAAATAGGTGAGGGAAAGTTGTTAT | 225 | 58 |
| EST01096 | TCACACGCTGAATCAATCTT CAGCAGCTGATACAAGCTTT | 188 | 58 |
| IFNG | TGTTTTCTTTCCCGATAGGT CTGGGATGCTCTTCGACCTC | 150 | 52 |
| Rap1B | CCATCCAACATCTTAAATGGAC CAGCTGCAAACTCTAGGACTATT | 149 | 58 |

STSs were isolated as described in Materials and Methods, or retrieved from literature for EST01096, IFNG, and Rap1B.

TABLE 3

Genome Data Base accession numbers (D-numbers) of the various sequences indicated in FIG. 1.

Genome Data Base (41 rows affected)

| per | locus_symbol | per | per_gdb_id | locus | locus_gdb_id |
|---|---|---|---|---|---|
| CH1-lower/CH1-upper | D12S1484 | CH1-lower/CH1-upper | G00-595-292 | D12S1484 | G00-595-415 |
| CH2-lower/CH2-upper | D12S1485 | CH2-lower/CH2-upper | G00-595-295 | D12S1485 | G00-595-416 |
| CH5-lower/CH5-upper | D12S1486 | CH5-lower/CH5-upper | G00-595-298 | D12S1486 | G00-595-417 |
| CH8-lower/CH8-upper | D12S1487 | CH8-lower/CH8-upper | G00-595-301 | D12S1487 | G00-595-418 |
| CH9-lower/CH9-upper | D12S1488 | CH9-lower/CH9-upper | G00-595-304 | D12S1488 | G00-595-419 |
| EH2-lower/EH2-upper | D12S1489 | EH2-lower/EH2-upper | G00-595-307 | D12S1489 | G00-595-420 |
| EH3-lower/EH3-upper | D12S1490 | EH3-lower/EH3-upper | G00-595-310 | D12S1490 | G00-595-421 |
| EH4-lower/EH4-upper | D12S1491 | EH4-lower/EH4-upper | G00-595-313 | D12S1491 | G00-595-422 |
| RM13-lower/RM13-upper | D12S1492 | RM13-lower/RM13-upper | G00-595-316 | D12S1492 | G00-595-423 |

TABLE 3-continued

Genome Data Base accession numbers (D-numbers) of the various sequences indicated in FIG. 1.

Genome Data Base (41 rows affected)

| per | locus_symbol | per | per_gdb_id | locus | locus_gdb_id |
|---|---|---|---|---|---|
| RM14-lower/RM14-upper | D12S1493 | RM14-lower/RM14-upper | G00-595-319 | D12S1493 | G00-595-424 |
| RM16-lower/RM16-upper | D12S1494 | RM16-lower/RM16-upper | G00-595-322 | D12S1494 | G00-595-425 |
| RM25-lower/RM25-upper | D12S1507 | RM26-lower/RM26-upper | G00-595-325 | D12S1495 | G00-595-426 |
| RM26-lower/RM26-upper | D12S1495 | RM-29-lower/RM29-upper | G00-595-328 | D12S1496 | G00-595-427 |
| RM31-lower/RM31-upper | D12S1497 | RM31-lower/RM31-upper | G00-595-331 | D12S1497 | G00-595-428 |
| RM33-lower/RM33-upper | D12S1498 | RM33-lower/RM33-upper | G00-595-334 | D12S1498 | G00-595-429 |
| RM34-lower/RM34-upper | D12S1499 | RM34-lower/RM34-upper | G00-595-337 | D12S1499 | G00-595-430 |
| RM36-lower/RM36-upper | D12S1500 | RM36-lower/RM36-upper | G00-595-340 | D12S1500 | G00-595-431 |
| RM46-lower/RM46-upper | D12S1501 | RM46-lower/RM46-upper | G00-595-343 | D12S1501 | G00-595-432 |
| RM48-lower/RM48-upper | D12S1502 | RM48-lower/RM48-upper | G00-595-346 | D12S1502 | G00-595-433 |
| RM51-lower/RM51-upper | D12S1503 | RM51-lower/RM51-upper | G00-595-349 | D12S1503 | G00-595-434 |
| RM53-lower/RM53-upper | D12S1504 | RM53-lower/RM53-upper | G00-595-352 | D12S1504 | G00-595-435 |
| RM60-lower/RM60-upper | D12S1505 | RM60-lower/RM60-upper | G00-595-355 | D12S1505 | G00-595-436 |
| RM69-lower/RM69-upper | D12S1506 | RM69-lower/RM69-upper | G00-595-358 | D12S1506 | G00-595-437 |
| RM72-lower/RM72-upper | D12S1508 | RM25-lower/RM25-upper | G00-595-361 | D12S1507 | G00-595-438 |
| RM76-lower/RM76-upper | D12S1509 | RM72-lower/RM72-upper | G00-595-364 | D12S1508 | G00-595-439 |
| RM85-lower/RM85-upper | D12S1510 | RM76-lower/RM76-upper | G00-595-367 | D12S1509 | G00-595-440 |
| RM86-lower/RM86-upper | D12S1511 | RM85-lower/RM85-upper | G00-595-370 | D12S1510 | G00-595-441 |
| RM90-lower/RM90-upper | D12S1512 | RM86-lower/RM86-upper | G00-595-373 | D12S1511 | G00-595-442 |
| RM93-lower/RM93-upper | D12S1513 | RM90-lower/RM90-upper | G00-595-376 | D12S1512 | G00-595-443 |
| RM98-lower/RM98-upper | D12S1514 | RM93-lower/RM93-upper | G00-595-379 | D12S1513 | G00-595-444 |
| RM99-lower/RM99-upper | D12S1515 | RM98-lower/RM98-upper | G00-595-382 | D12S1514 | G00-595-445 |
| RM-29-lower/RM29-upper | D12S1496 | RM99-lower/RM99-upper | G00-595-385 | D12S1515 | G00-595-446 |
| RM103-lower/RM103-upper | D12S1516 | RM103-lower/RM103-upper | G00-595-388 | D12S1516 | G00-595-447 |
| RM108-lower/RM108-upper | D12S1517 | RM108-lower/RM108-upper | G00-595-391 | D12S1517 | G00-595-448 |
| RM110-lower/RM110-upper | D12S1518 | RM110-lower/RM110-upper | G00-595-394 | D12S1518 | G00-595-449 |
| RM111-lower/RM111-upper | D12S1519 | RM111-lower/RM111-upper | G00-595-397 | D12S1519 | G00-595-450 |
| RM121-lower/RM121-upper | D12S1520 | RM121-lower/RM121-upper | G00-595-400 | D12S1520 | G00-595-451 |
| RM130-lower/RM130-upper | D12S1521 | RM130-lower/RM130-upper | G00-595-403 | D12S1521 | G00-595-452 |
| RM131-lower/RM131-upper | D12S1522 | RM131-lower/RM131-upper | G00-595-406 | D12S1522 | G00-595-453 |
| RM132-lower/RM132-upper | D12S1523 | RM132-lower/RM132-upper | G00-595-409 | D12S1523 | G00-595-454 |
| RM133-lower/RM133-upper | D12S1524 | RM133-lower/RM133-upper | G00-595-412 | D12S1524 | G00-595-455 |

TABLE 4

FISH mapping of chromosome 12 breakpoints in primary benign solid tumors to a subregion of MAR

| Tumor type | Breakpoint with MAR | Fraction of tumors with breakpoints within main breakpoint cluster region* |
|---|---|---|
| Lipoma | 6/6 | 6/6 |
| Pleomorphic salivary gland adenoma | 7/7 | 5/7 |
| Uterine leiomyoma | 7/8 | 7/8 |
| Hamartoma of the breast | 1/1 | 1/1 |
| Fibroadenoma of the breast | 1/1 | 1/1 |
| Hamartoma of the lung | 8/8 | 8/8 |
| Angiomyxoma | 1/1 | 1/1 |

*Tumor samples were collected and analyzed at the histopathology and cytogenetics facilities of the University of Bremen. A mixture of cosmid clones 27E12 and 142H1 was used as molecular probe in FISH analysis.

TABLE 5

| Clone | Tumor/ Cell Line | Diversion Point | Nuc. Sequences (10b) | Chrom. RACE | sources cytogen. | poly(A) signal | #A's | primer- set |
|---|---|---|---|---|---|---|---|---|
| | | exon/intron 3 (DBD3) | (SEQ ID NOS: 103–159) TAGGAAATGG\|GTGAGTAATA | | | | | |
| pCH108 | Li-14/SV40 | after DBD3 | TAGGAAATGG\|AATACTCTGG | 12\|? | 3q27 | AGTAAA | 26 | ? |
| pCH113 | Li-538/SV40 | after DBD3 | TAGGAAATGG\|AATACTCTGG | 12\|? | 3q27 | AGTAAA | 26 | ? |
| pCH234 | #2528-90 | after DBD3 | TAGGAAATGG\|AATACTCTGG | 12\|? | | (AGTAAA) | 17 | |
| pCH259 | #2344-94 | after DBD3 | TAGGAAATGG\|AATACTCTGG | 12\|? | | ? | | ? |
| pCH260 | #2344-94 | after DBD3 | TAGGAAATGG\|AATACTCTGG | 12\|? | | ? | | ? |

TABLE 5-continued

| Clone | Tumor/Cell Line | Diversion Point | Nuc. Sequences (10b) | Chrom. RACE | sources cytogen. | poly(A) signal | #A's | primer-set |
|---|---|---|---|---|---|---|---|---|
| pCH148 | #192 | after DBD3 | TAGGAAATGG\|CCTACTATTG | 12\|N.T.[2] | 12 | AATAAA | 18 | — |
| pCH245 | #568 92 | after DBD3 | TAGGAAATGG\|CCTACTATTG | 12\| | | AATAAA | 17 | |
| pCH247 | #568 92 | after DBD3 | TAGGAAATGG\|CCTACTATTG | 12\| | | AATAAA | 53 | |
| pCH261 | #2344-94 | after DBD3 | TAGGAAATGG\|CCTACTATTG | 12\| | | AATAAA | 27 | |
| pCH212 | #1321-89 | after DBD3 | TAGGAAATGG\|GGAAGTGTGA | 12\| | | AATAAA | 26 | |
| pCH213 | #1321-89 | after DBD3 | TAGGAAATGG\|GGAAGTGTGA | 12\| | | ? | | |
| pCH228 | #1321-89 | after DBD3 | TAGGAAATGG\|GGAAGTGTGA | 12\| | | N.D. | 13 | |
| pCH216 | #1321-89 | after DBD3 | TAGGAAATGG\|AACACAGGAC | 12\| | | AATAAA | 12 | |
| pCH229 | #2100-89 | after DBD3 | TAGGAAATGG\|AACACAGGAC | 12\| | | AATAAA | 15 | |
| pCH232 | #2100-89 | after DBD3 | TAGGAAATGG\|AACACAGGAC | 12\| | | AATAAA | 25 | |
| pCH177 | #2100-89 | after DBD3 | TAGGAAATGG\|GTTTAATATT | 12\|3 | 2p21 | AATAAA | 29 | 177 |
| pCH191 | #367 | after DBD3 | TAGGAAATGG\|GTTTAATATT | 12\|3 | | AATAAA | 49 | (177) |
| pCH210 | #25 | after DBD3 | TAGGAAATGG\|AAGAAGGCAG | 12\| | | AATAAA | 22 | |
| pCH211 | #837-88 | after DBD3 | TAGGAAATGG\|AAGAAGGCAG | 12\| | | AATAAA | 22 | |
| pCH230 | #837-88 | after DBD3 | TAGGAAATGG\|TAGGAGGTAG | 12\| | | AATAAA | 27 | |
| pCH233 | #2100-89 | after DBD3 | TAGGAAATGG\|TAGGAGGTAG | 12\| | | AATAAA | 18 | |
| pCH111 | #2100-89 | after DBD3 | TAGGAAATGG\|GGTGGCCATT | 12\|3 | 3q27 | AATAAA | 33 | 111-AB |
| pCH112 | Li-501/SV40 | after DBD3 | TAGGAAATGG\|GGTGGCCATT | 12\|3 | 3q27 | AATAAA | 33 | 111-AB |
| pCH114 | Li-501/SV40 | after DBD3 | TAGGAAATGG\|GACAATCTAC | 12\|12 | 3q27 | (CATAAA) | 24 | 115-AB |
| pCH115 | Li-538/SV40 | after DBD3 | TAGGAAATGG\|GACAATCTAC | 12\|12 | 3q27 | (CATAAA) | 24 | 115-AB |
| pCH147 | Li-538/SV40 | after DBD3 | TAGGAAATGG\|GTACAGAAGA | 12\|9 | 12 | AATAAA | 23 | 147 |
| pCH153 | #192 | after DBD3 | TAGGAAATGG\|GGGCATTCAG | 12\|N.T.[1] | 4p13 | AATAAA | 22 | — |
| pCH169 | #203 | after DBD3 | TAGGAAATGG\|GCAGTCTGTA | 12\|? | 8q22 | AATAAA | 26 | 169 |
| pCH172 | #294 | after DBD3 | TAGGAAATGG\|TCTGTATCCT | 12\|8q22-qter | 8q22 | AATAAA | 24 | 172-AB |
| pCH173 | #294 | after DBD3 | TAGGAAATGG\|ACACACTTCC | 12\|? | 8q22 | AATAAA | 12 | 173-AB |
| pCH174 | #294 | after DBD3 | TAGGAAATGG\|ATATTATCGA | 12\|8q22 | 8q22 | AATAAA | 15 | 174-AB |
| pCH110 | LM-30-1/SV40 | after DBD3 | TAGGAAATGG\|GAGGAGTTTT | 12\|12 | 14 | AATAAA | 17 | 110-AB |
| pCH164 | Myo168.1 | after DBD3 | TAGGAAATGG\|TAACACACGA | 12\|? | x | (GATAAA) | 30 | 164-AB |
| pCH165 | Myo168.1 | after DBD3 | TAGGAAATGG\|TTACTGCTC | 12\|14 | x | (AATAAC) | 30 | 165-AB |
| pCH168 | Myo196.4 | after DBD3 | TAGGAAATGG\|GCTGGAGTGC | 12\|12 | 14 | (CATAAA) | 23 | 168 |
| pCH209 | #837-88 | after DBD3 | TAGGAAATGG\|GTCTCCTCCC | 12\| | | AATAAA | 19 | |
| pCH217 | #2100-89 | after DBD3 | TAGGAAATGG\|TTTNTCTCTT | 12\| | | ATTAAA | 22 | |
| pCH219 | #2100-89 | after DBD3 | TAGGAAATGG\|AGTCCAAGAA | 12\| | | (CATAAA) | 17 | |
| pCH220 | #3391-90 | after DBD3 | TAGGAAATGG\|CCAAACTCTG | 12\| | | AATAAA | 28 | |
| pCH223 | #CG592 | after DBD3 | TAGGAAATGG\|CTCCAGAAAC | 12\| | | AATAAA | 24 | |
| pCH226 | #3100-88 | after DBD3 | TAGGAAATGG\|AACTTCTTGA | 12\| | | ? | ? | |
| pCH231 | #2100-89 | after DBD3 | TAGGAAATGG\|GAATGTCAGA | 12\| | | AATAAA | 24 | |
| pCH246 | #568-92 | after DBD3 | TAGGAAATGG\|CCTGGAAGCT | 12\| | | AATAAA | ? | |
| pCH248 | #568-92 | after DBD3 | TAGGAAATGG\|ATGGAGTCTC | 12\| | | AATAAA | 40 | |
| pCH249 | #2617-93 | after DBD3 | TAGGAAATGG\|ATGGAGTCTC | 12\| | | AATAAA | 19 | |
| pCH251 | #2617-93 | after DBD3 | TAGGAAATGG\|ATGGAGTCTC | 12\| | | AATAAA | 19 | |
| pCH250 | #2617-93 | after DBD3 | TAGGAAATGG\|TTCCAGATAC | 12\| | | N.D. | 13 | |
| pCH252 | #2617-93 | after DBD3 | TAGGAAATGG\|TTCCAGATAC | 12\| | | N.D. | 13 | |
| | | exon/intron 4 (SPACER) | GCCTGCTCAG\|GTAAGACATA | | | | | |
| pCH109 | LM30.1/SV40 | after spacer | GCCTGCTCAG\|GTCAATGTTG | 12\|12 | 14 | AATAAA | 17 | 109-AB |
| pCH238 | #2778-93 | after spacer | GCCTGCTCAG\|GTCAATGTTG | 12\|12 | 14 | AATAAA | 17 | 109-AB |
| pCH244 | #2162-91 | after spacer | GCCTGCTCAG\|GTCAATGTTG | 12\|12 | 14 | AATAAA | 17 | 109-AB |
| pCH254 | #2776-93 | after spacer | GCCTGCTCAG\|GTCAATGTTG | 12\|12 | 14 | AATAAA | 17 | 109-AB |
| pCH203 | #2528-90 | after spacer | GCCTGCTCAG\|TCCTGGTACC | 12\|(NF1") | | N.D. | 19 | |
| pCH199 | #CG575 | after spacer | GCCTGCTCAG\|TCCTGGTACC | 12\|(NF1") | 12 | (AATAAA) | 15 | |
| pCH222 | #CG575 | after spacer | GCCTGCTCAG\|TCCTGGTACC | 12\|(NF1") | 12 | N.D. | 16 | |
| pCH206 | #CG575 | after spacer | GCCTGCTCAG\|TCCTGGTACC | 12\|(NF1") | 12 | (AATAAA) | 16 | |
| pCH175 | #275 | after spacer | GCCTGCTCAG\|TCTTTCGAT | 12\|? | 1 | AATAAA | 15 | 175-AB |
| pCH237 | #2617-93 | after spacer | GCCTGCTCAG\|TCTTTCGAT | 12\|? | | AATAAA | 16 | |
| pCH207 | #2540-87 | after spacer | GCCTGCTCAG\|AATTACCTCT | 12\| | 12 | AATAAA | 18 | |
| pCH239 | #2344-94 | after spacer | GCCTGCTCAG\|AATTACCTCT | 12\| | | AATAAA | 18 | |
| pCH116 | Li-14/SV40 | after spacer | GCCTGCTCAG\|GACTGACTCA | 12\|12 | 3 | (AATAGA) | 17 | 116-AB |
| pCH184 | Myo163.1 | after spacer | GCCTGCTCAG\|TATTCCTGAA | 12\|12 | 14 | AATAAA | 19 | 184-AB |
| pCH208 | #2540-87 | after spacer | GCCTGCTCAG\|GTCAATGTTG | 12\| | 12 | AATAAA | 47 | |
| pCH224 | #2540-87 | after spacer | GCCTGCTCAG\|AATTACCTCT | 12\| | 12 | AATAAA | 15 | |
| pCH201 | #837-88 | after spacer | GCCTGCTCAG\|AATTACCTCT | 12\| | | AATAAA | 15 | |
| pCH236 | #2162-91 | after spacer | GCCTGCTCAG\|GCTTTTTCAA | 12\| | | AATAAA | 28 | |
| pCH243 | #2162-91 | after spacer | GCCTGCTCAG\|GTTAAGAAAC | 12\| | | ? | ? | |
| pCH227 | #183-89 | after spacer | GCCTGCTCAG\|GNCTGACTAC | 12\| | 12 | (AATAGA) | 14 | |

TABLE 5-continued

| Clone | Tumor/ Cell Line | Diversion Point | Nuc. Sequences (10b) | Chrom. RACE | sources cytogen. | poly(A) signal | #A's | primer-set |
|---|---|---|---|---|---|---|---|---|
| 3'-untranslated region (various positions) | | | | | | | | |
| pCH193 | #58 | within 3'-UTR | TATCCTTTCA\|AAGTCAAGAG | 12\|8q22-qter | 8q24 | AATAAA | 23 | (195-AB) |
| pCH194 | #58 | within 3'-UTR | TATCCTTTCA\|AAGTCAAGAG | 12\|8q22-qter | 8q24 | AATAAA | 34 | (195-AB) |
| pCH195 | #192 | within 3'-UTR | TATCCTTTCA\|AAGTCAAGAG | 12\|8 | 12 | AATAAA | 23 | 195-AB |
| pCH196 | #192 | within 3'-UTR | TATCCTTTCA\|AAGTCAAGAG | 12\|8 | 12 | AATAAA | >17 | 195-AB |
| pCH189 | Myo192.1 | within 3'-UTR | TCTTTCCACT\|del CCCTGT | 12\|12 | | — | — | |
| | | | ATACCACTTA\|TTTTAAAACA | 12\|N.T.[1] | 2/3 | AATAAA | 23 | — |
| pCH117 | Ad-312/SV40 | within 3'-UTR | TTGCCATGGT\|AATCTGAAAT | 12\|1p22 | 1p22 | ? | | 117-AB |
| pCH253 | #2617-93 | within 3'-UTR | CACTTTCATC\|ATATGGCAAG | 12\| | | N.D. | | |
| pCH264 | #568-92 | within 3'-UTR | ATAAGGACTA\|TCAGGCATCA | 12\| | | (AGTAAA) | 19 | |
| pCH270 | #2528-90 | within 3'-UTR | NCTTGTNAGC\|TAGAGATTAG | 12\| | | N.D. | 4 | |

N.T.: NOT TESTABLE
N.T.[1]: LENGTH OF ECTOPIC SEQUENCE DOES NOT ALLOW DEVELOPMENT OF PRIMER-SET
N.T.[2]: ECTOPIC SEQUENCE IS MAINLY COMPOSED OF REPETIVE SEQUENCES
N.D.: NOT DETECTED

Legends to the Figures

FIG. 1

Long range physical map of a 6 Mb region on the long arm of human chromosome 12 deduced from a YAC contig consisting of 75 overlapping CEPH YAC clones and spanning the chromosome 12q breakpoints as present in a variety of benign solid tumors. The long range physical map of the composite genomic DNA covered by the YAC inserts is represented by a black solid line with the relative positions of the various restriction sites of rare cutting enzymes indicated. DNA regions in which additional cutting sites of a particular restriction enzyme might be found are indicated by arrows. Polymorphic restriction endonuclease sites are marked with asterisks. DNA markers isolated and defined by others are depicted in green. DNA markers obtained by us are shown in boxes and are labelled by an acronym (see also Table I and II). The relative positions of these DNA markers in the long range physical map are indicated and those corresponding to particular YAC ends are linked to these by a dotted line. Some of the DNA markers have been assigned to a DNA interval and this is indicated by arrows. For DNA markers in white boxes STSs have been developed and primer sets are given in Table II. For those in yellow boxes, no primer sets were developed. The DNA intervals containing RAP1B, EST01096, or IFNG are indicated. Where applicable, D number assignments are indicated. Below the long range physical map, the sizes and relative positions of the overlapping YAC clones fitting within the consensus long range restriction map are given as solid blue lines. DNA regions of YAC inserts not fitting within the consensus long range restriction map are represented by dotted blue lines. CEPH microtiter plate addresses of the YAC clones are listed. The orientation of the YAC contig on chromosome 12 is given. The relative positions of ULCR12 and MAR are indicated by red solid lines labelled by the corresponding acronyms. Accession numbers of STSs not listed in Table I: CH9 (#U27142); RM1 (#U29049); RM110 (#U29022); RM111 (#U29023); RM130 (#U27139); RM131 (#U29001); RM132 (#U27138); RM133 (#U27137). Restriction sites: B: BssHII; K: KspI (=SacII); M: MluI; N: NotI; P: PvuI; Sf: SfiI.

FIG. 2

Contig of overlapping cosmids, long range restriction and STS map spanning a segment of MAR of about 445 kb. Contig elements are numbered and defined in the list below. LL12NC01-derived cosmid clones are named after their microtiter plate addresses. GenBank accession numbers (#) of the various STSs are listed below. STSs are given in abbreviated form; e.g. RM33 instead of STS 12-RM33. A 40 kb gap between STSs "K" and "O" in the cosmid contig was covered by λ clones (clones 38 and 40) and PCR products (clones 37 and 39). The orientation of the contig on the long arm of chromosome 12 is given as well as the order of 37 STSs (indicated in boxes or labelled with encircled capital letters). The slanted lines and arrows around some of the STS symbols at the top of the figure mark the region to which the particular STS has been assigned. It should be noted that the cosmid contig is not scaled; black squares indicate STSs of cosmid ends whereas the presence of STSs corresponding to internal cosmid sequences are represented by dots. Long range restriction map: Bs: BssHII; K: KspI (=SacII); M: MluI; N: NotI; P: PvuI; Sf: SfiI. At the bottom of the figure, detailed restriction maps are shown of those regions containing exons (boxes below) of the HMGI-C gene. Noncoding sequences are represented by open boxes and coding sequences by black boxes. Estimated sizes (kb) of introns are as indicated. The relative positions of the translation initiation (ATG) and stop (TAG) codons in the HMGI-C gene as well as the putative poly-adenylation signal are indicated by arrows. Detailed restriction map: B: BamHI; E: EcoRI; H: HindIII. MAR: Multiple Aberration Region; DBD: DNA Binding Domain.

| | |
|---|---|
| 1 = 140A3 | 30 = 46G3 |
| 2 = 202A1 | 31 = 59A1 |
| 3 = 78F11 | 32 = 101D8 |
| 4 = 80C9 | 33 = 175C7 |
| 5 = 109B12 | 34 = 185H2 |

-continued

| | |
|---|---|
| 6 = 148C12 | 35 = 189C2 |
| 7 = 14H6 | 36 = 154B12 |
| 8 = 51F8 | 37 = pRM150 |
| 9 = 57C3 | 38 = pRM144 |
| 10 = 86A10 | 39 = PKXL |
| 11 = 142G8 | 40 = pRM147 |
| 12 = 154A10 | 41 = 128A2 |
| 13 = 163D1 | 42 = 142H1 |
| 14 = 42H7 | 43 = 204A10 |
| 15 = 113A5 | 44 = 145E1 |
| 16 = 191H5 | 45 = 245E8 |
| 17 = 248E4 | 46 = 154F9 |
| 18 = 33H7 | 47 = 62D8 |
| 19 = 50D7 | 48 = 104A4 |
| 20 = 68B12 | 49 = 184A9 |
| 21 = 124D8 | 50 = 56C2 |
| 22 = 128A7 | 51 = 65E6 |
| 23 = 129F9 | 52 = 196E1 |
| 24 = 181C1 | 53 = 215A8 |
| 25 = 238E1 | 54 = 147G8 |
| 26 = 69B1 | 55 = 211A9 |
| 27 = 260C7 | 56 = 22D8 |
| 28 = 156A4 | 57 = 116B7 |
| 29 = 27E12 | 58 = 144D12 |
| A = STS 12-EM12 (#U27145) | I = STS 12-CH12 (#U27153) |
| Q = STS 12-RM120 (#U27161) | B = STS 12-EM30 (#U27146) |
| J = STS 12-EM10 (#U27154) | R = STS 12-RM118 (#U27162) |
| C = STS 12-EM14 (#U27147) | K = STS 12-EM37 (#U27155) |
| S = STS 12-RM119 (#U27163) | D = STS 12-EM31 (#U27148) |
| L = STS 12-RM146 (#U27156) | T = STS 12-EM2 (#U27164) |
| E = STS 12-CH11 (#U27149) | M = STS 12-RM145 (#U27157) |
| U = STS 12-EM4 (#U27165) | F = STS 12-EM18 (#U27150) |
| N = STS 12-RM151 (#U27158) | V = STS 12-EM3 (#U27166) |
| G = STS 12-EM11 (#U27151) | O = STS 12-EM16 (#U27159) |
| W = STS 12-EM15 (#U27167) | H = STS 12-CH10 (#U27152) |
| P = STS 12-EM1 (#U27160) | X = STS 12-EM17 (#U27168) |
| STS 12-CH5 (#U27136) | STS 12-CH9 (#U27142) |
| STS 12-RM33 (#U27131) | STS 12-RM53 (#U27134) |
| STS 12-RM76 (#U27132) | STS 12-RM86 (#U27133) |
| STS 12-RM98 (#U26647) | STS 12-RM99 (#U27130) |
| STS 12-RM103 (#U26689) | STS 12-RM130 (#U27139) |
| STS 12-RM132 (#U27138) | STS 12-RM133 (#U27137) |
| STS 12-RM151 (#U27158) | |

FIG. 3

Schematic representation of FISH mapping data obtained for tumor cell lines with chromosome 12q13–q15 aberrations, including 8 lipoma, 10 uterine leiomyoma, and 8 pleomorphic salivary gland adenoma cell lines in consecutive experiments following our earlier FISH studies. Probes used included phage clones pRM144 (corresponding STSs: RM86 and RM130) and pRM147 (RM151), and cosmid clones 7D3 or 152F2 (RM103), 154F9 (CH9), 27E12 (EM11), 211A9 (RM33), 245E8 (RM53), 185H2 (RM76), 202A1 (RM98), 142H1 (RM99), 154B12 (RM132), and 124D8 (RM133). The DNA interval between RM33 and RM98 is estimated to be about 445 kb. Dots indicate conclusive FISH experiments that were performed on metaphase chromosomes of a particular cell line using as molecular probe, a clone containing the STS given in the box above. Solid lines indicate DNA intervals to which a breakpoint of a particular cell line was concluded to be mapping. Open triangles indicate deletions observed during FISH analysis. Open circles indicate results of FISH experiments on metaphase chromosomes of Li-501/SV40 cells with hybridization signals on a cytogenetically normal chromosome 3. The positions of chromosome 12 breakpoints of tumor cell lines mapping outside MAR are indicated by arrows. The molecularly cloned breakpoints of LM-30.1/SV40 and LM-608/SV40 are indicated by asterisks. Breakpoints in various uterine leiomyoma cell lines splitting cosmid 27E12 (EM11) are indicated by "across".

FIG. 4

3'-RACE product (SEQ ID Nos. 160–161) comprising the junction between part of the HMGI-C gene and part of the LPP gene. The primers used and the junction are indicated. The cDNA synthesis was internally primed and not on the true poly(A) tail.

FIG. 5

Partial cDNA sequence of the LPP gene (SEQ ID NO:162).

FIG. 6

Amino acid sequence of the LPP gene (SEQ ID NO: 163). LIM domains are boxed. The breaking point is indicated with an arrow.

FIG. 7

Nucleotide sequence of HMGI-C (U28749) (SEQ ID NO:164 ). The transcription start site indicated as proposed by Manfioletti et al. [67] was arbitrarily chosen as a start site. The sequence contains the complete coding sequence.

FIG. 8

Gel of PCR products obtained as described in Example 5.

References

1. Sreekantaiah, C., Leong, S. L. P., Karakousis, C. P., McGee, D. L., Rappaport, W. D., Villar, H. V., Neal, D., Fleming, S., Wankel, A., Herrington, P. N., Carmona, R. and Sandberg, A. A. (1991). cytogenetic profile of 109 lipomas. Cancer Res. 51: 422–433.
2. Nilbert, M. and Heim, S. (1990). Uterine leiomyoma cytogenetics. Genes Chrom. Cancer 2: 3–13.
3. Pandis, N., Heim, S., Willen, H., Bardi, G., Floderus, U. M., Mandahl, N. and Mitelman, F. (1991). Chromosome analysis of 96 uterine leiomyomas. Cancer Genet. Cytogenet. 55: 11–18.
4. Sandros, J., Stenman, G. and Mark, J. (1990). Cytogenetic and molecular observations in human and experimental salivary gland tumours. Cancer Genet. Cytogenet. 44: 153–167.
5. Bullerdiek, J., Wobst, G., Meyer-Bolte, K., Chilla, R., Haubrich, J., Thode, B. and Bartnitzke, S. (1993). Cytogenetic subtyping of 220 salivary gland pleomorphic adenomas: correlation to occurrence, histological subtype, and in vitro cellular behavior. Cancer Genet. Cytogenet. 65: 27–31.
6. Walter, T. A., Xuan Fan, S., Medchill, M. T., Berger, C. S., Decker, H-J. H. and Sandberg, A. A. (1989). Inv(12) (p11.2q13) in an endometrial polyp. Cancer Genet. Cytogenet. 41: 99–103.
7. Vanni, R., Dal Cin, P., Marras, S., Moerman, P., Andrtia, A., Valdes, E., Deprest, J., and Van den Berghe, H., (1993). Endometrial polyp: Another benign tumor characterized by 12q13–q15 changes. Cancer Genet. Cytogenet. 68: 32–33.
8. Mandahl, N., Orndal, C., Heim, S., Willen, H., Rydholm, A., Bauer, H. C. F. and Mitelman, F. (1993). Aberrations of chromosome segment 12q13–q15 characterize a subgroup of hemangiopericytomas. Cancer 71: 3009–3013.
9. Mandahl, N., Heim, S., Arheden, K., Rydholm, A., Willen, H. and Mitelman, F. (1989). Chromosomal rearrangements in chondromatous tumors. Cancer 65:242–248.
10. Bridge, J. A., Persons, D. L., Neff, J. R. and Bhatia, P. (1992). Clonal karyotypic aberrations in enchondroma. Cancer Detect. Prev. 16: 215–219.
11. Hirabayashi, Y., Yoshida, M. A., Ikeuchi, T., Ishida, T., Kojima, T. Higaki, S., Machinami, R. and Tonomura, A. (1992). Chromosome rearrangements at 12q13 in two cases of chondrosarcomas. Cancer Genet. Cytogenet. 60: 35–40.
12. Mandahl, N., Willen, H., Rydholm, A. and Mitelman, F. (1993). Rearrangement of band q13 on both chromosomes 12 in a periosteal chondroma. Genes Chrom. Cancer 6: 121–123.
13. Dal Cin, P., Kools, P., De Jonge, I., Moerman, Ph., Van de Ven W., Van den Berghe H. (1993a). Rearrangement of 12q14–q15 in Pulmonary Chondroid Hamartoma. Genes Chrom. Cancer, 8, 131–133.
14. Schoenberg Fejzo, M., Yoon, S. J., Montgomery, K. T., Rein, M. S., Weremowicz, S., Krauter, K. S., Dorman, T. E., Fletcher, J. A., Mao, J., Moir, D. T., Kucherlapati, R. S., and Morton, C. C. (1995). Identification of a YAC spanning the translocation breakpoints in uterine leiomyomata, pulmonary chondroid hamartoma and lipoma. Physical mapping of the 12q14–q15 breakpoint region in uterine leiomyomata. Genomics 26: 265–275.
15. Birdsal, S. H., MacLennan, K. A. and Gusterson, B. A. (1992). t(6;12)(q23;q13) and t(10;16)(q22;p11) in a phyllodes tumor of the breast. Cancer Genet. Cytogenet. 60: 74–77.
16. Rohen, C., Bonk, U., Staats, B., Bartnizke, S. and Bullerdiek, J. (1993). Two human breast tumors with translocations involving 12q13–q15 as the sole cytogenetic abnormality. Cancer Genet. Cytogenet., 69: 68–71.
17. Jenkins, R. B., Kimmell, D. W., Moertel, C. A., Schulz, C. A., Menezes, R. M., Scheihauer, B., Kelly, P. J. and Dewald, G. W. (1989). Recurrent cytogenetic abnormalities in 80 gliomas. Cytogenet. Cell Genet. 51: 1019.
18. Noguera, R., Llombart-Bosch, A., Lopez-Gines, C., Carda, C. and Fernandez, Cl'. (1989). Giant-cell tumor of bone, stage II, displaying translocation t(12;19) (q13;q13). Virchows Archiv A Pathol. Anat. 415: 377–382.
19. Turc-Carel, C., Limon, J., Dal Cin, P., Rao, U., Karakousis, C., and Sandberg, A. A. (1986). Cytogenetic studies of adipose tissue tumours. II. Recurrent reciprocal translocation t(12;16) (q13;p11in myxoid liposarcomas. Cancer Genet. Cytogenet. 23: 291–299.
20. Rodriguez, E., Sreekantaiah, C., Reuter, V. E., Motzer, R. J. and Chaganti, R. S. K. (1992). t(12;22)(q13;q13) and trisomy 8 are nonrandom aberrations in clear-cell sarcoma. Cancer Genet. Cytogenet. 64: 107–110.
21. Reeves, B. R., Fletcher, C. D. M. and Gusterson, B. A. (1992). Translocation t(12;22)(q13;q13) is a nonrandom rearrangement in clear cell sarcoma. Cancer Genet. Cytogenet. 64: 101–103.
22. Fletcher, J. A. (1992). Translocation (12;22)(q1 3–14;q12) is a nonrandom aberration in soft-tissue clear-cell sarcoma. Genes Chrom. Cancer 5: 184.
23. Roberts, P., Browne, C. F., Lewis, I. J., Bailey, C. C., Spice, R. D., Williams, J. and Batcup, G. (1992). 12q13 Abnormality in rhabdomyosarcoma. A nonrandom Occurrence? Cancer Genet. Cytogenet. 60: 135–140.
24. Schoenmakers, H. F. P. M., Mols, R., Wanschura, S., Kools, P. F. J., Geurts, J. M. W., Bartnitzke, S., Bullerdiek, J., Van den Berghe, H., and Van de Ven, W. J. M. (1994b). Identification, molecular cloning and characterization of the chromosome 12 breakpoint cluster region of uterine leiomyomas. Genes Chrom. & Cancer. 11: 106–118.
25. Van de Ven, W. J. M., Schoenmakers, H. F. P. M., Wanschura, S., Kazmierczak, B., Kools, P. F. J., Geurts, J. M. W., Bartnitzke, S., Van den Berghe, H., and Bullerdiek, J. (1995). Molecular characterization of MAR, a multiple aberration region on human chromosome segment 12q13–q15 implicated in various solid tumors. Genes Chrom. & Cancer. 12: 296–303. (Enclosed as "ANNEX 1")
26. Casalone, r. et al. (1991) Cytogenetic analysis reveals clonal proliferation of smooth muscle cells in etherosclerotic plaques. Hum. Gen. 87, 139–143.
27. Vanni, R. et al. (1990) Atherosclerotic plaque as a benign tumor. Cancer Genet. Cytogenet. 47, 273–274.
28. Giancotti, V. et al. Elevated levels of a specific class of nuclear phosphoproteins in cells transformed with ras and v-mos oncogenes and by co-transfection with c-myc and polyoma middle T genes. EMBO J. 6, 1981–1987 (1987).
29. Warburton, D., Gersen, S., Yu, M-T., Jackson, C., Handelin, B. and Housman, D. (1990). Monochromosomal rodent-human hybrids from microcell fusion of human lymphoblastoid cells containing an inserted dominant selectable marker. Genomics 6: 358–366.
30. Schoenmakers, H. F. P. M., Kools, P. F. J., Kazmierczak, B., Bullerdiek, J., Claussen, U., Horsthemke, B., Van den Berghe, H. and Van de Ven, W. J. M. (1993). Isolation of a somatic cell hybrid retaining the der(16)t(12;16) (q13;p11.2) from a myxoid liposarcoma cell line. Cytogenet. Cell Genet. 62: 159–161.
31. Rychlik, W. and Rhoads, R. E. (1989). A computer program for choosing optimal oligonucleotides for filter hybridization, sequencing and in vitro amplification of DNA. Nucleic Acids Res. 17: 8543–8551.
32. Verbeek, J. S., Roebroek, A. J. M., Van den Ouweland, A. M. W., Bloemers, H. P. J. and Van de Ven, W. J. M. (1985). Human c-fms proto-oncogene: comparative analysis with an abnormal allele. Mol. Cell. Biol. 5: 422–426.
33. Montgomery, K. T., LeBlanc, J. M., Tsai, P., McNinch, J. S., Ward, D. C., De Jong, P. J., Kucherlapati, R., and Krauter, K.S. (1993). Characterization of two chromosome 12 cosmid libraries and development STSs from cosmids mapped by FISH. Genomics 17: 682–693.
34. Sambrook, J., Fritsch, E. F. and Maniatis, T. (1989). Molecular Cloning: A Laboratory Manual. Cold Spring Harbor Laboratory Press, Cold Spring Harbor, N.Y.
35. Dal Cin, P., Kools, P., Sciot, R., De Wever, I., Van Damme, B., Van de Ven, W. and Van den Berghe, H. (1993b). Molecular cytogenetic characterization of ring chromosomes in adipose tissue tumors. Cancer Genet. Cytogenet., 68, 85–90.
36. Kievits, T., Dauwerse, J. G., Wiegant; J., Devilee, P., Breuning, M. H., Cornelisse, C. J. and van Ommen, G., Pearson, P. L. (1990). Rapid subchromosomal localization of cosmids by nonradioactive in situ hybridization. Cytogenet. Cell Genet. 53: 134–136.
37. Albertsen, H. M., Abderrahim, H., Cann, H. M., Dausset, J., L Paslier, D., and Cohen, D. (1990). Construction and characterization of a yeast artificial chromosome library containing seven haploid human genome equivalents. Proc. Natl. Acad. Sci. USA 87: 4256–4260.
38. Chumakov, I., Rigault, P., Guillou, S., Ougen, P., Billaut, A., Guasconi, G., Gervy, P., LeGall, I., Soularue, P., Grinas, L., Bougueleret, L., Bellanné-Chantelot, C., Lacroix, B., Barillot, E., Gesnouin, P., Pook, S., Vaysseix, G., Frelat, G., Schmitz, A., Sambucy, J. L., Bosch, A., Estivill, X., Weissenbach, J., Vignal, A., Riethman, —H., Cox, D., Patterson, D., Gardiner, K., Hattori, M., Sakaki, Y., Ichikawa, H., Ohki, M., L Paslier, D., Heilig, R., Antonarakis, S., and Cohen, D. (1992). Continuum of overlapping clones spanning the entire human chromosome 21q. Nature 359: 380–387.
39. Schoenmakers, H. F. P. M., Kools, P. F. J., Mols, R., Kazmierczak, B., Bartnitzke, S., Bullerdiek, J., Dal Cin, P., De Jong, P. J., Van den Berghe, H. and Van de Ven, W. J. M. (1994a). Physical mapping of chromosome 12q breakpoints in lipoma, pleomorphic salivary gland adenoma, uterine leiomyoma, and myxoid liposarcoma. Genomics 20: 210–222.

40. Chu, G., Vollrath, D. and Davis, R. W. (1986) Separation of large DNA molecules by contour-clamped homogeneous electric fields. Science 234: 1582–1585.
41. Geurts, J., Schoenmakers H. F. P. M., Mols, R., and Van de Ven, W. J. M. (1994). Improved procedure for rapid isolation and sequencing of DNA insert termini in yeast artificial chromosomes. Meth. Mol. Cell. Biol., 4: 257–265.
42. Kools, P. F. J., Wanschura, S., Schoenmakers, E. F. P. M., Geurts, J. W. M., Mols, R., Kazmierczak, B., Bullerdiek, J., Van den Berghe, H. and Van de Ven, W. J. M. (1995). Identification of the chromosome 12 translocation breakpoint region of a pleomorphic salivary gland adenoma with t(1;12) (p22;q15) as the sole cytogenetic abnormality. Cancer Genet. Cytogenet., 79: 1–7. (Enclosed as "ANNEX 2")
43. Kazmierczak, B., Wanschura, S., Rosigkeit, J., Meyer-Bolte, K., Uschinsky, K., Haupt, R., Schoenmakers, E. F. P. M., Bartnitzke, S., Van de Ven, W. J. M. and Bullerdiek, J. (1995). Molecular characterization of 12q14–q15 rearrangements in three pulmonary chondroid hamartomas. Cancer Res., in press. 44. Kucherlapati, R., Craig, I., and Marynen, P. (1994).
Report of the second international workshop on human chromosome 12 mapping 1994. Cytogenet. Cell Genet. 67: 246–276
45. Gyapay, G., Morissette, J., Vignal, A., Dib, C., Fizames, C., Millasseau, P., Marc, S., Bernardi, G., Lathrop, M. and Weissenbach, J. (1994). The 1993–94 Genethon human genetic linkage map. Nature Genetics 7: 246–339.
46. Ulinowski, Z., Taylor, K., Griffin, D., Delhanty, J. and Wolfe, J. (1991). D12S56: a highly polymorphic locus on human chromosome 12q14. Ann. Hum. Genet. 55: 279–282.
47. Trent, J. M., Olson, S. and Lawn, R. M. (1982) Chromosomal localization of human leukocyte, fibroblast, and immune interferon genes by means of in situ hybridization. Proc. Natl. Acad. Sci. U.S.A. 79: 7809–7813.
48. Pizon, V., Lerosey, I., Chardin, P. and Tavitian, A. (1988). Nucleotide sequence of a human cDNA encoding a ras-related protein (rap1B). Nucleic Acids Res. 16: 7719.
49. Adams, M. D., Dubnick, M., Kerlavage, A. R., Moreno, R., Kelley, J. M., Utterback, T. R., Nagle, J. W., Fields, C., and Venter, J. C. (1992). Sequence identification of 2,375 human brain genes. Nature 355: 632–634.
50. Cohen, D., Chumakov, I., and Weissenbach, J. (1993). A first-generation physical map of the human genome. Nature 366: 698–701.
51. Larsen, F., Gundersen, G., and Prydz, H. (1992a). Choice of enzymes for mapping based on CpG islands in the human genome. GATA 9: 80–85.
52. Larsen, F., Gundersen, G., Lopez, R., and Prydz, H. (1992b). CpG islands as gene markers in the human genome. Genomics 13: 1095–1107.
53. Lavia, P., MacLeod, D., and Bird, A. (1987). Coincident start sites for divergent transcripts at randomly selected CPG-rich island of mouse. EMBO J. 6: 2773–2779.
54. Kazmierczak, B., Bartnitzke, S., Hartl, M. & Bullerdiek, J. In vitro transformation by the SV40 "early region" of cells from a human benign salivary gland tumor with a 12q13–q15 rearrangement. Cytogenet. Cell Genet. 53, 37–39 (1990).
55. Albertsen, H. M., Adderrahim, H., Cann, H. M., Dausset, J., Le Paslier, D. & Cohen, D. Construction and characterization of a yeast artificial chromosome library containing seven haploid human genome equivalents. Proc. natl. Acad. Sci. U.S.A. 87, 4256–4260 (1990).
56. Chumakov, I. et al. Continuum of overlapping clones spanning the entire human chromosome 21q. Nature 359, 380–387 (1992).
57. Green, E. D. & Olson, M. V. Systematic screening of yeast artificial-chromosome libraries using the polymerase chain reaction. Proc. natl. Acad. Sci. U.S.A. 87, 1213–1217 (1990).
58. Montgomery, K. T. et al. Characterization of two chromosome 12 cosmid libraries and development of STSs from cosmids mapped by FISH. Genomics 17, 682–693 (1993).
59. Geurts, J. M. W., Schoenmakers E. F. P. M., Mols, R. & Van de Ven, W. J. M. Improved procedure for rapid isolation and sequencing of DNA insert termini in yeast artificial chromosomes. Meth. Mol. Cell. Biol. 4, 257–265 (1994).
60. Nelson, D. L. et al. Alu polymerase chain reaction: A method for rapid isolation of human-specific sequences from complex DNA sources. Proc. natl. Acad. Sci. U.S.A. 86, 6686–6690 (1989).
61. Rychlik, W. & Rhoads, R. E. A computer program for choosing optimal oligonucleotides for filter hybridization, sequencing and in vitro amplification of DNA. Nucl. Acids Res. 17, 8543–8551 (1989).
62. Feinberg, A. P. & Vogelstein, B. A technique for radiolabelling DNA restriction endonuclease fragments to high specific activity. Anal. Biochem. 132, 6–13 (1984).
63. Smith, M. W., Holmsen, A. L., Wei, Y. H., Peterson, M. & Evans, G. A. Genomic sequence sampling: a strategy for high resolution sequence-based physical mapping of complex genomes. Nature Genetics 7, 40–47 (1994).
64. Altschul, S. F., Gish, W., Miller, W., Myers, E. W. & Lipman, D. J. Basic local alignment search tool. J. Mol. Biol. 215, 403–410 (1990).
65. Patel, U. A. et al. Expression and cDNA cloning of human HMGI-C phosphoprotein. Biochem. Biophys. Res. Commun. 201, 63–70 (1994).
66. Bustin, M., Lehn, D. A. & Landsman, D. Structural features of the HMG chromosomal proteins and their genes. Biochim. Biophys. Acta 1049, 231–243 (1990).
67. Manfioletti, G. et al. cDNA cloning of the HMGI-C phosphoprotein, a nuclear protein associated with neoplastic and undifferentiated phenotypes. Nucl. Acids Res. 19, 6793–6797 (1991).
68. Wagner, M. J., Ge, Y., Siciliano, M. & Wells, D. E. A hybrid cell mapping panel for regional localization of probes to human chromsome 8. Genomics 10, 114–125 (1991).
69. Friedman, M., Holth, L. T., Zoghbi, H. Y. & Reeves, R. organization, inducible-expression and chromosome localization of the human HMG-I(Y) nonhistone protein gene. Nucl. Acids Res. 21, 4259–4267 (1993).
70. Rabbitts, T. H. Chromosomal translocations in human cancer. Nature 372, 143–149 (1994).
71. Yang-Yen, H. F. & Rothblum, L. I. Purification and characterization of a high-mobility-group-like DNA-binding protein that stimulates rRNA synthesis in vitro. Mol. Cell. Biol. 8, 3406–3414 (1988).
72. Reeves, R., Langan, T. A. & Nissen, M. S. Phosphorylation of the DNA-binding domain of nonhistone high-mobility group I protein by cdc2 kinase: reduction of binding affinity. Proc. natl. Acad. Sci. U.S.A. 88, 1671–1675 (1991).
73. Thanos, D. & Maniatis, T. The high mobility group protein HMGI(Y) is required for NF-B-dependent virus induction of the human IFN-$\beta$ gene. Cell 71, 777–789 (1992).

74. Du, W. & Maniatis, T. The high mobility group protein HMGI(Y) can stimulate or inhibit DNA binding of distinct transcriptional factor ATF-2 isoforms. Proc. natl. Acad. Sci. U.S.A. 91, 11318–11322 (1994).
75. Aizawa, S., Nishino, H., Saito, K., Kimura, K., Shirakawa, H. & Yoshida, M. Stimulation of transcription in cultured cells by high mobility group protein 1: Essential role of the acidic carboxy-terminal region. Biochemistry 33, 14690–14695 (1994).
76. Mitelman F (1994): Catalog of Chromosome Aberrations in Cancer. 4th ed., New York, Wiley-Liss.
77. Miles, J. H., Zonanna, J., Mcfarlane, J., Aleck, K. A. & Bawle, E. Macrocephaly with hamartomas: Bannayan-Zonana syndrome. Am. J. Med. Genet. 19, 225–234 (1984).
78. Crawford, A. W., Pino, J. D. & Beckerie, M. C. J. Cell. Biol., 124, 117–127 (1994).
79. Schmeichel, K. L. & Beckerie, M. C. Cell, 79, 211–219 (1994).
80. Sanchez-Garcia, I. & Rabbitts, T. (1994) The LIM domain: a new structural motif found in zinc-finger-like proteins. Trends in Genetics 10(9), 315–320.
81. Compton, J. (1991). Nucleic acid sequence-based amplification. Nature 350, 91–92.

Annex 1

Genes, Chromosome & Cancer 12:296–303 (1995)

Molecular Characterization of MAR, a Multiple Aberration Region on Human Chromosome Segment 12q13–q15 Implicated in Various Solid Tumors Wim J. M. Van de Ven, Eric F. P. X. Schoen-akers, Sylke Wanschura, Bernd Razmierczak, Patrick F. J. Kools, Jan M. W. Geurts, Sabine Bartnitzke, Herman Van den Berghe, and Jörn Bullerdiek Center for Human Genetics, University of Leuven, Belgium (W. J. M. V. D. V., E. F. P. M. S., P. F. J. K., J. W. M. G., H. V. D. B.);

Center for Human Genetics, University of Bremen, Germany (S. W., B. K., S. B., J. B.).

Chromosome arm 12q breakpoints in seven cell lines derived from primary pleomorphic salivary gland adenomas were mapped by FISH analysis relative to nine DNA probes. These probes all reside in a 2.8 Mb genomic DNA region of chromosome segment 12q13–q15 and correspond to previously published sequence-tagged sites (STS). Their relative positions were established on the basis of YAC cloning and long range physical and STS content mapping. The 12q breakpoints of five of the cell lines were found to be mapping within three different subregions of the 445 kb DNA interval that was recently defined as the uterine leiomyoma cluster region of chromosome 12 breakpoints (ULCR12) between STS RM33 and RM98. All seven breakpoints appeared to map within the 1.7 Mb DNA region between STS RM36 and RM103. Furthermore, the chromosome 12 breakpoints of three primary pleomorphic salivary gland adenomas were also found to be mapping between RM36 and RM103. Finally, FISH analysis of two lipoma cell lines with 12q13–q15 aberrations pinpointed the breakpoints of these to relatively small and adjacent DNA segments which, as well as those of two primary lipomas, appeared to be located also between RM36 and RM103. We conclude from the observed clustering of the 12q breakpoints of the three distinct solid tumor types that the 1.7 Mb DNA region of the long arm of chromosome 12 between RM36 and RM103 is a multiple aberration region which we designate MAR. Genes Chromosom Cancer 12:296–303 (1995). © 1995 Wiley-Liss, Inc.

Introduction

Chromosome translocations involving region q13–15 of chromosome 12 have been observed in a wide variety of solid tumors (Mitelman, 1991). In subgroups of cytogenetically abnormal uterine leiomyomas (Nilbert and Heim, 1990; Pandis et al., 1991), pleomorphic salivary gland adenomas (Sandros et al., 1990; Bullerdiek et al., 1993), and benign adipose tissue tumors (Sreekantaiah et al., 1991), 12q13–q15 aberrations are frequently observed. In a recent study (Schoenmakers et al., 1994b), we identified and molecularly characterized ULCR12, the uterine leiomyoma cluster region of chromosome 12 breakpoints. In the present study, we focus on the chromosome arm 12q breakpoints in pleomorphic adenoma of the salivary glands, a benign epithelial tumor originating from the major or minor salivary glands. It is the most common type of salivary gland tumor and accounts for almost 50% of all neoplasms in these organs. About 85% of the tumors are found in the parotid gland, 10% in the minor salivary glands, and 5% in the submandibular gland (Seifert et al., 1986). Although many of these adenomas appear to have a normal karyotype, cytogenetic studies have also revealed recurrent specific chromosome anomalies (Sandros et al., 1990; Bullerdiek et al., 1993). Besides chromosome 8 aberrations, often translocations with a breakpoint in 8q12 with, as the most common aberration, a t(3;8) (p21;q12), aberrations of chromosome 12, usually translocations involving 12q13–q15, are also frequent. Non-recurrent clonal abnormalities have also been described. The frequent involvement of region 12q13–q15 in distinct solid tumor types suggests that this chromosomal region harbors gene(s) that might be implicated in the evolution of these tumors. Molecular cloning of the chromosome 12 breakpoints of these tumors and characterization of the junction fragments may therefore lead to the identification of such gene(s).

On the basis of fluorescence in situ hybridization (FISH) data, we have previously reported that the chromosome 12 breakpoints in a number of cell lines derived from primary pleomorphic salivary gland adenomas (Kazmierczak et al., 1990; Schoenmakers et al., 1994a), are located on the long arm of chromosome 12 in the interval between loci D12S19 and D12S8 (Schoenmakers et al., 1994a). This DNA interval has been estimated to be about 7 cM (Keats et al., 1989; Craig et al., 1993). The interval containing the chromosome 12 breakpoints of these tumor cells was narrowed further by showing that all breakpoints mapped distally to the CHOP gene, which is directly affected by the characteristic t(12;16) translocation in myxoid liposarcomas (Aman et al., 1992; Crozat et al., 1993; Rabbitts et al., 1993) and is located between D12S19 and D12S8. In more recent studies (Kools et al., 1995), the chromosome 12 breakpoint of pleomorphic salivary gland adenoma cell line Ad-312/SV40 was pinpointed to a DNA region between sequence-tagged sites (STSs) RM110 and RM111, which is less than 165 kb in size. FISH evaluation of the chromosome 12 breakpoints of the other pleomorphic salivary gland adenoma cell lines indicated that they must be located proximally to the one in Ad-312/SV40, at a distance of more than 800 kb (Kools et al., 1995). These results pointed towards a possible dispersion of the chromosome 12 breakpoints over a relatively large genomic region on the long arm of chromosome 12.

Here, we report physical mapping of the chromosome 12 breakpoints in pleomorphic salivary gland adenoma cells from primary tumors as well as established tumor cell lines. The karyotypic anomalies observed in the cells were all different but always involved region q13–q15 of chromosome 12. Using DNA probes between D12S8 and CHOP, which corresponded to sequence-tagged sites (STSs) of a long-range physical map of a 6 Mb DNA region and were obtained during chromosome walking experiments, we performed FISH experiments and defined more precisely a major chromosome 12 breakpoint cluster region of pleomorphic salivary gland adenoma. This breakpoint cluster region appeared to overlap with ULCR12. Furthermore, we tested whether 12q13–q15 breakpoints of lipomas might also map within the same region as those of pleomorphic salivary gland adenoma and uterine leiomyoma.

Materials and Methods

Primary Solid Tumors and Derivative Cell Lines.

Primary solid tumors including pleomorphic salivary gland adenomas, lipomas, and uterine leiomyomas were obtained from the University Clinics in Leuven, Belgium (Dr. I. De Wever); in Bremen, Germany (Dr. R. Chille); in Krefeld, Germany (Dr. J. Haubrich); and from the Institute of Pathology in Göteborg, Sweden (Dr. G. Stenman). For cell culturing and subsequent FISH analysis, tumor samples were finely minced, treated for 4–6 hours with 0.8% collagenase (Boehringer, Mannheim, FRG), and processed further for FISH analysis according to routine procedures.

Human tumor cell lines used in this study included the previously described pleomorphic salivary gland adenoma cell lines Ad-211/SV40, Ad-248/SV40, Ad-263/SV40, Ad-295/SV40, Ad-302/SV40, AD-366/SV40, and Ad-386/SV40 (Kazmierczak et al., 1990; Schoenmakers et al., 1994a) and the lipoma cell lines Li-14/SV40 (Schoenmakers et al., 1994a) and recently developed Li-538/SV40. Chromosome 12 aberrations found in these cell lines are listed in Table 1. Cells were propagated in TC199 culture medium with Earle's salts supplemented with 20% fetal bovine serum.

TABLE 1

Chromosome 12 Abberrations in Primary Human Solid Tumors and Cell Lines*

| | Aberration |
|---|---|
| Cell lines | |
| Ad-211/SV40 | t(8; 12)(q21; q13–q15) |
| Ad-248/SV40 | ins(12; 6)(q15; q16q21) |
| Ad-263/SV40 | inv(12)(q15q24.1) |
| Ad-295/SV40 | t(8; 12; 18)(p12; q14; p11.2) |
| Ad-302/SV40 | t(7; 12)(q31; q14) |
| Ad-366/SV40 | inv(12)(p13q15) |
| Ad-386/SV40 | t(12; 14)(q13–q15; q13–q15) |
| Li-14/SV40 | t(3; 12)(q28; q13) |
| Li-538/SV40 | t(3; 12)(q27; q14) |
| LM-5.1/SV40 | t(12; 15)(q15; q24) |
| LM-30.1/SV40 | t(12; 14)(q15; q24) |
| LM-65/SV40 | t(12; 14)(q15; q24) |
| LM-67/SV40 | t(12; 14)(q13–q15; q24) |
| LM-100/SV40 | t(12; 14)(q15; q24) |
| LM-605/SV40 | ins(12; 11)(q14; q21qter) |
| LM-608/SV40 | t(12; 14)(q15; q24) |
| LM-609/SV40 | t(12; 14)(q15; q24) |
| Primary tumors | |
| Ad-386 | t(12; 14)(q15; q11.2) |
| Ad-396 | t(3; 12) |
| Ad-400 | t(12; 16) |
| Li-166 | t(12; 12) |
| Li-167 | t(3; 12)(q28; q14–q15) |
| LM-163.1 | t(12; 14)(q14; q24) |
| LM-163.2 | t(12; 14)(q14–q24) |
| LM-1683 | t(X; 12)(q22; q15) |
| LM-192 | t(2; 3; 12)(q35; p21; q14) |
| LM-196.4 | t(12; 14)(q14; q24) |

*Ad, pleomorphic salivary gland adenoma; Li, lipoma; uterine leiomyoma.

DNA probes.

In the context of a human genome project focusing on the long arm of chromosome 12, we isolated cosmid clones cRM33, cRM36, cRM51, cRM69, cRM72, cRM76, cRM98, cRM103, and cRM133, from chromosome 12-specific arrayed cosmid library LLNL12NC01 (Montgomery et al., 1993). Further details of these cosmid clones have been reported at the Second International Chromosome 12 Workshop (1994) and will be described elsewhere (Kucherlapati et al., 1994). Briefly, initial screenings were performed using a PCR-based screening strategy (Green and Olson, 1990), followed by filter hybridization analysis as the final screening step, as previously described (Schoenmakers et al., 1994b). The cosmid clones were isolated using STSs derived from YAC clones. STSs were obtained upon rescue of YAC insert-ends using a methodology involving vectorette-PCR followed by direct solid phase fluorescent sequencing of the PCR products (Geurts et al., 1994) or from inter-Alu PCR (Nelson et al., 1989). Cosmid clones were grown and handled according to standard procedures (Sambrook et al., 1989).

Cosmid clone cPK12qter, which maps to the telomeric region of the long arm of chromosome 12 (Kools et al., 1995) was used as a reference marker.

Chromosome Preparations and Fluorescence In Situ Hybridization.

Metaphase spreads of the pleomorphic salivary gland adenoma cell lines or normal human lymphocytes were prepared as described before (Schoenmakers et al., 1993). To unambiguously establish the identity of chromosomes in the FISH experiments, FISH analysis was performed after GTG-banding of the same metaphase spreads. GTG-banding was performed essentially as described by Smit et al. (1990). In situ hybridizations were carried out according to a protocol described by Kievits et al. (1990) with some minor modifications (Kools et al., 1994; Schoenmakers et al., 1994b). Cosmid and YAC DNA was labelled with biotin-11-dUTP (Boehringer Mannheim) or biotin-14-dATP (BRL, Gaithersburg) as described before (Schoenmakers et al., 1994b). Specimens were analyzed on a Zeiss Axiophot fluorescence microscope using a FITC filter (Zeiss). Results were recorded on Scotch (3M) 640 asa film.

Results

FISH Mapping of 12q Breakpoints in Cell Lines of Pleomorphic Salivary Gland Adenoma.

In previous studies (Schoenmakers et al., 1994a), we mapped the chromosome 12 breakpoints in a number of pleomorphic adenomas of the salivary glands relative to various DNA markers and established that these were all located proximally to locus D12S8 and distal to the CHOP gene. This region is somewhat smaller than the 7 cM region encompassed by linkage loci D12S8 and D12S19 (Keats et al., 1989). Using YAC cloning, a long range physical/STS map has been constructed covering most of that 7 cM region, as recently reported (Kucherlapati et al., 1994). Furthermore, numerous genomic clones (cosmid clones) have been isolated and their relative positions within this map established (Kucherlapati et al., 1994). Nine of these cosmids, including cRM33, cRM36, cRM51, cRM69, cRM72, cRM76, cRM98, cRM103, and cRM133, were used in FISH studies to establish the positions of the chromosome 12 breakpoints of the seven cell lines derived from pleomorphic adenomas of the salivary glands (Table 1). The relative mapping order of these nine cosmid clones, which cover a genomic region on the long arm of chromosome 12 of about 2.8 Mb, is indicated in FIG. 1 and the results of FISH studies with the various cosmid probes are schematically summarized in the same figure. As an illustration, FISH results obtained with metaphase cells of cell line Ad-295/SV40 using cRM76 and cRM103 as probes are shown in FIG. 2. It should be noted that for the identification of chromosomes, pre-FISH GTG-banding was used routinely. On the basis of such banding, hybridization signals could be assigned conclusively to chromosomes of known identity; this was of major importance for cases with cross- or background hybridization signals, as these were occasionally observed. When GTG-banding in combination with FISH analysis provided inconclusive results, either because of weak hybridization signals or rather vague banding, FISH experiments were performed with cosmid clone cPK12qter (Kools et al., 1995) as a reference probe.

FISH analysis of metaphase chromosomes of each of the seven pleomorphic salivary gland adenoma cell lines with cosmid cRM103 revealed that this cosmid mapped distal to the chromosome 12 breakpoints of all seven cell lines studied here. Metaphase chromosomes of six of the seven cell lines were also tested with probe cRM69 and, in two cases, with cRM51. The results of the latter experiments were always consistent with those obtained with cRM103. Similar FISH analysis with cRM36 as probe indicated that this probe mapped proximal to all the breakpoints. These results were always consistent with those obtained for five of the seven cell lines in experiments using cRM72. Altogether, the results of our FISH studies indicated that the chromosome 12 breakpoints of all seven cell lines map between cRM36 and cRM103, which spans a genomic region of about 1.7 Mb.

Fine Mapping of 12q Breakpoints in Cell Lines Derived from Pleomorphic Adenomas of the Salivary Glands.

For subsequent fine mapping of the chromosome 12 breakpoints of the seven pleomorphic salivary gland adenoma cell lines, additional FISH studies were performed, as schematically summarized in FIG. 1. The breakpoints of cell lines Ad-211/SV40, Ad-295/SV40, and Ad-366/SV40 appeared to be located in the DNA region between cRM76 and cRM133, which was estimated to be about 75 kb. The breakpoints of the four other cell lines were found in different areas of the 1.7 Mb region between cRM36 and cRM103. That of cell line Ad-248/SV40 in a DNA segment of about 270 kb between cRM33 and cRM76, that of Ad-263/SV40 in a DNA segment of about 1 Mb between cRM98 and cRM103, that of Ad-302/SV40 in a DNA segment of about 240 kb between cRM33 and cRM36, and that of Ad-386/SV40 in a DNA segement of about 100 kb between cRM98 and cRM133. In conclusion, these results indicated that the chromosome 12 breakpoints of most (5 out of 7) of the cell lines are dispersed over the 445 kb-genomic region on the long arm of chromosome 12 between cRM33 and cRM98. It is important to note already here that precisely this region was recently shown to contain the chromosome 12q breakpoints in cell lines derived from primary uterine leiomyomas (see FIG. 3) and was therefore designated ULCR12 (Schoenmakers et al., 1994b). As this segment of the long arm of chromosome 12 is involved in at least two types of solid tumors (Schoenmakers et al., 1994b; this study) and, as we will show below, also in a third solid tumor type, we will from now on refer to the DNA interval between cRM36 and cRM103 as MAR (multiple aberration region).

FISH Mapping of 12q Breakpoints in Primary Pleomorphic Salivary Gland Adenomas.

Our FISH studies on metaphase chromosomes of pleomorphic adenomas of the salivary glands presented so far were restricted to cell lines derived from primary tumors. Although it is reasonable to assume that the chromosome 12 breakpoints in cell lines are similar if not identical to the ones in the corresponding primary tumors, differences as a result of the establishment of cell lines or subsequent cell culturing cannot fully be excluded. Therefore, we have investigated whether the chromosome 12 breakpoints in three primary salivary gland adenomas were mapping to MAR as well. To test this possibility, a combination of cosmid clones cRM33 and cRM103 were used as molecular probe. In all three cases, this cosmid pool clearly spanned the chromosome 12 breakpoints (data not shown), indicating that these breakpoints were indeed localized within MAR. In a recent study (Wanschura et al., submitted for publication), it was reported that the chromosome 12 breakpoints of five primary uterine leiomyomas with 12q14–q15 aberrations were all found to cluster within the 1.5 Mb DNA fragment (between cRM33 and cRM103), which is known to harbor the breakpoints of various cell lines derived from primary uterine leiomyomas (schematically summarized in FIG. 3). Consistent with the results of the breakpoint mapping studies using cell lines, the results with the two primary solid tumor types establish that the breakpoints of the primary tumor cells are located in MAR.

Chromosome Segment 12q13–q15 Breakpoints of Lipomas Mapping within MA.

To test the possibility that the chromosome 12 breakpoints of other solid tumors with 12q13–q15 aberrations also mapped within MAR, we studied two lipomas cell lines by FISH analysis—Li-14/SV40 and Li-538/SV40. The chromosome 12 aberrations of these two lipoma cell lines are given in Table 1. As molecular probes, cosmid clones cRM33, cRM53, cRM72, cRM76, cRM99, cRM103, and cRM133 were used. The breakpoint of Li-14/SV40 was mapped to the 75 kb DNA interval between RM76 and RM133, and that of Li-538/SV40 to the 90 kbp interval between RM76 and RM99 (data not shown), as schematically illustrated in FIG. 3. Similar FISH analysis of two primary lipomas using a mixture of cRM36 and cRM103 as molecular probe resulted in a hybridization pattern indicating that the mixture of probes detected sequences on either side of the breakpoints. These results are the first indications that also in lipoma, chromosome 12q13–q15 breakpoints occur that map within MAR. More lipoma cases should be tested to allow proper interpretation of this observation.

Discussion

In this study, we have mapped the chromosome 12 breakpoints of three primary pleomorphic salivary gland adenomas as well as seven established cell lines derived from such tumors. All breakpoints appeared to be located in a previously molecularly cloned and characterized chromosome DNA segment on the long arm of chromosome 12, of about 1.7 Mb in size, with five of them clustering in a DNA interval of less than 500 kb. The 1.7 Mb DNA region apparently contains a major breakpoint cluster region for this type of tumor. In a previous study, we have described the characterization of the chromosome 12 breakpoint of pleomorphic salivary gland adenoma cell line Ad-312/SV40 (Kools et al., 1995). The breakpoint of this cell line is now known to map at a distance of more than 2 Mb distally to this major breakpoint cluster region reported here. It is possible that the Ad-312/SV40 breakpoint involves other pathogenetically relevant genetic sequences than those affected by the clustered breakpoints. However, the possibility should not yet be excluded that all the 12q13–q15 breakpoints in pleomorphic salivary gland adenomas mapped so far belong to the same category and are dispersed over a relatively large DNA region of this chromosome, reminiscent of the 11q13 breakpoints in B-cell malignancies (Raynaud et al., 1993). More precise pinpointing of the various breakpoints could shed more light on this matter.

Of importance is the observation that the DNA segment that harbors the clustered 12q breakpoints of pleomorphic salivary gland adenomas appears to coincide with the DNA region that was recently defined as the uterine leiomyoma cluster region of chromosome 12 breakpoints, known as ULCR12 (Schoenmakers et al., 1994b). Of further interest is the fact that this region of chromosome 12 also harbors breakpoints of primary lipomas and lipoma cell lines derived from primary tumors with 12q13–q15 aberrations. Altogether, the results of all these studies now clearly demonstrate that chromosome 12 breakpoints of three distinct solid tumor types map to the same 1.7 Mb genomic region on the long arm of chromosome 12, establishing this region to be a multiple aberration region. To reflect this characteristic, we have designated this DNA segment MAR.

Genetic aberrations involving chromosomal region 12q13–q15 have been implicated by many cytogenetic studies in a variety of solid tumors other than the three already mentioned. Involvement of 12q13–q15 has also been reported for endometrial polyps (Walter et al., 1989; Vanni et al., 1993), clear cell sarcomas characterized by recurrent t(12;22)(q13;q13) (Fletcher, 1992; Reeves et al., 1992; Rodriguez et al., 1992), a subgroup of rhabdomyosarcoma (Roberts et al., 1992) and hemangiopericytoma (Mandahl et al., 1993a), chondromatous tumors (Mandahl et al., 1989; Bridge et al., 1992; Hirabayashi et al., 1992; Mandahl et al., 1993b), and hamartoma of the lung (Dal Cin et al., 1993). Finally, several case reports of solid tumors with involvement of chromosome region 12q13–q15 have been published—e.g., tumors of the breast (Birdsal et al., 1992; Rohen et al., 1993), diffuse astrocytomas (Jenkins et al., 1989), and a giant-cell tumor of the bone (Noguera et al., 1989). On the basis of results of cytogenetic studies, no predictions could be made about the relative distribution of the breakpoints of these tumor types. In light of the results of the present study, it.would be of interest to see whether the breakpoints of any of these solid tumors also map within or close to MAR. The various cosmid clones available now provide the means to test this readily.

The observation that 12q breakpoints of at least three different types of solid tumors map to the same DNA region is intriguing as it could be pointing towards the possibility that the same genetic sequences in MAR are pathogenetically relevant for tumor development in different tissues. If so, it is tempting to speculate that the gene(s) affected by the genetic aberrations might be involved in growth regulation. On the other hand, one cannot yet exclude the possibility that genetic sequences in MAR are not pathogenetically relevant, as the observed clustering of genetic aberrations in MAR could simply reflect genetic instability of this region, which becomes apparent in various solid tumors. To obtain more insight in this matter, the genes residing in MAR should be identified and characterized, and this can be achieved by various approaches using several techniques (Parrish and Nelson, 1993).

Acknowledgments

The constructive support of managing director G. Everaerts is greatly acknowledged. The authors would like to thank P. Dal Cin, J. Haubrich, R. Hille, G. Stenman, and I. De Wever for providing the solid tumor specimens studied in the present report; C. Huysmans, E. Meyen, K. Meyer-Bolte, R. Mols, and M. Willems for excellent technical assistance; and M. Leys for artwork. This work was supported in part by the EC through Biomed 1 program "Molecular Cytogenetics of Solid Tumours", the "Geconcerteerde Onderzoekacties 1992–1996", the National Fund for Scientific Research (NFWO; Kom op tegen Kanker), the "ASLK-programma voor Kankeronderzoek", the "Schwerpunktprogramm: Molekulare und Klassische Tumorcytogenetik" of the Deutsche Forschungsgemeinschaft, and the Tönjes-Vagt Stiftung. This text presents results of the Belgian programme on Interuniversity Poles of attraction initiated by the Belgian State, Prime Minister's Office, Science Policy Programming. The scientific responsibility is assumed by its authors. J. W. M. Geurts is an "Aspirant" of the National Fund for Scientific Research (NFWO; Kom op tegen Kanker).

References

Aman P, Ron D, Mandahl N, Fioretos T, Heim S, Arheden K, Willen H, Rydholm A, Mitelman F (1992) Rearrangement of the transcription factor gene CHOP in myxoid liposarcomas with t(12;16)(q13;p11. Genes Chromosom Cancer 5: 278–285.

Birdsal S H, MacLennan K A, Gusterson, B A (1992) t(6;12) (q23;q13) and t(10;16) (q22;p11) in a phyllodes tumor of the breast. Cancer Genet Cytogenet 60: 74–77.

Bridge J A, Persons D L, Neff J R, Bhatia P (1992) Clonal karyotypic aberrations in enchondroma. Cancer Detect Prev 16: 215–219.

Bullerdiek J, Wobst G, Meyer-Bolte K, Chilla R, Haubrich J, Thode B, Bartnitzke S (1993): Cytogenetic subtyping of 220 salivary gland pleomorphic adenomas: correlation to occurrence, histological subtype, and in vitro cellular behavior. Cancer Genet Cytogenet 65: 27–31.

Craig I W, Gedde-Dahl T, Gemmill R, Kucherlapati R (1993) Report of the committee on the genetic constitution of chromosome 12. Genome Prior Rep 1: 402–418.

Crozat A, Aman P, Mandahl N, Ron D (1993) Fusion of CHOP to a novel RNA-binding protein in human myxoid liposarcoma. Nature 363: 640–644.

Dal Cin P, Kools P, De Jonge I, Moerman P h, Van de Ven W, Van den Berghe H (1993) Rearrangement of 12q14–q15 in pulmonary chondroid hamartoma. Genes Chromosom Cancer 8: 131–133.

Fletcher J A (1992) Translocation (12;22)(q13–q14;q12) is a nonrandom aberration in soft-tissue clear-cell sarcoma. Genes Chromosom Cancer 5: 184.

Geurts J M W, Schoenmakers H F P M, Mols R, Van de Ven W J M (1994) An improved procedure to quickly isolate and sequence the termini of DNA inserts of yeast artificial chromosomes. Meth Mol Cell Biol 4: 257–265.

Green E D, Olson M V (1990) Systematic screening of yeast artificial-chromosome libraries using the polymerase chain reaction. Proc Natl Acad Sci USA 87: 1213–1217.

Hirabayashi Y, Yoshida M A, Ikeuchi T. Ishida T, Kojima T, Higaki S, Machinami R, Tonomura A (1992) Chromosome rearrangements at 12q13 in two cases of chondrosarcomas. Cancer Genet Cytogenet 60: 35–40.

Jenkins R B, Kimmell D W, Moertel C A, Schulz C A, Menezes R M, Scheihauer B, Kelly P J, Dewald G W (1989) Recurrent cytogenetic abnormalities in 80 gliomas. Cytogenet Cell Genet 51: 1019.

Kazmierczak B, Bartnitzke S, Hartl M, Bullerdiek J (1990): In vitro transformation by the SV40 "early region" of cells from a human benign salivary gland tumour with a 12q13—q15 rearrangement. Cytogenet Cell Genet 53: 37–39.

Keats B, Ott J, Conneally M (1989) Report of the committee on linkage and gene order. Cytogenet Cell Genet 51: 459–502.

Kievits T, Dauwerse J G, Wiegant J, Devilee P, Breuning MH, Cornelisse C J, van Ommen G, Pearson P L (1990) Rapid subchromosomal localization of cosmids by non-radioactive in situ hybridization. Cytogenet Cell Genet 53: 134–136.

Kools P F J, Roebroek A J M, Van de Velde H J K, Marynen P, Bullerdiek J, Van de Ven W J M (1993): Regional mapping of the human N S P gene to chromosome 14q21–q22 by fluorescence in situ hybridization. Cytogenet Cell Genet 66:48–50.

Kools P F J, Wanschura S, Schoenmakers E F P M, Geurts J W M, Mols R, Kazmierczak B, Bullerdiek J, Van den Berghe H, Van de Ven W J M (1995) Identification of the chromosome 12 translocation breakpoint region of a pleomorphic salivary gland adenoma with t(1;12) (p22;q15) as the sole cytogenetic abnormality. Cancer Genet Cytogenet, In press, 1995.

Kucherlapati R, Craig I, Marynen P (1994) Report of the second international workshop on human chromosome 12 mapping 1994. Cytogenet Cell Genet 67: 245–276.

Mandahl N, Heim S, Arheden K, Rydholm A, Willen H, Mitelman F (1989) Chromosomal rearrangements in chondromatous tumors. Cancer 65: 242–248.

Mandahl N, Orndal C, Heim S, Willen H, Rydholm A, Bauer H C F, Mitelman F (1993a) Aberrations of chromosome segment 12q13–q15 characterize a subgroup of hemangiopericytomas. Cancer 71: 3009–3013.

Mandahl N, Willen H, Rydholm A, Mitelman F (1993b) Rearrangement of band q13 on both chromosomes 12 in a periosteal chondroma. Genes Chrom Cancer 6: 121–123.

Mitelman F (1991): Catalog of Chromosome Aberrations in Cancer. 4th ed., New York, Alan R. Liss.

Montgomery K T, LeBlanc J M, Tsai P, McNinch J S, Ward D C, De Jong P J, Kucherlapati R, Krauter K S (1993) Characterization of two chromosome 12 cosmid libraries and development of STSs from cosmids mapped by FISH. Genomics 17:682–693.

Nelson D L, Ledbetter S A, Corbo L, Victoria M F, Ramirez-Solis R, Webster T D, Ledbetter D H, Caskey C T (1989) Alu polymerase chain reaction: A method for rapid isolation of human-specific sequences from complex DNA sources. Proc Natl Acad Sci USA 86: 6686–6690.

Nilbert M, Heim S (1990) Uterine leiomyoma cytogenetics. Genes Chromosom Cancer 2:3–13.

Noguera R, Llombart-Bosch A, Lopez-Gines C, Carda C, Fernandez Cl (1989) Giant-cell tumor of bone, stage II, displaying translocation t(12;19)(q13;q13). Virchows Archiv A Pathol Anat 415: 377–382.

Pandis N, Heim S, Bardi G, Flodérus U-M, Willén H, Mandahl N, Mitelman F (1991) Chromosome analysis of 96 uterine leiomyomas. Cancer Genet Cytogenet 55:11–18.

Parrish J E, Nelson D L (1993) Methods for finding genes a major rate-limiting step in positional cloning. GAT 10: 29–41.

Rabbitts T H, Forster A, Larson R, Nathan P (1993) Fusion of the dominant negative transcription regulator CHOP with a novel gene FUS by translocation t(12;16) in malignant liposarcoma. Nature Genet 4: 175–180.

Raynaud S D, Bekri S, Leroux D, Grosgeorge J, Klein B, Bastard C, Gaudray P, Simon M P (1993) Expanded range of 11q13 breakpoints with differing patterns of cyclin D1 expression in B-cell malignancies. Genes Chromosom Cancer 8: 80–87.

Reeves B R, Fletcher C D M, Gusterson B A (1992) Translocation t(12;22)(q13;q13) is a nonrandom rearrangement in clear cell sarcoma. Cancer Genet Cytogenet 64: 101–103.

Roberts P, Browne C F, Lewis I J, Bailey C C, Spice R D, Williams J, Batcup G (1992) 12q13 Abnormality in rhabdomyosarcoma. A nonrandom Occurrence? Cancer Genet Cytogenet 60: 135–140.

Rodriguez E, Sreekantaiah C, Reuter V E, Motzer R J, Chaganti R S K (1992) t(12;22) (g13;q13) and trisomy 8 are nonrandom aberrations in clear-cell sarcoma. Cancer Genet Cytogenet 64: 107–110.

Rohen C, Bonk U, Staats B, Bartnizke S, Bullerdiek J (1993) Two human breast tumors with translocations involving 12q13–q15 as the sole cytogenetic abnormality. Cancer Genet Cytogenet 69: 68–71.

Sambrook J, Fritsch E F, Maniatis T (1989) Molecular Cloning: A Laboratory Manual. Cold Spring Harbor Laboratory Press, Cold Spring Harbor, N.Y.

Sandros J, Stenman G, Mark J (1990): Cytogenetic and molecular observations in human and experimental salivary gland tumours. Cancer Genet Cytogenet 44: 153–167.

Schoenmakers H F P M, Kools P F J, Kazmierczak B, Bullerdiek J, Claussen U, Horsthemke B, Van den Berghe H, Van de Ven WJM (1993) Isolation of a somatic cell hybrid retaining the der(16)t(12;16) (q13;p11.2) from a myxoid liposarcoma cell line. Cell Genet Cytogenet 62: 159–161.

Schoenmakers H F M, Kools P F J, Mols R, Kazmierczak B, Bartnitzke S, Bullerdiek J, Dal Cin P, De Jong P J, Van den Berghe H, Van de Ven W J M (1994a) Physical mapping of chromosome 12q breakpoints in lipoma, pleomorphic salivary gland adenoma, uterine leiomyoma, and myxoid liposarcoma. Genomics 20: 210–222.

Schoenmakers H F P M, Mols R, Wanschura S, Kools P F J, Geurts J M, Bartnitzke S, Bullerdiek J, Van den Berghe H, Van de Ven W J M (1994b) Identification, molecular cloning and characterization of the chromosome 12 breakpoint cluster region of uterine leiomyomas. Genes Chromosom Cancer 11: 106–118.

Second International Chromosome 12 Workshop, New Haven, Conn., USA, Jun. 20–22, 1994.

Seifert G, Miehlke A, Haubrich J, Chilla R (1986): Diseases of the salivary glands. Pathology. Diagnosis. Treatment. Facial nerve surgery. Translated by P. M. Stell. Thieme, Stuttgart, New York, pp 182–194.

Smit V T H B M, Wessels J W, Mollevanger P, Schrier P I, Raap A K, Beverstock G C, Cornelisse C J (1990) Combined GTG-banding and nonradioactive in situ hybridization improves characterization of complex karyotypes. Cytogenet Cell Genet 54:20–23.

Sreekantaiah C, Leong S L P, Karakousis C P, McGee D L, Rappaport W D, Villar H V, Neal D, Fleming S, Wankel A, Herrington P N, Carmona R, Sandberg A A (1991) Cytogenetic profile of 109 lipomas. Cancer Res 51: 422–433.

Vanni R, Dal Cin P, Marras S, Moerman P h, Andria M, Valdes E, Deprest J, and Van den Berghe H (1993) Endometrial polyp: Another benign tumor characterized by 12q13–q15 changes. Cancer Genet Cytogenet 68:32–33.

Walter T A, Xuan Fan S, Medchill M T, Berger C S, Decker H-J H, Sandberg A A (1989) Inv(12) (p11.2q13) in an endometrial polyp. Cancer Genet Cytogenet 41: 99–103.

Wanschura S, Belge G, Stenman G, Kools P, Dal Chin P, Schoenmakers E, Huysmans C, Bartnizke S, Van de Ven W, and Bullerdiek J (submitted for publication). Mapping of the translocation breakpoints of primary pleomorphic adenomas and lipomas within a common region of chromosome 12.

Legends of Figures of Annex 1

FIG. 1. Schematic representation of FISH mapping data obtained for the seven pleomorphic salivary gland adenoma cell lines tested in this study. Cosmid clones which were used as probes in the FISH mapping studies map at sequence-tagged sites obtained from overlapping YAC clones. They are named after the acronyms of the STSs, as shown in the boxes, and the relative order of these is as presented. The DNA interval between RM69 and RM72 is estimated to be about 2.8 Mb. The solid lines indicate DNA intervals in which the breakpoints of the various cell lines are located. The dots indicate FISH experiments that were performed on metaphase chromosomes of the various cell lines using a cosmid clone corresponding to the STS indicated above these as molecular probe. The relative positions of MAR and ULCR12 are indicated in the lower part of the figure. Ad, pleomorphic salivary gland adenoma; MAR, multiple aberration region; ULCR12, uterine leiomyoma cluster region of chromosome 12 breakpoints.

FIG. 2. a: Partial karyotype of Ad-295/SV40 showing der(8), der(12), der(18) and the corresponding normal chromosomes. b: FISH analysis of metaphase chromosomes of Ad-295/SV40 cells using DNA of cosmid clone cRM76 as molecular probe. Hybridization signals on normal chromosome 12 (arrow) and der(12) (arrowhead). c: GTG-banding pattern of metaphase chromosomes of Ad-295/SV40 shown in b. d: FISH analysis of metaphase chromosomes of Ad-295/SV40 cells using DNA of cosmid clone cRM103 as molecular probe. Hybridization signals on normal chromosome 12 (arrow) and der(18) (arrowhead).

FIG. 3. Schematic representation of chromosome 12 breakpoint mapping data obtained for primary pleomorphic salivary gland adenomas, uterine leiomyomas, and lipomas as well as cell lines derived from such solid tumors. Results are compared to data for primary uterine leiomyomas (Wanschura et al., sumitted for publication) and cell lines derived from such tumors (Schoenmakers et al., 1994b). Cosmid clones which were used as probes in the FISH mapping studies correspond to sequence-tagged sites obtained from overlapping YAC clones. Cosmid clones were named after the acronyms of the STSs, as shown in the boxes, and the relative order of these is as presented. The estimated sizes of DNA intervals between STSs are indicated. A d, pleomorphic salivary gland adenoma; L i, lipoma; L M, uterine leiomyoma.

Annex 2

Lead Article

Identification of the Chromosome 12 Translocation Breakpoint Region of a Pleomorphic Salivary Gland Adenoma with t(1;12)(p22;q15) as the Sole Cytogenetic Abnormality Patrick F. J. Kools, Sylke Wanschura, Eric F. P. X. Schoenmakers, Jan W. M. Geurts, Raf Mols, Bernd Kazmierczak, Jörn Bullerdiek, Herman Van den Berghe and Wim J. M. Van de Ven ABSTRACT: Cell line Ad-312/SV40, which was derived from a primary pleomorphic salivary gland adenoma with t(1;12)(p22;q15), was used in fluorescence in situ hybridization (FISH) analysis to characterize its translocation breakpoint region on chromosome 12. Results of previous studies have indicated that the chromosome 12 breakpoint in Ad-312/SV40 is located proximally to locus D12S8 and distally to the CHOP gene. We here describe two partially overlapping yeast artificial chromosome (YAC) clones, Y4854 (500kbp) and Y9091 (460 kbp), which we isolated in the context of a chromosome walking project with D12S8 and CHOP as starting points. Subsequently, we have isolated cosmid clones corresponding to various sequence-tagged sites (STSs) mapping within the inserts of these YAC clones. These included cRM51, cRM69, cRM8S, cRM90, cRM91, cRM110, and cRM111. We present a composite long-range restriction map encompassing the inserts of these two YAC clones and show by FISH analysis, that both YACs span the chromosome 12 breakpoint as present in Ad-312/SV40 cells. In FISH studies, cosmid clones cRM85, cRM90 and cRM111 appeared to map distally to the chromosome 12 breakpoint whereas cosmid clones cRM51, cRM69, cRM91, and cRM110 were found to map proximally to it. These results assign the chromosome 12 breakpoint in Ad-312/SV40 to a DNA region of less than 165 kbp. FISH evaluation of the chromosome 12 breakpoints in five other pleomorphic salivary gland adenoma cell lines indicated that these are located proximally to the one in Ad-312/SV40, at a distance of more than 0.9 Mb from STS RM91. These results, while pinpointing a potentially critical region on chromosome 12, also provide evidence for the possible involvement of chromosome 12q13–q15 sequences located elsewhere.

Introduction

Pleomorphic salivary gland adenoma constitutes a benign epithelial tumor that originates from the major and minor salivary glands. It is the most common type of salivary gland tumor and accounts for almost 50% of all neoplasms in these organs; 85% of the tumors are found in the parotid gland, 10% in the minor salivary glands, and 5% in the submandibular gland [1]. About 50% of these adenomas appear to have a normal karyotype but cytogenetic studies have also revealed recurrent specific chromosome anomalies [2, 3]. Frequently observed anomalies include aberrations of chromosome 8, usually involving the 8q12–q13 region, with the most common aberration a t(3;8) (p21;q12), and aberrations of chromosome 12, usually translocations involving region 12q13–q15. Non-recurrent clonal chromosome abnormalities have also been reported. The highly specific pattern of chromosome rearrangements with consistent breakpoints at 8q12–q13 and 12q13–q15 suggests that these chromosomal regions harbour genes that might be implicated in the development of these tumors. Molecular cloning of the chromosome breakpoints and characterization of their junction fragments may lead to the identification of pathogenetically relevant genes. At present, no such molecular data have yet been reported for these tumors.

On the basis of fluorescence in situ hybridization (FISH) data, the chromosome 12 breakpoints in six pleomorphic salivary gland adenoma cell lines were recently shown to be mapping to region 12q13–q15, more precisely, to the genomic interval between loci D12S19 and D12S8 [4, 5]. The sex-averaged genetic size of this genomic DNA interval was reported at HGM10 to be 7 cM [6]. We also reported that the chromosome 12 breakpoints in salivary gland adenomas map distally to the CHOP gene [5], which supports an earlier study indicating that the 12q13–q15 translocation breakpoints in pleomorphic salivary gland adenomas are different from that in myxoid liposarcoma [7]. Here, we report about the physical mapping of the chromosome 12 breakpoint in pleomorphic salivary gland adenoma cell line Ad-312/SV40, which carries a t(1;12) (p22;q15) as the only cytogenetic abnormality.

Materials and Methods

Tumor Cell Lines.

Human tumor cell lines used in this study included the previously described pleomorphic salivary gland adenoma cell lines Ad-248/SV40, Ad-263/SV40, Ad-295/SV40, Ad-302/SV40, Ad-312/SV40, and Ad-366/SV40 [5, 8]. Cells were cultivated in TC199 culture medium with Earle's salts supplemented with 20% fetal bovine serum. Other cell lines used in this study included somatic cell hybrid PK89–12, which contains chromosome 12 as the sole human chromosome in a hamster genetic background [9], and somatic cell hybrid LIS-3/SV40/A9-B4 [4]. The latter cell line was obtained upon fusion of myxoid liposarcoma cell line LIS-3/SV40, which carries the specific t(12;16) (q13;p11.2), with mouse A9 cells. This somatic cell hybrid was previously shown to contain der(16) but neither der(12) nor the normal chromosome 12 [4]. PK89–12 and LIS-3/SV40/A9-B4 cells were grown in DME-F12 medium supplemented with 10% fetal bovine serum. Cell lines were analyzed by standard cytogenetic techniques at regular intervals.

Isolation of YAC and Cosmid Clones.

In the context of human genome mapping studies, which will be described in detail elsewhere (Schoenmakers et al., in preparation), we isolated YAC clones Y4854 and Y9091 from the first-generation CEPH YAC library [10], and cosmid clones cRM51, cRM69, cRM85, cRM90, cRM91, cRM103, cRM110, and cRM111 from the chromosome-12-specific, arrayed cosmid library LLNLNCO1 [11]. YAC and cosmid clones were isolated as described before [5]. Initial screenings of the YAC, as well as the cosmid library, were performed using a screening strategy involving the polymerase chain reaction (PCR) [12]. Filter hybridization analysis was used as the final screening step, as previously described [5]. Cosmid clones were isolated using STSs and those corresponding to STSs within the inserts of YAC clones Y4854 and Y9091 are indicated in FIG. 1. STSs were obtained via rescue of YAC insert end-sequences using a vectorette-PCR procedure [13] or Alu-PCR [14, 15]. PCR products were sequenced directly via solid-phase fluorescent sequencing. Cosmid clones were grown and handled according to standard procedures [16]. YAC clones were characterized by pulsed-field gel electrophoresis [17], restriction mapping, and hybridization, as previously described [5].

Chromosome Preparations and Fluorescence in situ Hybridization.

Cells from the pleomorphic salivary gland adenoma tumor cell lines were treated with Colcemid (0.04 µg/ml) for 30 min and then harvested according to routine methods. Metaphase spreads of the tumor cells were prepared as described before [4]. To establish the identity of chromosomes in the FISH experiments, FISH analysis was performed after G-banding of the same metaphase spreads. G-banding was performed essentially as described by Smit et al. [18]. In situ hybridizations were carried out according to a protocol described by Kievits et al. [19] with some minor modifications [5, 20]. Cosmid and YAC DNA was labelled with biotin-11-dUTP (Boehringer Mannheim) or biotin-14-dATP (BRL, Gaithersburg), as described earlier [5]. Chromosomes were counterstained with propidium iodide and analyzed on a Zeiss Axiophot fluorescence microscope using a FITC filter (Zeiss). Results were recorded on Scotch (3M) 640asa film.

Results

Isolation and Characterization of YAC Clones Spanning the Chromosome 12 Breakpoint of Pleomorphic Salivary Gland Adenoma Cell Line Ad-312/SV40.

In previous studies [5], we mapped the chromosome 12 breakpoints of six pleomorphic salivary gland adenoma cell lines proximally to locus D12S8 and distally to CHOP. The DNA interval between these loci is somewhat smaller than 7 cM (estimated distance between the loci D12S8 and D12S19 [6]) but still substantially large. To molecularly define the translocation breakpoint of Ad-312/SV40, we have performed human genome mapping studies on the DNA interval between locus D12S8 and the CHOP gene. In the process of directional chromosome walking starting from D12S8 and the CHOP gene, we obtained overlapping YAC clones Y9091 and Y4854. The DNA insert of Y9091 appeared to be 460 kbp and that of Y4854, 500 kbp. Moreover, as we will demonstrate below, the DNA insert of each YAC clone appeared to span the chromosome 12 breakpoint of Ad-312/SV40. A long-range restriction map of the inserts of these YAC clones was made using pulsed-field gel electrophoresis and hybridization analysis (FIG. 1). On the basis of STS content mapping and Southern blot analysis, the inserts of YAC clones Y9091 and Y4854 appeared to overlap as indicated in FIG. 1. The tested STSs correspond to end-sequences of other overlapping YAC clones not shown here or to sequences obtained via inter-Alu-PCR. Of these, RM90 and RM91 represent such end-clone STSs of YAC Y9091, and RM48 and RM54 of Y4854, whereas RM110 and RM111 represent STSs derived from inter-Alu-PCR. For a number of STSs mapping within the inserts of YAC clones Y4854 and Y9091, corresponding cosmid clones were isolated for use in FISH analysis, e.g., cRM51, cRM69, cRM85, cRM90, cRM91, cRM110, and cRM111.

The inserts of the two overlapping YAC clones are most likely not chimeric, as was deduced from the following observations. FISH analysis of metaphase chromosomes of normal human lymphocytes with Y4854 or Y9091 DNA as molecular probe revealed hybridization signals only in chromosome region 12q13–q15. For Y9091, this was confirmed further by observations made in FISH studies in which cosmid clone cRM90 or cRM91 was used as probe; the DNA insert of each of these two cosmids corresponds to the alternative end-sequences of YAC clone Y9091. Finally, the end-sequence STSs of Y9091 appeared to map to chromosome 12 and distally to the CHOP gene, as was established by PCR analysis on PK89–12 DNA, which contains human chromosome 12 as the sole human chromosome in a hamster genetic background, and LIS-3/SV40/A9-B4 DNA, which was previously shown to contain der(16), from the specific t(12;16) of myxoid liposarcoma, but neither der(12) nor the normal chromosome 12 [4]. From the chromosome walking studies, we concluded that the overlapping inserts of the two YAC clones represent a DNA region of about 640-kbp, which is located on chromosome 12q between D12S8 and CHOP. As the 640-kbp composite long-range restriction map of the YAC contig was constructed with at least double coverage of the entire region, it is not unreasonable to assume that the 640-kbp region is contiguous with the chromosomal DNA, although microdeletions can not be excluded at this point.

Chromosome walking was routinely evaluated by FISH mapping of YAC clones and/or cosmid clones corresponding to YAC insert sequences. It should be noted that for the identification of chromosomes, G-banding was used in most cases. On the basis of such G-banding, hybridization signals could be assigned conclusively to chromosomes of known identity; this was also of importance for the cases with cross- or background hybridization signals that were occasionally observed. G-banding prior to FISH analysis resulted sometimes in rather weak hybridization signals or rather vague banding patterns. Therefore, we performed FISH experiments in which the YAC and cosmid clones to be evaluated were used in combination with a reference probe. Cosmid clone cPK12qter, which was serendipitously obtained during screening of a cosmid library, was selected as reference marker. FISH analysis of metaphase chromosomes of normal lymphocytes (FIG. 2A) revealed that cPK12qter maps to the telomeric region of the long arm of chromosome 12. To identify chromosome 12 in this experiment, centromere 12-specific probe pα12H8 [21] was used. FISH analysis of metaphase chromosomes of Ad-312/SV40 cells using YAC clone Y4854 (FIG. 2B) or Y9091 (FIG. 2C) in combination with reference probe cPK12qter revealed, in both cases, hybridization signals of the YAC insert on der(1) as well as der(12). We concluded from these results that the insert DNA of each YAC clone might span the chromosome 12 breakpoint in this cell line. It should be noted that G-banding revealed a telomeric association involving the short arm of chromosome 12 in FIG. 2C. The observation that YAC clone Y9091 spanned the chromosome 12 breakpoint in Ad-312/SV40 was confirmed independently in FISH studies in which cosmid clone cRM90 or cRM91 was used as molecular probe; they were shown to contain the alternative end-sequences of the Y9091 insert. cRM90 appeared to map distally to the chromosome 12 breakpoint, whereas cRM91 was found to map proximally (data not shown). These results also established the chromosomal orientation of the YAC contig shown in FIG. 1. In summary, we concluded from these FISH studies that the chromosome 12 translocation breakpoint in Ad-312/SV40 must be located in the DNA interval corresponding to the overlapping sequences (about 300 kbp) of the two YAC clones.

Fine Mapping of the Chromosome 12 Translocation Breakpoint of Ad-312/Sv40.

In an approach to further narrow the chromosome 12 translocation breakpoint region of Ad-312/SV40, cosmid clones with different mapping positions within YAC clone Y9091 were isolated. These included cRM69, cRM85, cRM110, and cRM111. cRM69 and cRM85 were isolated on the basis of STS sequences of YAC clones not shown here. cRM110 and cRM111 were obtained via inter-Alu-PCR. RM110 was shown by Southern blot analysis to hybridize to a terminal MluI fragment of Y9091 and not to the DNA insert of the overlapping YAC clone with RM69 as telomeric end-sequences. The location of RM110 is as indicated in FIG. 1. RM111 was shown to hybridize to a BssHII, MluI, PvuI, and SfiI fragment of Y9091 and is therefore located in the PvuI-SfiI fragment of Y9091, to which STS RM48 was also mapped (FIG. 1). FISH analysis of metaphase chromosomes of Ad-312/SV40 with cRM69 or cRM110as probe indicated that the DNA insert of these cosmids mapped proximally to the chromosome 12 translocation breakpoint in this cell line, as illustrated, for cRM69 in FIG. 3A. Subsequent FISH analysis of Ad-312/SV40 with cRM85 or cRM111as probe revealed hybridization signals distally to the translocation breakpoint, as illustrated for cRM111 in FIG. 3B. The results with cRM85 and cRM111 are in agreement with the observed breakpoint spanning by YAC clone Y4854 as cRM85 maps distally and cRM111 closely to STS RM48, which marks the telomeric end of YAC clone Y4854. In conclusion, the chromosome 12 translocation breakpoint in Ad-312/SV40 must be located in the DNA interval between cRM110 and cRM111, as schematically summarized in FIG. 4.

FISH Evaluation of Chromosome 12 Breakpoints in Other Pleomorphic Salivary Gland Adenoma Cell Lines.

To determine the position of their chromosome 12 breakpoints relative to that of Ad-312/SV40, five other pleomorphic salivary gland adenoma cell lines were evaluated by FISH analysis, as summarized schematically in FIG. 4. These cell lines, which were developed from primary tumors [5, 8], included Ad-248/SV40, Ad-263/SV40, Ad-295/SV40, Ad-302/SV40, and Ad-366/SV40. The chromosome 12 aberrations of these cell lines are listed in FIG. 4. FISH analysis of metaphase chromosomes of these cell lines using cRM91 revealed that the chromosome 12 breakpoints of all these cell lines mapped proximally to this cosmid clone (data not shown). Similar FISH analysis was also performed using a cosmid clone corresponding to sequence-tagged site RM103 as a probe. RM103 was found to map proximally to RM91 at a distance of about 0.9 Mbp. In all cases, cRM103 appeared to map distally to the chromosome 12 translocation breakpoints, indicating that the chromosome 12 breakpoints in these five pleomorphic salivary gland adenoma cell lines are located at a relatively large distance from that of Ad-312/SV40 cells.

Discussion

In the studies presented here, we have identified, molecularly cloned, and characterized a chromosome region on the long arm of chromosome 12 in which the translocation breakpoint of pleomorphic salivary gland adenoma cell line Ad-312/SV40 appears to map. In previous studies [5], we already provided evidence that the chromosome 12 breakpoint of this cell line was located between D12S8 and CHOP. Because the two breakpoints spanning YAC clones described here were obtained in directional chromosome walking experiments using D12S8 and the CHOP gene as initial starting points, the chromosome 12 breakpoint mapping results presented here confirm our previous claim. The FISH results obtained with the complete YAC insert of Y9091 as molecular probe were confirmed independently in FISH studies using cosmid clones containing sequences corresponding to various regions of the insert of this YAC clone. This is of importance, as the independent confirmatory results make it rather unlikely that the split signals observed with the complete insert of Y9091 can be explained otherwise than by a factual splitting of sequences represented in the YAC. The presence, for instance, of highly related genetic sequences on both sides of a chromosome breakpoint could easily lead to erroneous conclusions if they were based solely on FISH results of a YAC insert. Finally, our mapping studies have also established conclusively the chromosomal orientation of the long-range restriction map we have generated in these studies. This orientation was already predicted on the basis of two-color FISH studies (unpublished observations).

The FISH studies, described here, enabled us to map the chromosome 12 breakpoint in Ad-312/SV40 cells to the 190-kbp DNA interval between the established STSs RM48 and RM69. However, the breakpoint region can be narrowed somewhat further on the basis of the following. The fact that Y4854 was shown to span the breakpoint indicates that at least a considerable part of the telomeric half of this YAC clone must map distally to the breakpoint. Precisely how much remains to be established. On the other side, STS RM69 appeared to be located in about the middle of the DNA insert of cosmid clone cRM69, suggesting that the breakpoint is close to 25 kbp distally to RM69. Moreover, cRM69 appeared to lack RM110(data not shown) and, as cRM110 was found proximally to the chromosome 12 breakpoint in Ad-312/SV40 cells, the breakpoint should be even further distal to RM69 than the earlier-mentioned 25 kbp. Altogether, this narrows the chromosome 12 breakpoint region to a DNA interval, which must be considerably smaller than 165 kbp. Further pinpointing of the breakpoint will allow us to molecularly clone the chromosome 12 breakpoint and to characterize the genetic sequences in the breakpoint junction region, which might lead to the identification of pathogenetically relevant sequences. Identification of the genes present in the DNA inserts of YAC clones Y4854 and Y9091, via sequencing, direct hybridization, direct selection or exon-trapping, might constitute a useful alternative approach for identifying the gene in this region of the long arm of chromosome 12 that might be pathogenetically critical for pleomorphic salivary gland adenoma tumorigenesis.

The observation that the chromosome 12 breakpoints in other pleomorphic salivary gland adenomas are located in a remote and more proximal region on the long arm of chromosome 12 is of interest. It could imply that the chromosome 12 breakpoints in pleomorphic salivary gland adenomas are dispersed over a relatively large DNA region of the long arm of chromosome 12, reminiscent to the 11q13 breakpoints in B-cell malignancies [22]. Elucidation of the precise location of the chromosome 12 breakpoints in the other pleomorphic salivary gland adenoma cell lines could shed more light on this matter. On the other hand, it could point towards alternative sequences on the long arm of chromosome 12 between D12S8 and the CHOP gene that might be of importance, presumably for growth regulation in pleomorphic salivary gland adenoma. The fact that the chromosome 12 breakpoint region described here has sofar been found only in the Ad-312/SV40 cell line makes it necessary to analyze a larger number of salivary gland adenomas with chromosome 12q13–q15 aberrations to assess the potential relevance for tumorigenesis of the chromosome 12 sequences affected in the studied cell line. If more cases with aberrations in this particular region of chromosome 12 can be found, it would be of interest to find out whether these tumors form a clinical subgroup. Finally, chromosome translocations involving region q13–q15 of human chromosome 12 have been reported for a variety of other solid tumors: benign adipose tissue tumors, uterine leiomyoma, rhabdomyosarcoma, hemangiopericytoma, clear-cell sarcoma, chondromatous tumors, and hamartoma of the lung. Whether or not the chromosome 12 breakpoints in some of these tumors map within the same region as that of Ad-312/SV40 remains to be established. The YAC and cosmid clones described in this report constitute useful tools to investigate this.

The availability of a copy of the first-generation CEPH YAC library [10]and a copy of the arrayed chromosome 12-specific cosmid library (LLNL12NC01) [11] is greatly acknowledged. The cosmid library was constructed as part of the National Laboratory Gene Library Project under the auspices of the U.S. DOE by LLNL under contract No. W-7405-Eng-48. The authors acknowledge the excellent technical assistance of M. Dehaen, C. Huysmans, E. Meyen, K. Meyer-Bolte, and M. Willems and would like to thank M. Leys for art work. This work was supported in part by the EC through Biomed 1 program "Molecular Cytogenetics of Solid Tumours", the "Geconcerteerde onderzoekacties 1992–1996", the "Association Luxembourgeoise contre le Cancer", the National Fund for Scientific Research (NFWO; Kom op tegen Kanker), the "ASLK-programma voor Kankeronderzoek", the "Schwerpunktprogramm: Molekulare und Klassische Tumorcytogenetik" of the Deutsche Forschungsgemeinschaft, and the Tönjes-Vagt Stiftung. This text presents results of the Belgian programme on Interuniversity Poles of Attraction initiated by the Belgian State, Prime Minister's Office, Science Policy Programming. The scientific responsibility is assumed by its authors. J. W. M. Geurts is an "Aspirant" of the National Fund for Scientific Research (NFWO; Kom op tegen Kanker).

References

1. Seifert G, Miehlke A, Haubrich J, Chilla R (1986): Diseases of the salivary glands. Pathology. Diagnosis. Treatment. Facial nerve surgery. Translated by P. M. Stell. Thieme, Stuttgart, New York, pp 1820194.
2. Sandros J, Stenman G, Mark J (1990): Cytogenetic and molecular observations in human and experimental salivary gland tumours. Cancer Genet Cytogenet 44: 153–167.
3. Bullerdiek J, Wobst G, Meyer-Bolte K, Chilla R, Haubrich J, Thode B, Bartnitzke S (1993): Cytogenetic subtyping of 220 salivary gland pleomorphic adenomas: correlation to occurrence, histological subtype, and in vitro cellular behavior. Cancer Genet Cytogenet 65: 27–31.
4. Schoenmakers H F P M, Kools P F J, Kazmierczak B, Bullerdiek J, Claussen U, Horsthemke B, Van den Berghe H, Van de Ven W J M (1993): Isolation of a somatic cell hybrid retaining the der(16)t(12;16)(q13;p11.2) from a myxoid liposarcoma cell line. Cell Genet Cytogenet 62: 159–161.
5. Schoenmakers H F P M, Kools P F J, Mols R, Kazmierczak B, Bartnitzke S, Bullerdiek J, Dal Cin P, De Jong P J, Van den Berghe H, Van de Ven W J M (1993): Physical mapping of chromosome 12q breakpoints in lipoma, pleomorphic salivary gland adenoma, uterine leiomyoma, and myxoid liposarcoma. Genomics, 20: 210–222.
6. Keats B, Ott J, Conneally M (1989): Reports of the committee on linkage and gene order. Cytogenet Cell Genet 51: 459–502.
7. Stenman G, Sahlin P, Mark J. Chaganti R K S, Kindblom L S, Aman P (1993): The 12q13–q15 translocation breakpoints in pleomorphic adenoma and clear-cell sarcoma of tendons and aponeuroses are different from that in myxoid liposarcoma. Genes Chrom Cancer 7: 178–180.
8. Kazmierczak B. Bartnitzke S, Hartl M, Bullerdiek J (1990): In vitro transformation by the SV40 "early region" of cells from a human benign salivary gland tumour with a 12q13–q15 rearrangement. Cytogenet Cell Genet 53: 37–39.
9. Warburton D, Gersen S, Yu M-T, Jackson C, Handelin B, Housman D (1990): Monochromosomal rodent-human hybrids from microcell fusion of human lymphoblastoid cells containing an inserted dominant selectable marker. Genomics 6: 358–366.
10. Albertsen H M, Abderrahim H, Cann H M, Dausset J, Le Paslier D, Cohen D (1990): Construction and characterization of a yeast artificial chromosome library containing seven haploid human genome equivalents. Proc Natl Acad Sci USA 87: 4256–4260.
11. Montgomery K T, LeBlanc J M, Tsai P, McNinch J S, Ward D C, De Jong P J, Kucherlapati R, Krauter K S (1993): Characterization of two chromosome 12 cosmid libraries and development of STSs from cosmids mapped by FISH. Genomics 17:682-693.

12. Green E D, Olson M V (1990): Systematic screening of yeast artificial-chromosome libraries using the polymerase chain reaction. Proc Natl Acad Sci USA 87: 1213–1217.
13. Geurts J M W, Schoenmakers H F P M, Mols R, Van de Ven W J M (1994): Improved procedure for rapid isolation and sequencing of DNAS termini in yeast artificial chromosomes. Meth Mol Cell Biol, In Press.
14. Nelson D L, Ledbetter S A, Corbo L, Victoria M F, Ramirez-Solis R, Webster T D, Ledbetter D H, Caskey C T (1989): Alu polymerase chain reaction. A method for rapid isolation of human-specific sequences from complex DNA sources. Proc Natl Acad Sci USA 86: 6686–6690.
15. Breukel C, Wijnen J, Trops C, Van de Klift H. Dauwerse H, Meera Khan P (1990): Vector-Alu PCR: a rapid step in mapping cosmids and YACs. Nucl Acids Res 18: 3097.
16. Sambrook J, Fritsch EF, Maniatis T (1989): Molecular Cloning: A Laboratory Manual. Cold Spring Harbor Laboratory Press, Cold Spring Harbor, N.Y.
17. Chu G, Vollrath D, Davis R W (1986): Separation of large DNA molecules by contour-clamped homogeneous electric fields. Science 234: 1582–1585.
18. Smit V T H B M, Wessels J W, Mollevanger P, Schrier.P I, Raap E K, Beverstock G C, Cornelisse C J (1990): Combined GTG-banding and nonradipactive in situ hybridozation inproves characterization of complex karyotypes. Cytogenet Cell Genet 54: 20–23.
19. Kievits T, Dauwerse J G, wiegant J, Devilee P, Breuning M H, Cornelisse C J, van Ommen G, Pearson P L (1990): Rapid subchromosomal localization of cosmids by non-radioactive in situ hybridization. Cytogenet Cell Genet 53: 134–136.
20. Kools P F J, Roebroek A J J, Van de Velde H J K, Marynen P, Bullerdiek J, Van de Ven W J M (1993): Regional mapping of the human NSP gene to chromosome 14q21–q22 by fluorescence in situ hybridization. Cytogenet Cell Genet 66:48–50.
21. Looijenga L H J, Smit V T H B M, Wessels J W, Mollevanger P, Oosterhuis J W, Cornelisse C J (1990): Localization and polymorphism of a chromosome 12-specific α satellite DNA sequence. Cytogenet Cell Genet 53: 216–218.
22. Raynaud S D, Bekri S, Leroux D, Grosgeorge J, Klein B, Bastard C, Gaudray P, Simon M P (1993): Expanded range of 11q13 breakpoints with differing patterns of cyclin DI expression in B-cell malignancies. Genes Chrom Cancer 8: 80–87.

Legends of Figures of Annex 2

FIG. 1. Composite physical map of the overlapping DNA inserts of YAC clones Y4854 and Y9091. Sizes of the DNA inserts are indicated. The relative positions of the YAC clones are represented by bars below the long range physical map. Sequence-tagged sites (STSs) corresponding to end-clones of YACs, including YACs not shown here, are indicated by boxed RM codes above the restriction map. STSs obtained from inter-Alu-PCR products are given below the restriction map and the DNA regions to which they have been mapped are marked by arrows. B: BssHII; M: MluI; P: PvuI; Sf: SfiI. A polymorphic MluI site is marked by an asterisk.

FIG. 2. A) Mapping of cosmid clone cPK12qter to the telomeric region of the long arm of chromosome 12. Centromere 12-specific probe pα12H8 was used to establish the identity of chromosome 12. FISH analysis was performed on metaphase chromosomes of control human lymphocytes. Hybridization signals of cPK12qter are marked with small arrowheads, those of the centromere 12-specific probe with asterisks. B, C) FISH analysis of metaphase chromosomes of Ad-312/SV40 cells using DNA of YAC clone Y4854 (B) or Y9091 (C) as molecular probe in combination with cosmid clone cPK12qter as reference marker. Hybridization signals of the YAC clones on chromosome 12 are indicated by large arrowheads; those on der(1) by large arrows, and those on der(12) by small arrows, respectively. The hybridization signals of cosmid clone cPK12qter are indicated by small arrowheads.

FIG. 3. FISH analysis of metaphase chromosomes of Ad-312/SV40 cells using DNA of cosmid clone cRM69 (A) or cRM111 (B) as molecular probe in combination with cosmid clone cPK12qter as reference marker. The position of the hybridization signals of cPK12qter are indicated by small arrowheads. In (A), the position of the hybridization signal of cRM69 on normal chromosome 12 is indicated by a large arrowhead, and that on der(12) with a small arrow. In (B), the position of the hybridization signal of cRM111 on normal chromosome 12 is indicated by a large arrowhead, and that on der(1) with a large arrow.

FIG. 4. Schematic representation of FISH mapping data obtained for the six pleomorphic salivary gland adenoma cell lines tested in this study. The specific chromosome 12 aberrations in the various cell lines are given. Cosmid clones which were used as probes in the FISH mapping studies correspond to sequence-tagged sites obtained from overlapping YAC clones. Individual FISH experiments are indicated by dots. Cosmid clones were named after the acronyms of the STSs, as shown in the boxes, and the relative order of these is as presented. The DNA interval between RM90 and RM103 is estimated to be about 1.3 Mb. Insert: Schematic representation of the G-banded derivative chromosomes der(1) and der(12) of the Ad-312/SV40 cell line, which carries a t(1; 12)(p22;g15). The positions of the chromosome 12 breakpoints of Ad-248/SV40, Ad-263/SV40, Ad-295/SV40, Ad-302/SV40, and Ad-366/SV40 are distal to RM103 as indicated by the arrow.

What is claimed is:

1. An isolated nucleic acid, comprising the lipoma-preferred partner sequence depicted in FIG. 5 (SEQ ID NO: 162) or a completely complementary strand thereof.

2. The isolated nucleic acid of claim 1 in which the nucleic acid is labeled for use as a probe.

3. An expression vector comprising the lipoma-preferred partner sequence depicted in FIG. 5 (SEQ ID NO: 162).

4. A host cell comprising an expression vector according to claim 3.

* * * * *

UNITED STATES PATENT AND TRADEMARK OFFICE
CERTIFICATE OF CORRECTION

PATENT NO. : 6,544,784 B1
DATED : April 8, 2003
INVENTOR(S) : Jörn Bullerdiek et al.

It is certified that error appears in the above-identified patent and that said Letters Patent is hereby corrected as shown below:

Column 1,
Lines 6-7, "9521951.1, July 14, 1995" should read -- 95201951.1, filed Jul. 14, 1995 --
Line 47, "[15, 16)" should read -- [15, 16] -- (right parenthesis should be right bracket).

Column 3,
Lines 21-22, "(U28749); and" should read -- (U28749); -- (delete "and").
Line 24, "Example 5." should read -- Example 5; -- (delete period and insert semicolon).
Line 44, "DNA cosmid" should read -- DNA of cosmid --.
Line 45, "RM111" should read -- cRM 111--.

Column 5,
Line 26, "an-alternative" should read -- an alternative --.
Lines 26-27, "bothtranslocation" should read -- both translocation --.

Column 6,
Line 33, "trangsfering" should read -- transfering --.

Column 8,
Line 57, "analysis(of" should read -- analysis of --.
Lines 61-62, "Livermore.National" should read -- Livermore National -- (delete period).

Column 9,
Line 47, "2MM" should read -- 2mM --.
Line 65, "for min" should read -- for 30 min --.

Column 12,
Line 23, "(AFM207f2)" should read -- (AFM207xf2) --.
Line 30, "(AFM102d6)" should read -- (AFM102xd6) --.
Line 31, "(AFM249h9)" should read -- (AFM249xh9) --.
Line 31, "(AFM296d9)" should read -- (AFM296xd9) --.

Column 15,
Line 11, "slight. modification" should read -- slight modification --.
Line 12, "33-ET" should read -- 3'-ET --.
Line 16, "ACA TCA" should read -- ACA TC --.
Line 22, after "NO:5)" delete comma and insert period -- . --
Line 28, "iii) 51" should read -- iii) 5' --.
Line 65, "423" should read -- 42] --.
Line 67, "atleast" should read -- at least --.

UNITED STATES PATENT AND TRADEMARK OFFICE
CERTIFICATE OF CORRECTION

PATENT NO. : 6,544,784 B1
DATED : April 8, 2003
INVENTOR(S) : Jőrn Bullerdiek et al.

It is certified that error appears in the above-identified patent and that said Letters Patent is hereby corrected as shown below:

Column 16,
Line 46, "(Gensank)" should read -- (GenBank) --.
Line 66, "MAM" should read -- MAR --.

Column 17,
Line 3, delete hyphen between "the" and "HMGI-C".
Line 25, "tumor e11" should read -- tumor cell --.
Line 26, "known hat" should read -- known that --.
Line 67, delete hyphen between "ectopic" and "sequences".

Column 19,
Line 51, "(69]" should read -- [69] --.

Column 20,
Line 8, "(71, 72]" should read -- [71, 72] --.
Line 12, "MGl(Y)" should read -- HMGl(Y) --.
Line 13, "inding" should read -- binding --.
Line 53, "establisher" should read -- established --.

Column 22,
Line 17, "CDNA" should read -- cDNA --.

Column 23,
Line 3, "CDNA" should read -- cDNA --.

Column 24,
Line 47, "on expression" should read -- no expression --.

Column 25,
Line 20, "SEQ ID No: 12)" should read -- SEQ ID No: 12)) --.
Line 22, "No: 13)" should read -- No: 13)) --.
Line 25, "DATP" should read -- dATP -- .

Column 27,
Lien 8, "3'-55'" should read -- 3'-5' --.

Column 28,
Line 7, "CDNA" should read -- cDNA --.

UNITED STATES PATENT AND TRADEMARK OFFICE
CERTIFICATE OF CORRECTION

PATENT NO. : 6,544,784 B1
DATED : April 8, 2003
INVENTOR(S) : Jörn Bullerdiek et al.

It is certified that error appears in the above-identified patent and that said Letters Patent is hereby corrected as shown below:

Column 30,
Line 14, "(H-SPSKAAQKAEATGEK)8-MAPA" should read -- (H-SPSKAAQKKAEATGEKR) 8-MAPA --.
Table 1, Column 1, Line 9, "320F5" should read -- 320F6 --.
Table 1, Column 3, Line 4, "RM23" should read -- RM13 --.
Table 1, Column 7, Line 14, "Nb" should read -- ND -- .
Table 1, Column 6, Line 15, "U29337" should read -- U29037 --.
Table 1, Column 6, Line 18, "U29342" should read -- U29042 --.
Table 1, Column 6, Line 19, "U29340" should read -- U29040 --.
Table 1, Column 5, Line 22, "RM60" should read -- RM80 --.
Table 1, Column 6, Line 22, "U29335" should read -- U29036 --.
Table 1, Column 5, Line 23, "RM61" should read -- RM81 --.
Table 1, Column 3, Line 35, "RM204" should read -- RM104 --.
Table 1, Column 4, Line 47, "U29307" should read -- U29007 --.

Column 31,
Table 1-continued, Column 4, Line 2, "U29005" should read -- U29006 --
Table 1-continued, Column 6, Line 6, "U27125" should read -- U27135 --
Table 1-continued, Column 4, Line 7, "U26847" should read -- U26647 --
Table 1-continued, Column 6, Line 12, "U23792" should read -- U28792 --
Table 1-continued, Column 6, Line 20, "U28995" should read -- U28996 --
Table 1-continued, Column 1, Line 22, "261E5" should read -- 261E6 --
Table 1-continued, Column 4, Line 25, "U26794" should read -- U28794--
Table 1-continued, Column 1, Line 26, "255H3" should read -- 265H3 --
First line of text under Table 1, "clonees" should read -- clones --.
Table II, Line 1 in Heading "(SEQ ID NOS: 17-18)" should read -- (SEQ ID NOS: 17-102) --.

Column 33,
Table 3, first column heading "per" should read -- pcr --.
Table 3, third column heading "per" should read -- pcr --.
Table 3, fourth column heading "per" should read -- pcr --.
Table 3, Column 1, Line 6, "EH2-lower/EH2-upper" should read -- EM2-lower/EM2-upper --.
Table 3, Column 3, Line 6, "EH2-lower/EH2-upper" should read -- EM2-lower/EM2-upper --.
Table 3, Column 1, Line 7, "EH3-lower/EH3-upper" should read -- EM3-lower/EM3-upper --.
Table 3, Column 3, Line 7, "EH3-lower/EH3-upper" should read -- EM3-lower/EM3-upper --.

UNITED STATES PATENT AND TRADEMARK OFFICE
CERTIFICATE OF CORRECTION

PATENT NO. : 6,544,784 B1
DATED : April 8, 2003
INVENTOR(S) : Jőrn Bullerdiek et al.

It is certified that error appears in the above-identified patent and that said Letters Patent is hereby corrected as shown below:

Column 33, (continuation),
Table 3, Column 1, Line 8, "EH4-lower/EH4-upper" should read -- EM4-lower/EM4-upper --.
Table 3, Column 3, Line 8, "EH3-lower/EH3-upper" should read -- EM3-lower/EM3-upper --.

Columns 35-36,
Table 5, Column 9, Line 4, insert -- ? --
Table 5, Column 9, Line 5, insert -- ? --

Columns 37-38,
Table 5-continued, column entitled "Chrom.RACE", line 1, "N.T.$^{2}$" should read -- N.T.$^{1}$ --.
Table 5-continued, second column, line 5, "1321-89" should read -- 1321-89 ? --.
Table 5-continued, Column 9, line 5, "26" should read -- 16 --
Table 5-continued, Column 2, line 6, "1321-89" should read -- 1321-89 ? --.
Table 5-continued, Column 8, line 6, insert -- ? --
Table 5-continued, Column 2, line 8, "1321-89" should read -- 2100-89 ? --.
Table 5-continued, Column 2, line 11, "2100-89" should read -- 367 --.
Table 5-continued, Column 2, line 12, "367" should read -- 25 ? --.
Table 5-continued, Column 6, line 12, insert -- ? --.
Table 5-continued, Column 2, line 13, "#25" should read -- #837-88 --.
Table 5-continued, Column 2, line 15, "#837-88" should read -- #2100-89 --.
Table 5-continued, Column 2, line 17, "#2100-89" should read -- Li-501/SV40 --.
Table 5-continued, Column 2, line 19, "Li-501/SV40" should read -- Li-538/V40 --.
Table 5-continued, Column 2, line 21, "Li-583/SV40" should read -- #192 --.
Table 5-continued, Column 2, line 22, "#192" should read -- #203 --.
Table 5-continued, Column 2, line 23, "#203" should read -- #294 --.
Table 5-continued, Column 2, line 31, "#837-88" should read -- #837-88 ? --.
Table 5-continued, Column 2, line 32, "#2100-89" should read -- #2100-89 ? --.
Table 5-continued, Column 2, line 33, "#2100-89" should read -- #2100-89 ? --.

Columns 39-40,
Table 5, Column 8, Line 7, insert -- ? --.
After Table 5, third footnote, "repetive" should read -- repetitive --.

Column 42,
Line 2, "ID Nos." should read -- ID Nos: -- (delete period and insert colon).

UNITED STATES PATENT AND TRADEMARK OFFICE
CERTIFICATE OF CORRECTION

PATENT NO. : 6,544,784 B1
DATED : April 8, 2003
INVENTOR(S) : Jőrn Bullerdiek et al.

It is certified that error appears in the above-identified patent and that said Letters Patent is hereby corrected as shown below:

Column 47,
Line 30, "Schoen-akers" should read -- Schoemakers --.
Line 31, "Razmierczak" should read -- Kazimierczak --.

Column 50,
Table 1, Column 1, Row 4, "1683" should read -- 168.3 --.

Figure 9:
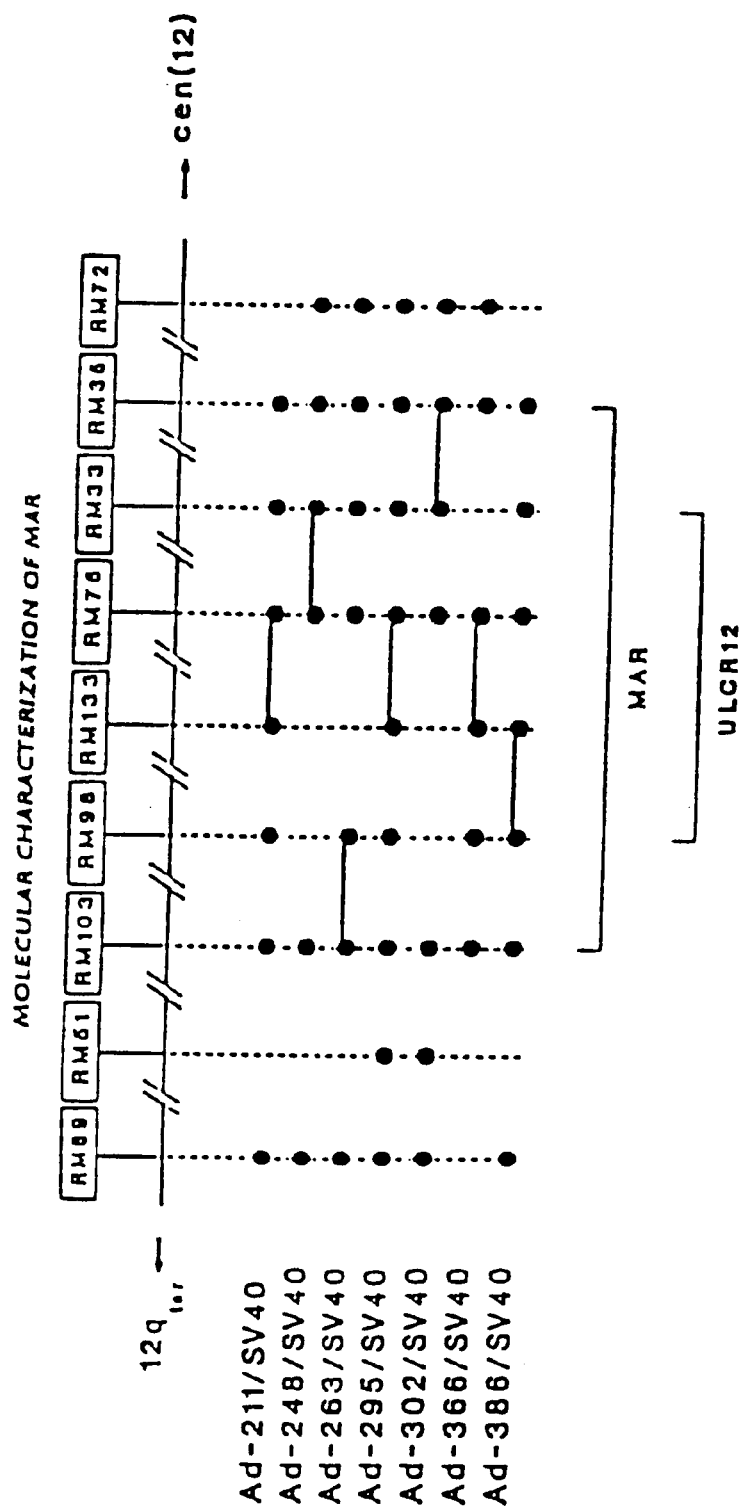
FIG. 9 is a schematic representation of FISH mapping data obtained for seven pleomorphic salivary gland adenoma cell lines.

Column 51,
Line 14 "in FIG. 1" should read -- in FIG. 9 --.
Line 19, "in FIG. 2" should read -- in FIG. 10 --.
Line 51, "in FIG. 1" should read -- in FIG. 9 --.
Line 62, "DNA segement" should read -- DNA segment --.

Figure 11:
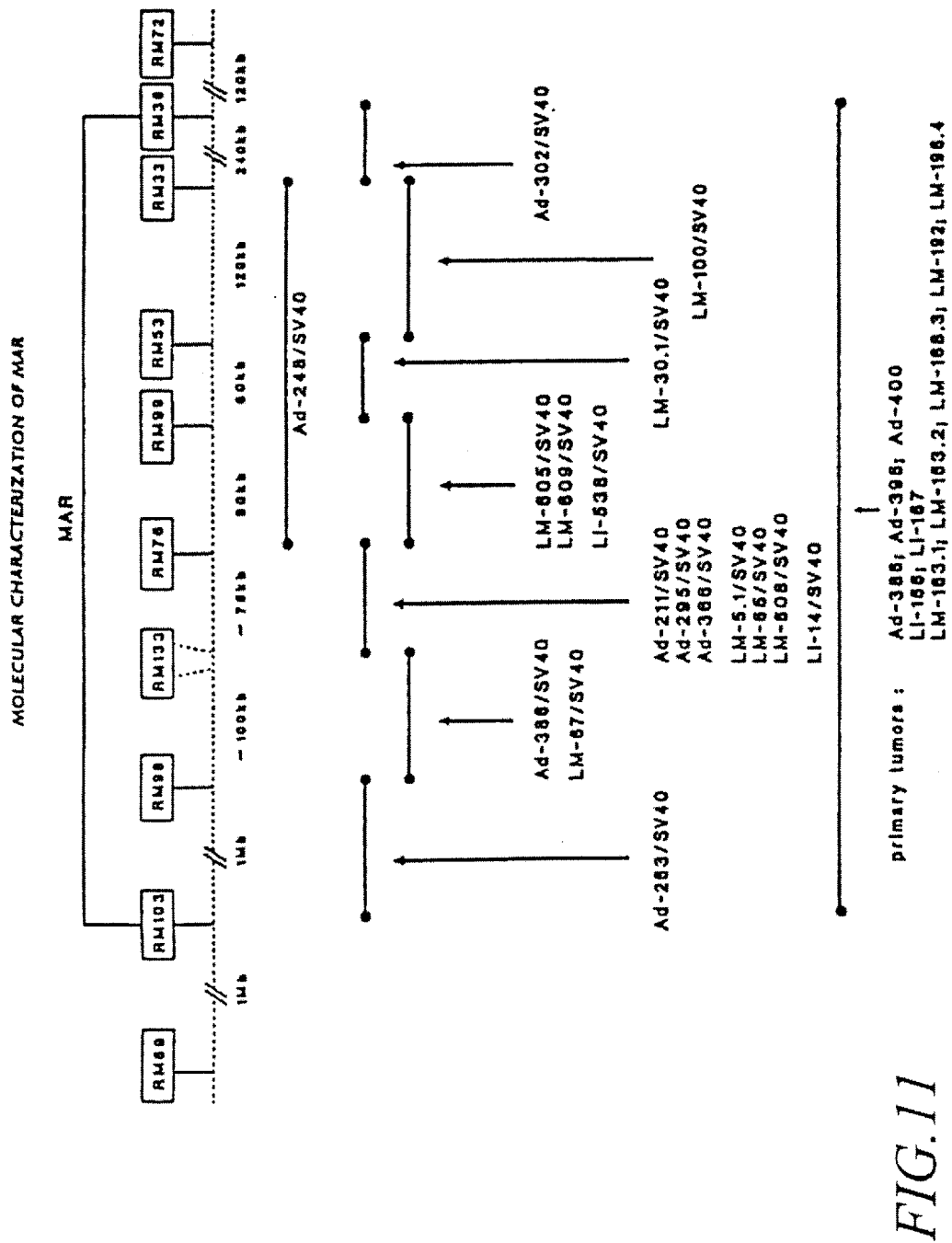
FIG. 11 is a schematic representation of chromosome 12 breakpoint mapping data obtained for primary pleomorphic salivary gland adenomas, uterine leiomyomas, and lipomas as well as cell lines derived from such solid tumors.

Column 52,
Line 3, "(see FIG. 3)" should read -- (see FIG. 11) --.
Line 40, "within MA" should read -- within MAR --.
Line 52, "in FIG. 3" should read -- in FIG. 11 --.

Column 53,
Line 55, between "it" and "would" delete period.

Column 57,
Line 17, "FIG. 1. Schematic" should read -- FIG. 9. Schematic --.
Line 36, "FIG. 2. a:" should read -- FIG. 10. a: --.
Line 47, "FIG. 3" should read -- FIG. 11. --.
Line 52, "sumitted" should read -- submitted --.

Column 58,
Line 1, "Eric F. P.X." should read -- Eric F.P.M. --.
Line 19, "cRM8S" should read -- cRM85 --.

Figure 12:
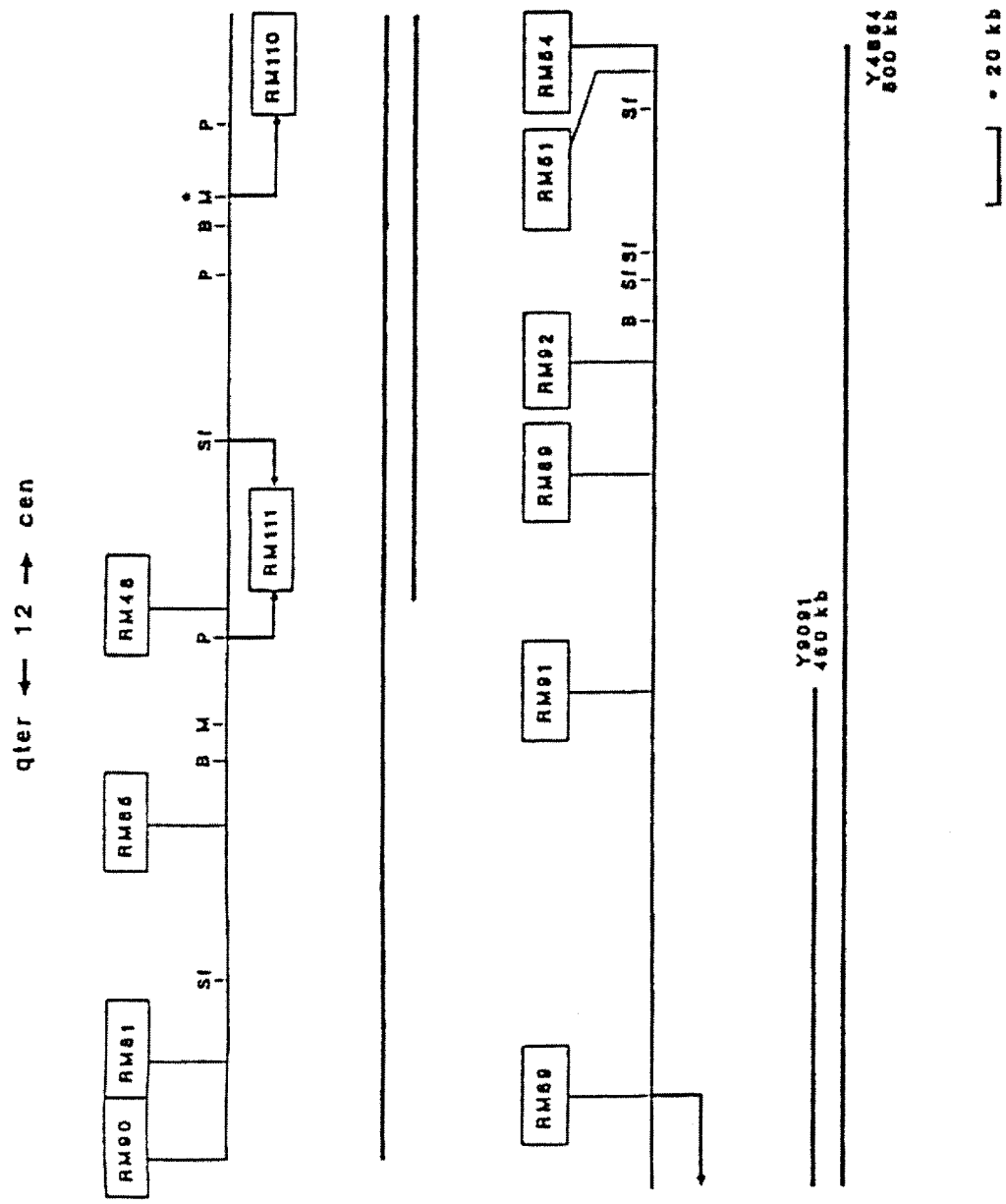
FIG. 12 is a composite physical map of the overlapping DNA inserts of YAC clones Y4854 and Y9091.

Column 59,
Line 47, "in FIG. 1" should read -- in FIG. 12 --.

Column 60,
Line 3, "(5)" should read -- [5] --.
Line 27, "(FIG. 1)" should read -- (FIG. 12) --.
Line 30, "in FIG. 1" should read -- in FIG 12 --.

UNITED STATES PATENT AND TRADEMARK OFFICE
CERTIFICATE OF CORRECTION

PATENT NO. : 6,544,784 B1
DATED : April 8, 2003
INVENTOR(S) : Jörn Bullerdiek et al.

Figure 13A:
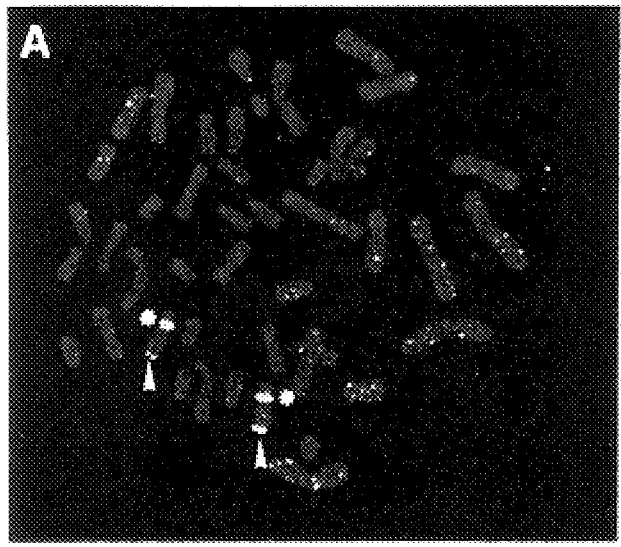
FIG. 13 is a depiction showing mapping of cosmid clone cPK12qter to the telomeric region of the long arm of chromosome 12, and FISH analysis of metaphase chromosomes of Ad-312/SV40 cells using DNA of YAC clone Y4584 or Y9091 as molecular probe.
Figure 13B:
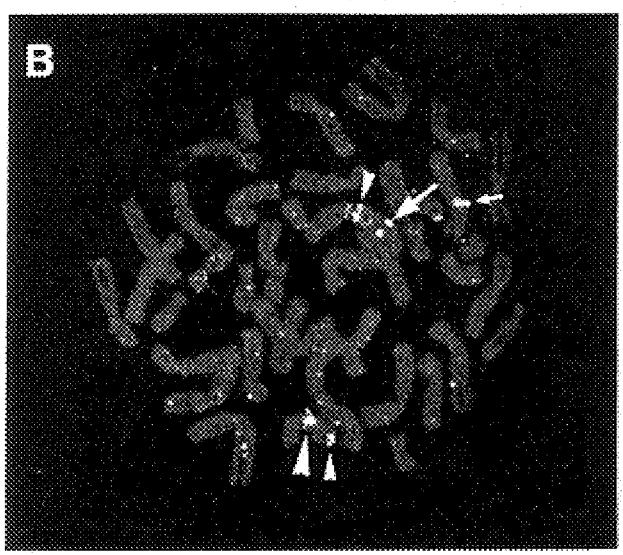
Figure 13C:
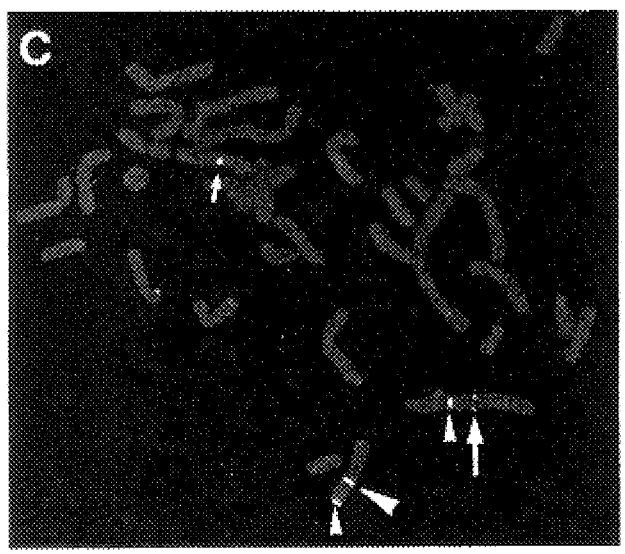
Figure 14A:
FIG. 14 is a depiction of FISH analysis of metaphase chromosomes of Ad- 312/SV40 cells using DNA cosmid clone cRM69 or RM111 as molecular probe.
Figure 14B:
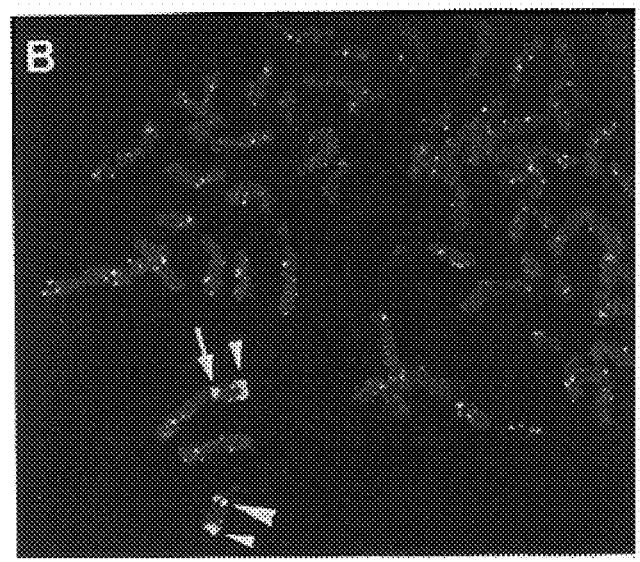

It is certified that error appears in the above-identified patent and that said Letters Patent is hereby corrected as shown below:

Column 61,
Line 17, "(FIG. 2A)" should read -- (FIG. 13A) --.
Line 22, "(FIG. 2B)" should read -- (FIG. 13B) --.
Line 22, "(FIG. 2C)" should read -- (FIG. 13C) --.
Line 29, "FIG. 2C" should read -- FIG. 13C --.
Line 38, "FIG. 1" should read -- FIG. 12 --.
Line 44, "Sv40" should read -- SV40 --.
Line 56, "FIG. 1" should read -- FIG. 12 --.
Line 59, "(FIG. 1)" should read -- (FIG. 12) --.
Line 60, "CRM110as" should read -- CRM110 as --.
Line 63, "FIG. 3A" should read -- FIG. 14A --.
Line 67, "FIG. 3B" should read -- FIG. 14B --.

Figure 15:
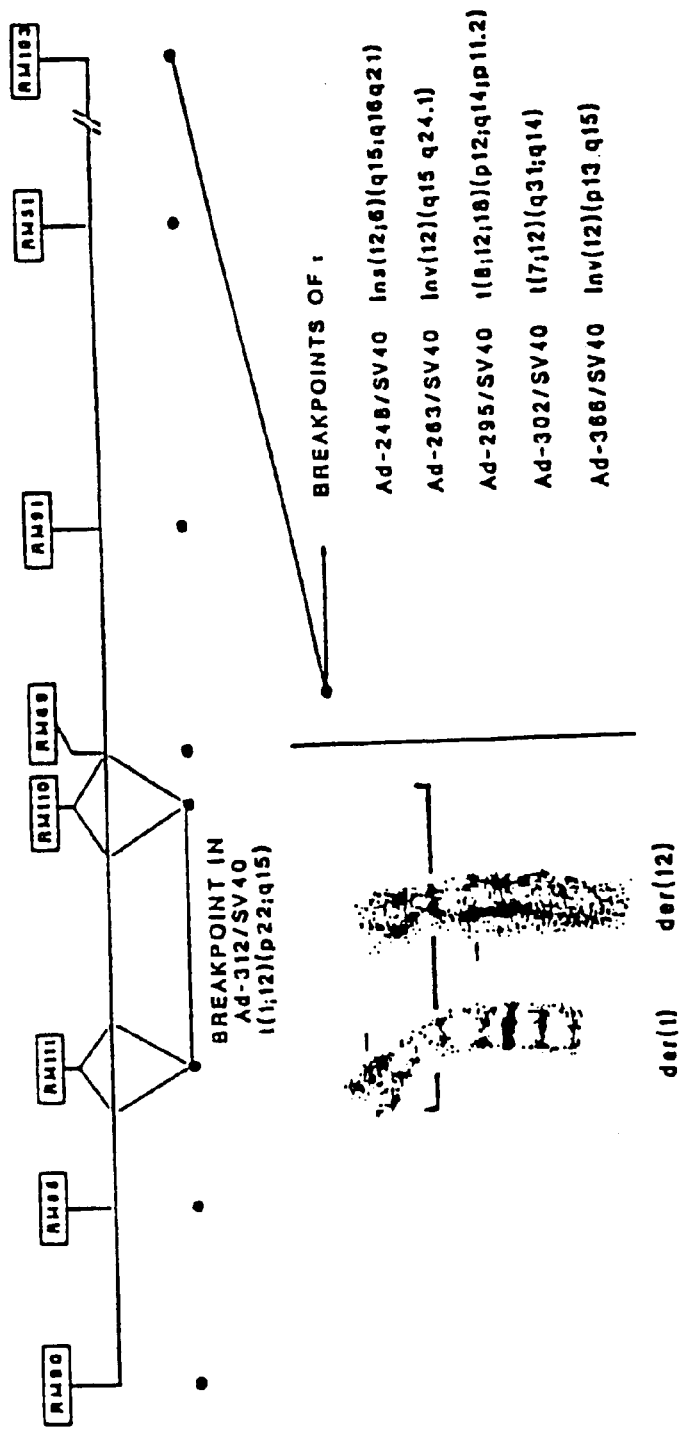
FIG. 15 is a schematic representation of FISH mapping data obtained for six pleomorphic salivary gland adenoma cell lines.

Column 62,
Lines 7, 13 and 17, "FIG. 4" should read -- FIG. 15 --.

Column 63,
Line 59, "[10]and" should read -- [10] and --.

Column 64,
Line 2, "onderzoekacties" should read -- Onderzoekacties --.

Column 65,
Line 54, "FIG. 1. Composite" should read -- FIG. 12. Composite --.

Column 66,
Line 11, "FIG. 2. A)" should read -- FIG. 13. A) --.
Line 28, "FIG. 3." should read -- FIG. 14. --.

UNITED STATES PATENT AND TRADEMARK OFFICE
CERTIFICATE OF CORRECTION

PATENT NO. : 6,544,784 B1
DATED : April 8, 2003
INVENTOR(S) : Jőrn Bullerdiek et al.

It is certified that error appears in the above-identified patent and that said Letters Patent is hereby corrected as shown below:

<u>Column 66, (continuation),</u>
Line 39, "FIG. 4." should read -- FIG. 15.--.
Line 53, "(p22; g15)" should read -- (p22; q15) --.

Signed and Sealed this

Seventeenth Day of August, 2004

JON W. DUDAS
*Acting Director of the United States Patent and Trademark Office*

```
                             SEQUENCE LISTING (1) GENERAL INFORMATION:

(iii) NUMBER OF SEQUENCES: 164

(2) INFORMATION FOR SEQ ID NO:1:
```

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:1:

AAGGATCCGT CGACATCTTT TTTTTTTTTT TTTT                                34

(2) INFORMATION FOR SEQ ID NO:2:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:2:

CUACUACUAC UAAAGGATCC GTCGACATC                                      29

(2) INFORMATION FOR SEQ ID NO:3:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:3:

CTTCAGCCCA GGGACAAC                                                  18

(2) INFORMATION FOR SEQ ID NO:4:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:4:

CAAGAGGCAG ACCTAGGA                                                  18

(2) INFORMATION FOR SEQ ID NO:5:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:5:

AACAATGCAA CTTTTAATTA CTG                                            23

(2) INFORMATION FOR SEQ ID NO:6:

(i) SEQUENCE CHARACTERISTICS:
        (A) LENGTH: 30 base pairs
        (B) TYPE: nucleic acid

```
        (C) STRANDEDNESS: single
        (D) TOPOLOGY: linear (ii) MOLECULE TYPE: Other (xi) SEQUENCE DESCRIPTION: SEQ ID NO:6:

CAUCAUCAUC AUCGCCTCAG AAGAGAGGAC                                            30

(2) INFORMATION FOR SEQ ID NO:7:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:7:

CAUCAUCAUC AUGTTCAGAA GAAGCCTGCT                                            30

(2) INFORMATION FOR SEQ ID NO:8:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:8:

CAUCAUCAUC AUTTGATCTG ATAAGCAAGA GTGGG                                      35

(2) INFORMATION FOR SEQ ID NO:9:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:9:

CTCCAAGACA GGCCTCTGAT G                                                     21

(2) INFORMATION FOR SEQ ID NO:10:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:10:

ACCACAGGTC CCCTTCAAAC TA                                                    22

(2) INFORMATION FOR SEQ ID NO:11:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:11:

TCCTCCTGAG CAGGCTTC                                                         18
```

(2) INFORMATION FOR SEQ ID NO:12:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:12:

CTTCAGCCCA GGGACAAC                                                          18

(2) INFORMATION FOR SEQ ID NO:13:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:13:

CGCCTCAGAA GAGAGGAC                                                          18

(2) INFORMATION FOR SEQ ID NO:14:

(i) SEQUENCE CHARACTERISTICS:
        (A) LENGTH: 25 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:14:

Ala Arg Gly Glu Gly Ala Gly Gln Pro Ser Thr Ser Ala Gln Gly Gln
 1               5                  10                  15

Pro Ala Ala Pro Ala Pro Gln Lys Arg
            20                  25

(2) INFORMATION FOR SEQ ID NO:15:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:15:

Ser Pro Ser Lys Ala Ala Gln Lys Lys Ala Glu Ala Thr Gly Glu Lys
 1               5                  10                  15

Arg (2) INFORMATION FOR SEQ ID NO:16:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:16:

Pro Arg Lys Trp Pro Gln Gln Val Val Gln Lys Lys Pro Ala Gln Glu
 1               5                  10                  15

Glu (2) INFORMATION FOR SEQ ID NO:17:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:17:

```
TGGGACTAAC GGATTTTCAA                                             20
```

(2) INFORMATION FOR SEQ ID NO:18:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:18:

```
TGTGGTTCAT TCATGCATTA                                             20
```

(2) INFORMATION FOR SEQ ID NO:19:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:19:

```
TCCATCATCA TCTCAAAACA                                             20
```

(2) INFORMATION FOR SEQ ID NO:20:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:20:

```
CTCTACCAAA TGGAATAAAC AG                                          22
```

(2) INFORMATION FOR SEQ ID NO:21:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:21:

```
GCAGCTCAGG CTCCTTCCCA                                             20
```

(2) INFORMATION FOR SEQ ID NO:22:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:22:

```
TGGCTTCCTG AAACGCGAGA                                             20
```

(2) INFORMATION FOR SEQ ID NO:23:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:23:

```
TCTCCACTGC TTCCATTCAC                                           20
```

(2) INFORMATION FOR SEQ ID NO:24:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:24:

```
ACACAAAACC ACTGGGGTCT                                           20
```

(2) INFORMATION FOR SEQ ID NO:25:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:25:

```
CAGCTTTGGA ATCAGTGAGG                                           20
```

(2) INFORMATION FOR SEQ ID NO:26:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:26:

```
CCTGGGGAAG AGGAGTAAAG                                           20
```

(2) INFORMATION FOR SEQ ID NO:27:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:27:

```
GAGCTTCCTA TCTCATCC                                             18
```

(2) INFORMATION FOR SEQ ID NO:28:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:28:

```
ATGCTTGTGT GTGAGTGG                                             18
```

(2) INFORMATION FOR SEQ ID NO:29:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:29:

TTTGCTAAGC TAGGTGCC                                          18

(2) INFORMATION FOR SEQ ID NO:30:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:30:

AGCTTCAAGA CCCATGAG                                          18

(2) INFORMATION FOR SEQ ID NO:31:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:31:

CAGTTCTGAG ACTGCTTG                                          18

(2) INFORMATION FOR SEQ ID NO:32:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:32:

TAATAGCAGG GACTCAGC                                          18

(2) INFORMATION FOR SEQ ID NO:33:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:33:

CTTGTCTCAT TCTTTTAAAG GG                                   22

(2) INFORMATION FOR SEQ ID NO:34:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:34:

CACCCCTTTT TAGATCCTAC                                     20

(2) INFORMATION FOR SEQ ID NO:35:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:35:

GAATGTTCAT CACAGTGCTG                                           20

(2) INFORMATION FOR SEQ ID NO:36:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:36:

AATGTGAGGT TCTGCTGAAG                                           20

(2) INFORMATION FOR SEQ ID NO:37:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:37:

TTCTCATGGG GTAAGGACAG                                           20

(2) INFORMATION FOR SEQ ID NO:38:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:38:

AAAGCTGCTT ATATAGGGAA TC                                        22

(2) INFORMATION FOR SEQ ID NO:39:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:39:

CCTTGGCTTA GATATGATAC AC                                        22

(2) INFORMATION FOR SEQ ID NO:40:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:40:

GCTCTTCAGA AATATCCTAT GG                                        22

(2) INFORMATION FOR SEQ ID NO:41:

(i) SEQUENCE CHARACTERISTICS:
           (A) LENGTH: 20 base pairs
           (B) TYPE: nucleic acid
           (C) STRANDEDNESS: single
           (D) TOPOLOGY: linear (xi) SEQUENCE DESCRIPTION: SEQ ID NO:41:

CCTTAGCAGT TGCTTGTCTG                                            20

(2) INFORMATION FOR SEQ ID NO:42:

(i) SEQUENCE CHARACTERISTICS:
           (A) LENGTH: 20 base pairs
           (B) TYPE: nucleic acid
           (C) STRANDEDNESS: single
           (D) TOPOLOGY: linear (xi) SEQUENCE DESCRIPTION: SEQ ID NO:42:

TCGTCACAGG ACATAGTCAC                                            20

(2) INFORMATION FOR SEQ ID NO:43:

(i) SEQUENCE CHARACTERISTICS:
           (A) LENGTH: 23 base pairs
           (B) TYPE: nucleic acid
           (C) STRANDEDNESS: single
           (D) TOPOLOGY: linear (xi) SEQUENCE DESCRIPTION: SEQ ID NO:43:

TCTATGGTAT GTTATACAAG ATG                                        23

(2) INFORMATION FOR SEQ ID NO:44:

(i) SEQUENCE CHARACTERISTICS:
           (A) LENGTH: 19 base pairs
           (B) TYPE: nucleic acid
           (C) STRANDEDNESS: single
           (D) TOPOLOGY: linear (xi) SEQUENCE DESCRIPTION: SEQ ID NO:44:

CAGTGAGATC CTGTCTCTA                                             19

(2) INFORMATION FOR SEQ ID NO:45:

(i) SEQUENCE CHARACTERISTICS:
           (A) LENGTH: 24 base pairs
           (B) TYPE: nucleic acid
           (C) STRANDEDNESS: single
           (D) TOPOLOGY: linear (xi) SEQUENCE DESCRIPTION: SEQ ID NO:45:

TCTGTGATGT TTTAAGCCAC TTAG                                       24

(2) INFORMATION FOR SEQ ID NO:46:

(i) SEQUENCE CHARACTERISTICS:
           (A) LENGTH: 20 base pairs
           (B) TYPE: nucleic acid
           (C) STRANDEDNESS: single
           (D) TOPOLOGY: linear (xi) SEQUENCE DESCRIPTION: SEQ ID NO:46:

AATTCTGTGT CCCTGCCACC                                            20

(2) INFORMATION FOR SEQ ID NO:47:

(i) SEQUENCE CHARACTERISTICS:

```
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:47:

ATTCTTCCTC ACCTCCCACC                                              20

(2) INFORMATION FOR SEQ ID NO:48:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:48:

AATCTGCAGA GAGGTCCAGC                                              20

(2) INFORMATION FOR SEQ ID NO:49:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:49:

AATTCTCCAT CTGGGCCTGG                                              20

(2) INFORMATION FOR SEQ ID NO:50:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:50:

GAACGCTAAG CATGTGGGAG                                              20

(2) INFORMATION FOR SEQ ID NO:51:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:51:

CTCCAACCAT GGTCCAAAAC                                              20

(2) INFORMATION FOR SEQ ID NO:52:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:52:

GACCTCCAGT GGCTCTTTAG                                              20

(2) INFORMATION FOR SEQ ID NO:53:

(i) SEQUENCE CHARACTERISTICS:
        (A) LENGTH: 20 base pairs
```

(B) TYPE: nucleic acid
        (C) STRANDEDNESS: single
        (D) TOPOLOGY: linear (xi) SEQUENCE DESCRIPTION: SEQ ID NO:53:

ACCATCAGAT CTGGCACTGA                                                    20

(2) INFORMATION FOR SEQ ID NO:54:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:54:

TTACATTGGA GCTGTCATGC                                                    20

(2) INFORMATION FOR SEQ ID NO:55:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:55:

TCCAGGACAT CCTGAAAATG                                                    20

(2) INFORMATION FOR SEQ ID NO:56:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:56:

AGTATCCTGC ACTTCTGCAG                                                    20

(2) INFORMATION FOR SEQ ID NO:57:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:57:

GATGAACTCT GAGGTGCCTT C                                                  21

(2) INFORMATION FOR SEQ ID NO:58:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:58:

TCAAACCCAG CTTTGACTCC                                                    20

(2) INFORMATION FOR SEQ ID NO:59:

(i) SEQUENCE CHARACTERISTICS:
        (A) LENGTH: 20 base pairs
        (B) TYPE: nucleic acid (C) STRANDEDNESS: single
        (D) TOPOLOGY: linear (xi) SEQUENCE DESCRIPTION: SEQ ID NO:59:

GTCTTCAAAA CGCTTTCCTG                                                        20

(2) INFORMATION FOR SEQ ID NO:60:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:60:

TGGTTTGCAT AATGGTGATG                                                        20

(2) INFORMATION FOR SEQ ID NO:61:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:61:

TACACTACTC TGCAGCACAC                                                        20

(2) INFORMATION FOR SEQ ID NO:62:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:62:

TCTGAGTCAA TCACATGTCC                                                        20

(2) INFORMATION FOR SEQ ID NO:63:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:63:

CTCCCCAGAT GATCTCTTTC                                                        20

(2) INFORMATION FOR SEQ ID NO:64:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:64:

CGGTAGGAAA TAAAGGAGAG                                                        20

(2) INFORMATION FOR SEQ ID NO:65:

(i) SEQUENCE CHARACTERISTICS:
        (A) LENGTH: 20 base pairs
        (B) TYPE: nucleic acid
        (C) STRANDEDNESS: single (D) TOPOLOGY: linear (xi) SEQUENCE DESCRIPTION: SEQ ID NO:65:

TATTTACTAG CTGGCCTTGG                                          20

(2) INFORMATION FOR SEQ ID NO:66:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:66:

CATCTCAGGC ACACACAATG                                          20

(2) INFORMATION FOR SEQ ID NO:67:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:67:

ATTCAGAGAA GTGGCCAAGT                                          20

(2) INFORMATION FOR SEQ ID NO:68:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:68:

GGGATAGGTC TTCTGCAATC                                          20

(2) INFORMATION FOR SEQ ID NO:69:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:69:

TCCAACAATA CTGAGTGACC                                          20

(2) INFORMATION FOR SEQ ID NO:70:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:70:

TCCATTTCAC TGTAGCACTG                                          20

(2) INFORMATION FOR SEQ ID NO:71:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:71:

GTAATCAACC ATTCCCCTGA                                            20

(2) INFORMATION FOR SEQ ID NO:72:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (xi) SEQUENCE DESCRIPTION: SEQ ID NO:72:

AAAATAGCTG GTATGGTGGC                                            20

(2) INFORMATION FOR SEQ ID NO:73:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (xi) SEQUENCE DESCRIPTION: SEQ ID NO:73:

ACTGCTCTAG TTTTCAAGGA                                            20

(2) INFORMATION FOR SEQ ID NO:74:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (xi) SEQUENCE DESCRIPTION: SEQ ID NO:74:

AATTTACCTG ACAGTTTCCT                                            20

(2) INFORMATION FOR SEQ ID NO:75:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (xi) SEQUENCE DESCRIPTION: SEQ ID NO:75:

GCATTTGACG TCCAATATTG                                            20

(2) INFORMATION FOR SEQ ID NO:76:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (xi) SEQUENCE DESCRIPTION: SEQ ID NO:76:

ATTCCATTGG CTAACACAAG                                            20

(2) INFORMATION FOR SEQ ID NO:77:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (xi) SEQUENCE DESCRIPTION: SEQ ID NO:77:

GCAAAACTTT GACTGAAACG                                      20

(2) INFORMATION FOR SEQ ID NO:78:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:78:

CACAGAGTAT CGCACTGCAT                                      20

(2) INFORMATION FOR SEQ ID NO:79:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:79:

AAGAGATTTC CCATGTTGTG                                      20

(2) INFORMATION FOR SEQ ID NO:80:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:80:

CTAGTGCCTT CACAAGAACC                                      20

(2) INFORMATION FOR SEQ ID NO:81:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:81:

AATTCTTGAG GGGTTCACTG                                      20

(2) INFORMATION FOR SEQ ID NO:82:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:82:

TCCACACTGA GAGCTTTTCA                                      20

(2) INFORMATION FOR SEQ ID NO:83:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:83:

```
GTGGTTCTGT ACAGCAGTGG                                              20

(2) INFORMATION FOR SEQ ID NO:84:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (xi) SEQUENCE DESCRIPTION: SEQ ID NO:84:

TGAGAAAATG TCTGCCAAAT                                              20

(2) INFORMATION FOR SEQ ID NO:85:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (xi) SEQUENCE DESCRIPTION: SEQ ID NO:85:

GCTCTACCAG GCATACAGTG                                              20

(2) INFORMATION FOR SEQ ID NO:86:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (xi) SEQUENCE DESCRIPTION: SEQ ID NO:86:

ATTCCTAGCA TCTTTTCACG                                              20

(2) INFORMATION FOR SEQ ID NO:87:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (xi) SEQUENCE DESCRIPTION: SEQ ID NO:87:

ATATGCATTA GGCTCAACCC                                              20

(2) INFORMATION FOR SEQ ID NO:88:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (xi) SEQUENCE DESCRIPTION: SEQ ID NO:88:

ATCCCACAGG TCAACATGAC                                              20

(2) INFORMATION FOR SEQ ID NO:89:

(i) SEQUENCE CHARACTERISTICS:
         (A) LENGTH: 25 base pairs
         (B) TYPE: nucleic acid
         (C) STRANDEDNESS: single
         (D) TOPOLOGY: linear (xi) SEQUENCE DESCRIPTION: SEQ ID NO:89:
```

```
ATCCTTACAT TTCCAGTGGC ATTCA                                          25

(2) INFORMATION FOR SEQ ID NO:90:

(i) SEQUENCE CHARACTERISTICS:
          (A) LENGTH: 23 base pairs
          (B) TYPE: nucleic acid
          (C) STRANDEDNESS: single
          (D) TOPOLOGY: linear (xi) SEQUENCE DESCRIPTION: SEQ ID NO:90:

CCCAGAAGAC CCACATTCCT CAT                                            23

(2) INFORMATION FOR SEQ ID NO:91:

(i) SEQUENCE CHARACTERISTICS:
          (A) LENGTH: 25 base pairs
          (B) TYPE: nucleic acid
          (C) STRANDEDNESS: single
          (D) TOPOLOGY: linear (xi) SEQUENCE DESCRIPTION: SEQ ID NO:91:

TTTTAAGTTT CTCCAGGGAG GAGAC                                          25

(2) INFORMATION FOR SEQ ID NO:92:

(i) SEQUENCE CHARACTERISTICS:
          (A) LENGTH: 25 base pairs
          (B) TYPE: nucleic acid
          (C) STRANDEDNESS: single
          (D) TOPOLOGY: linear (xi) SEQUENCE DESCRIPTION: SEQ ID NO:92:

AATAGGCTCT TTGGAAAGCT GGAGT                                          25

(2) INFORMATION FOR SEQ ID NO:93:

(i) SEQUENCE CHARACTERISTICS:
          (A) LENGTH: 26 base pairs
          (B) TYPE: nucleic acid
          (C) STRANDEDNESS: single
          (D) TOPOLOGY: linear (xi) SEQUENCE DESCRIPTION: SEQ ID NO:93:

TCTCAGCTTA ATCCAAGAAG GACTTC                                         26

(2) INFORMATION FOR SEQ ID NO:94:

(i) SEQUENCE CHARACTERISTICS:
          (A) LENGTH: 26 base pairs
          (B) TYPE: nucleic acid
          (C) STRANDEDNESS: single
          (D) TOPOLOGY: linear (xi) SEQUENCE DESCRIPTION: SEQ ID NO:94:

GGCATATTCC TCAACAATTT ATGCTT                                         26

(2) INFORMATION FOR SEQ ID NO:95:

(i) SEQUENCE CHARACTERISTICS:
          (A) LENGTH: 25 base pairs
          (B) TYPE: nucleic acid
          (C) STRANDEDNESS: single
          (D) TOPOLOGY: linear (xi) SEQUENCE DESCRIPTION: SEQ ID NO:95:

TGGAGAAGCT ATGGTGCTTC CTATG                                          25
```

(2) INFORMATION FOR SEQ ID NO:96:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO:96:

TGACAAATAG GTGAGGGAAA GTTGTTAT                                    28

(2) INFORMATION FOR SEQ ID NO:97:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:97:

TCACACGCTG AATCAATCTT                                            20

(2) INFORMATION FOR SEQ ID NO:98:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:98:

CAGCAGCTGA TACAAGCTTT                                            20

(2) INFORMATION FOR SEQ ID NO:99:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:99:

TGTTTTCTTT CCCGATAGGT                                            20

(2) INFORMATION FOR SEQ ID NO:100:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:100:

CTGGGATGCT CTTCGACCTC                                            20

(2) INFORMATION FOR SEQ ID NO:101:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:101:

CCATCCAACA TCTTAAATGG AC                                        22

(2) INFORMATION FOR SEQ ID NO:102:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:102:

CAGCTGCAAA CTCTAGGACT ATT                                                    23

(2) INFORMATION FOR SEQ ID NO:103:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:103:

TAGGAAATGG                                                                   10

(2) INFORMATION FOR SEQ ID NO:104:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:104:

GTGAGTAATA                                                                   10

(2) INFORMATION FOR SEQ ID NO:105:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:105:

AATACTCTGG                                                                   10

(2) INFORMATION FOR SEQ ID NO:106:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:106:

CCTACTATTG                                                                   10

(2) INFORMATION FOR SEQ ID NO:107:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:107:

GGAAGTGTGA                                                                   10

(2) INFORMATION FOR SEQ ID NO:108:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:108:

AACACAGGAC          10

(2) INFORMATION FOR SEQ ID NO:109:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:109:

GTTTAATATT          10

(2) INFORMATION FOR SEQ ID NO:110:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:110:

AAGAAGGCAG          10

(2) INFORMATION FOR SEQ ID NO:111:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:111:

TAGGAGGTAG          10

(2) INFORMATION FOR SEQ ID NO:112:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:112:

GGTGGCCATT          10

(2) INFORMATION FOR SEQ ID NO:113:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:113:

GACAATCTAC          10

(2) INFORMATION FOR SEQ ID NO:114:

(i) SEQUENCE CHARACTERISTICS:
    (A) LENGTH: 10 base pairs
    (B) TYPE: nucleic acid
    (C) STRANDEDNESS: single
    (D) TOPOLOGY: linear (xi) SEQUENCE DESCRIPTION: SEQ ID NO:114:

GTACAGAAGA                                                              10

(2) INFORMATION FOR SEQ ID NO:115:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:115:

GGGCATTCAG                                                              10

(2) INFORMATION FOR SEQ ID NO:116:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:116:

GCAGTCTGTA                                                              10

(2) INFORMATION FOR SEQ ID NO:117:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:117:

TCTGTATCCT                                                              10

(2) INFORMATION FOR SEQ ID NO:118:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:118:

ACACACTTCC                                                              10

(2) INFORMATION FOR SEQ ID NO:119:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:119:

ATATTATGGA                                                              10

(2) INFORMATION FOR SEQ ID NO:120:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (xi) SEQUENCE DESCRIPTION: SEQ ID NO:120:

GAGGAGTTTT                                                              10

(2) INFORMATION FOR SEQ ID NO:121:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (xi) SEQUENCE DESCRIPTION: SEQ ID NO:121:

TAACACAGGA                                                              10

(2) INFORMATION FOR SEQ ID NO:122:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (xi) SEQUENCE DESCRIPTION: SEQ ID NO:122:

TTACCTGCTG                                                              10

(2) INFORMATION FOR SEQ ID NO:123:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (xi) SEQUENCE DESCRIPTION: SEQ ID NO:123:

GCTGGAGTGC                                                              10

(2) INFORMATION FOR SEQ ID NO:124:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (xi) SEQUENCE DESCRIPTION: SEQ ID NO:124:

GTCTCCTCCC                                                              10

(2) INFORMATION FOR SEQ ID NO:125:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (xi) SEQUENCE DESCRIPTION: SEQ ID NO:125:

TTTNTCTCTT                                                              10

(2) INFORMATION FOR SEQ ID NO:126:

(i) SEQUENCE CHARACTERISTICS:

```
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:126:

AGTCCAAGAA                                                              10

(2) INFORMATION FOR SEQ ID NO:127:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:127:

CCAAACTCTG                                                              10

(2) INFORMATION FOR SEQ ID NO:128:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:128:

CTCCAGAAAC                                                              10

(2) INFORMATION FOR SEQ ID NO:129:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:129:

AACTTCTTGA                                                              10

(2) INFORMATION FOR SEQ ID NO:130:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:130:

GAATGTCAGA                                                              10

(2) INFORMATION FOR SEQ ID NO:131:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:131:

CCTGGAAGCT                                                              10

(2) INFORMATION FOR SEQ ID NO:132:

(i) SEQUENCE CHARACTERISTICS:
        (A) LENGTH: 10 base pairs
```

(B) TYPE: nucleic acid
        (C) STRANDEDNESS: single
        (D) TOPOLOGY: linear (xi) SEQUENCE DESCRIPTION: SEQ ID NO:132:

ATGGAGTCTC                                                              10

(2) INFORMATION FOR SEQ ID NO:133:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:133:

TTCCAGATAC                                                              10

(2) INFORMATION FOR SEQ ID NO:134:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:134:

GCCTGCTCAG                                                              10

(2) INFORMATION FOR SEQ ID NO:135:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:135:

TATCCTTTCA                                                              10

(2) INFORMATION FOR SEQ ID NO:136:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:136:

TCTTTCCACT                                                              10

(2) INFORMATION FOR SEQ ID NO:137:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:137:

ATACCACTTA                                                              10

(2) INFORMATION FOR SEQ ID NO:138:

(i) SEQUENCE CHARACTERISTICS:
        (A) LENGTH: 10 base pairs
        (B) TYPE: nucleic acid

```
            (C) STRANDEDNESS: single
            (D) TOPOLOGY: linear (xi) SEQUENCE DESCRIPTION: SEQ ID NO:138:

TTGCCATGGT                                                          10

(2) INFORMATION FOR SEQ ID NO:139:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (xi) SEQUENCE DESCRIPTION: SEQ ID NO:139:

CACTTTCATC                                                          10

(2) INFORMATION FOR SEQ ID NO:140:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (xi) SEQUENCE DESCRIPTION: SEQ ID NO:140:

ATAAGGACTA                                                          10

(2) INFORMATION FOR SEQ ID NO:141:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (xi) SEQUENCE DESCRIPTION: SEQ ID NO:141:

NCTTGTNAGC                                                          10

(2) INFORMATION FOR SEQ ID NO:142:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (xi) SEQUENCE DESCRIPTION: SEQ ID NO:142:

GTAAGACATA                                                          10

(2) INFORMATION FOR SEQ ID NO:143:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (xi) SEQUENCE DESCRIPTION: SEQ ID NO:143:

GTCAATGTTG                                                          10

(2) INFORMATION FOR SEQ ID NO:144:

(i) SEQUENCE CHARACTERISTICS:
            (A) LENGTH: 10 base pairs
            (B) TYPE: nucleic acid
            (C) STRANDEDNESS: single
```

```
        (D) TOPOLOGY: linear (xi) SEQUENCE DESCRIPTION: SEQ ID NO:144:

TCCTGGTACC                                                              10

(2) INFORMATION FOR SEQ ID NO:145:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:145:

TCTTTCAGAT                                                              10

(2) INFORMATION FOR SEQ ID NO:146:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:146:

AATTACCTCT                                                              10

(2) INFORMATION FOR SEQ ID NO:147:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:147:

GACTGACTCA                                                              10

(2) INFORMATION FOR SEQ ID NO:148:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:148:

TATTCCTGAA                                                              10

(2) INFORMATION FOR SEQ ID NO:149:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:149:

GTCAATGTTG                                                              10

(2) INFORMATION FOR SEQ ID NO:150:

(i) SEQUENCE CHARACTERISTICS:
        (A) LENGTH: 10 base pairs
        (B) TYPE: nucleic acid
        (C) STRANDEDNESS: single
        (D) TOPOLOGY: linear
```

```
    (xi) SEQUENCE DESCRIPTION: SEQ ID NO:150:

AATTACCTCT                                                              10

(2) INFORMATION FOR SEQ ID NO:151:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:151:

GCTTTTTCAA                                                              10

(2) INFORMATION FOR SEQ ID NO:152:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:152:

GTTAAGAAAC                                                              10

(2) INFORMATION FOR SEQ ID NO:153:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:153:

GNCTGACTAC                                                              10

(2) INFORMATION FOR SEQ ID NO:154:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:154:

AAGTCAAGAG                                                              10

(2) INFORMATION FOR SEQ ID NO:155:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:155:

TTTTAAAACA                                                              10

(2) INFORMATION FOR SEQ ID NO:156:

(i) SEQUENCE CHARACTERISTICS:
        (A) LENGTH: 10 base pairs
        (B) TYPE: nucleic acid
        (C) STRANDEDNESS: single
        (D) TOPOLOGY: linear
```

(xi) SEQUENCE DESCRIPTION: SEQ ID NO:156:

AATCTGAAAT                                                                10

(2) INFORMATION FOR SEQ ID NO:157:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:157:

ATATGGCAAG                                                                10

(2) INFORMATION FOR SEQ ID NO:158:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:158:

TCAGGCATCA                                                                10

(2) INFORMATION FOR SEQ ID NO:159:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:159:

TAGAGATTAG                                                                10

(2) INFORMATION FOR SEQ ID NO:160:

(i) SEQUENCE CHARACTERISTICS:
        (A) LENGTH: 1033 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:160:

CGCTTCAGAA GAGAGGACGC GGCCGCCCCA GGAAGCAGCA GCAAAAACCA ACCGGTGAGC        60

CCTCTCCTAA GAGACCCAGG GGAAGACCCA AAGGCAGCAA AAACAAGAGT CCCTCTAAAG       120

CAGCTCAAGA GGAAGCAGAA GCCACTGAAG AAAAACGGCC AAGGGGCAGA CCTAGGAAAT       180

GGGGTGGCCA TTCAGGGCAA CTGGGGCCTT CGTCAGTTGC CCCTTCATTC CGCCCAGAGG       240

ATGAGCTTGA GCACCTGACC AAAAAGATGC TGTATGACAT GGAAAATCCA CCTGCTGACG       300

AATACTTTGG CCGCTGTGCT CGCTGTGGAG AAAACGTAGT TGGGAAGGT ACAGGATGCA        360

CTGCCATGGA TCAGGTCTTC CACGTGGATT GTTTTACCTG CATCATCTGC AACAACAAGC       420

TCCGAGGGCA GCCATTCTAT GCTGTGGAAA AGAAAGCATA CTGCGAGCCC TGCTACATTA       480

ATACTCTGGA GCAGTGCAAT GTGTGTTCCA AGCCCATCAT GGAGCGGATT CTCCGAGCCA       540

CCGGGAAGGC CTATCATCCT CACTGTTTCA CCTGCGTGAT GTGCCACCGC AGCCTGGATG       600

GGATCCCATT CACTGTGGAT GCTGGCGGGC TCATTCACTG CATTGAGGAC TTCCACAAGA       660

AATTTGCCCC GCGGTGTTCT GTGTGCAAGG AGCCTATTAT GCCAGCCCCG GGCCAGGAGG       720

```
AGACTGTCCG TATTGTGGCT TTGGATCGAG ATTTCCATGT TCACTGCTAC CGATGCGAGG    780

ATTGCGGTGG TCTCCTGTCT GAAGGAGATA ACCAAGGCTG CTACCCCTTG GATGGGCACA    840

TCCTCTGCAA GACCTGCAAC TCTGCCCGCA TCAGGGTGTT GACCGCCAAG GCGAGCACTG    900

ACCTTTAGAT TCAGTCACCT GTTCAGCCGG CACTGAGAAG AACGAACACA AGAAAAAGAT    960

AAGAAATACT AGAGTAAAGG CCATCAAACT ACGCGAAAAA AAAAAAAAAA AAAAAAGATG   1020

TCGACGGATC CTT                                                     1033
```

(2) INFORMATION FOR SEQ ID NO:161:

(i) SEQUENCE CHARACTERISTICS:
        (A) LENGTH: 343 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:161:

```
Leu Gln Lys Arg Gly Arg Gly Arg Pro Arg Lys Gln Gln Lys Pro
 1               5                  10                  15

Thr Gly Glu Pro Ser Pro Lys Arg Pro Arg Gly Arg Pro Lys Gly Ser
                20                  25                  30

Lys Asn Lys Ser Pro Ser Lys Ala Ala Gln Glu Glu Ala Glu Ala Thr
                35                  40                  45

Glu Glu Lys Arg Pro Arg Gly Arg Pro Arg Lys Trp Gly Gly His Ser
        50                  55                  60

Gly Gln Leu Gly Pro Ser Ser Val Ala Pro Ser Phe Arg Pro Glu Asp
 65                  70                  75                  80

Glu Leu Glu His Leu Thr Lys Lys Met Leu Tyr Asp Met Glu Asn Pro
                    85                  90                  95

Pro Ala Asp Glu Tyr Phe Gly Arg Cys Ala Arg Cys Gly Glu Asn Val
                100                 105                 110

Val Gly Glu Gly Thr Gly Cys Thr Ala Met Asp Gln Val Phe His Val
                115                 120                 125

Asp Cys Phe Thr Cys Ile Ile Cys Asn Asn Lys Leu Arg Gly Gln Pro
    130                 135                 140

Phe Tyr Ala Val Glu Lys Lys Ala Tyr Cys Glu Pro Cys Tyr Ile Asn
145                 150                 155                 160

Thr Leu Glu Gln Cys Asn Val Cys Ser Lys Pro Ile Met Glu Arg Ile
                    165                 170                 175

Leu Arg Ala Thr Gly Lys Ala Tyr His Pro His Cys Phe Thr Cys Val
                180                 185                 190

Met Cys His Arg Ser Leu Asp Gly Ile Pro Phe Thr Val Asp Ala Gly
            195                 200                 205

Gly Leu Ile His Cys Ile Glu Asp Phe His Lys Lys Phe Ala Pro Arg
    210                 215                 220

Cys Ser Val Cys Lys Glu Pro Ile Met Pro Ala Pro Gly Gln Glu Glu
225                 230                 235                 240

Thr Val Arg Ile Val Ala Leu Asp Arg Asp Phe His Val His Cys Tyr
                    245                 250                 255

Arg Cys Glu Asp Cys Gly Gly Leu Leu Ser Glu Gly Asp Asn Gln Gly
                260                 265                 270

Cys Tyr Pro Leu Asp Gly His Ile Leu Cys Lys Thr Cys Asn Ser Ala
            275                 280                 285
```

```
Arg Ile Arg Val Leu Thr Ala Lys Ala Ser Thr Asp Leu Xaa Ile Gln
    290                 295                 300

Ser Pro Val Gln Pro Ala Leu Arg Arg Thr Asn Thr Arg Lys Arg Xaa
305                 310                 315                 320

Glu Ile Leu Glu Xaa Arg Pro Ser Asn Tyr Ala Lys Lys Lys Lys
                325                 330                 335

Lys Lys Asp Val Asp Gly Ser
            340

(2) INFORMATION FOR SEQ ID NO:162:

(i) SEQUENCE CHARACTERISTICS:
        (A) LENGTH: 4323 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:162:

GTCACTTTTA TTTGGGGGTG TGGACAGCTG CTTTCCCAGG GGAGTACTTC TTACAGTGGG      60

ATTTCAAGAC AAGATCGGCC TGAAGAAAAA TTATATTTGT ATATTTTTTA AAAAGTGGGA     120

ACTTTGAGGC TCAGAGACAG AGCAGAAGAC AGAACCTGGT CTTCTGATTC CCTGTGTTCT     180

GCTTTTTTCA TTGTTCCACT GGACGCTCAT CAGAGGGAAG ATCTTTTTCC TCAATTGATT     240

CCAACAATGT CTCACCCATC TTGGCTGCCA CCCAAAAGCA CTGGTGAGCC CCTCGGCCAT     300

GTGCCTGCAC GGATGGAGAC CACCCATTCC TTTGGGAACC CCAGCATTTC AGTGTCTACA     360

CAACAGCCAC CCAAAAAGTT TGCCCCGGTA GTTGCTCCAA AACCTAAGTA CAACCCATAC     420

AAACAACCTG GAGGTGAGGG TGATTTTCTT CCACCCCCAC CTCCACCTCT AGATGATTCC     480

AGTGCCCTTC CATCTATCTC TGGAAACTTT CCTCCTCCAC CACCTCTTGA TGAAGAGGCT     540

TTCAAAGTAC AGGGGAATCC CGGAGGCAAG ACACTTGAGG AGAGGCGCTC CAGCCTGGAC     600

GCTGAGATTG ACTCCTTGAC CAGCATCTTG GCTGACCTTG AGTGCAGCTC CCCCTATAAG     660

CCTCGGCCTC CACAGAGCTC CACTGGTTCA ACAGCCTCTC CTCCAGTTTC GACCCCAGTC     720

ACAGGACACA AGAGAATGGT CATCCCGAAC CAACCCCCTC TAACAGCAAC CAAGAAGTCT     780

ACATTGAAAC CACAGCCTGC ACCCCAGGCT GGACCCATCC CTGTGGCTCC AATCGGAACA     840

CTCAAACCCC AGCCTCAGCC AGTCCCAGCC TCCTACACCA CGGCCTCCAC TTCTTCAAGG     900

CCTACCTTTA ATGTGCAGGT GAAGTCAGCC CAGCCCAGCC TCATTATAT GGCTGCCCCT     960

TCATCAGGAC AAATTTATGG CTCAGGGCCC CAGGGCTATA ACACTCAGCC AGTTCCTGTC    1020

TCTGGGCAGT GTCCACCTCC TTCAACACGG GGAGGCATGG ATTATGCCTA CATTCCACCA    1080

CCAGGACTTC AGCCGGAGCC TGGGTATGGG TATGCCCCCA ACCAGGGACG CTATTATGAA    1140

GGCTACTATG CAGCAGGGCC AGGCTATGGG GCAGAAATG ACTCTGACCC TACCTATGGT    1200

CAACAAGGTC ACCCAAATAC CTGGAAACGG GAACCAGGGT ACACTCCTCC TGGAGCAGGG    1260

AACCAGAACC CTCCTGGGAT GTATCCAGTC ACTGGTCCCA AGAAGACCTA TATCACAGAT    1320

CCTGTTTCAG CCCCCTGTGC GCCACCATTG CAGCCAAAGG GTGGCCATTC AGGGCAACTG    1380

GGGCCTTCGT CAGTTGCCCC TTCATTCCGC CCAGAGGATG AGCTTGAGCA CCTGACCAAA    1440

AAGATGCTGT ATGACATGGA AAATCCACCT GCTGACGAAT ACTTTGGCCG CTGTGCTCGC    1500

TGTGGAGAAA ACGTAGTTGG GGAAGGTACA GGATGCACTG CCATGGATCA GGTCTTCCAC    1560

GTGGATTGTT TTACCTGCAT CATCTGCAAC AACAAGCTCC GAGGGCAGCC ATTCTATGCT    1620
```

```
GTGGAAAAGA AAGCATACTG CGAGCCCTGC TACATTAATA CTCTGGAGCA GTGCAATGTG   1680
TGTTCCAAGC CCATCATGGA GCGGATTCTC CGAGCCACCG GGAAGGCCTA TCATCCTCAC   1740
TGTTTCACCT GCGTGATGTG CCACCGCAGC CTGGATGGGA TCCCATTCAC TGTGGATGCT   1800
GGCGGGCTCA TTCACTGCAT TGAGGACTTC CACAAGAAAT TGCCCCGCG GTGTTCTGTG    1860
TGCAAGGAGC CTATTATGCC AGCCCCGGGC CAGGAGGAGA CTGTCCGTAT TGTGGCTTTG   1920
GATCGAGATT TCCATGTTCA CTGCTACCGA TGCGAGGATT GCGGTGGTCT CCTGTCTGAA   1980
GGAGATAACC AAGGCTGCTA CCCCTTGGAT GGGCACATCC TCTGCAAGAC CTGCAACTCT   2040
GCCCGCATCA GGGTGTTGAC CGCCAAGGCG AGCACTGACC TTTAGATTCA GTCACCTGTT   2100
CAGCCGGCAC TGAGAAGAAC GAACACAAGA AAAAGATAAG AAATACTAGA GTAAAGGCCA   2160
TCAAACTACG CGATAGTCTC TGTTCTTCAT CTGCTATTAA CCTTGCCTTA GAAACACATA   2220
AATTATGAGA TTTTTTTTTA AAGTTGTTA CCAAATACAC ATTTCACATT GAATCATGTA    2280
GGATCTTGAT GGGCCTTTGT TCCCAAGGAC TTCCACATTT TGCACAGAT TATGCTCCAT    2340
CCCTTCACTT CTGCATTCCT GTAACTTTTA ATCCCTATGT TTGTCTCACT TTTCATCTGG   2400
TTGAATGGCT TTTCTTAGTG TGGTATTTGC TGTCACATAG TTTTTTCCTG GGTGAGTCTG   2460
CCAACTCACA GGTGCTTTTA GGCTTGAAAT CTCCATCCTA TCATTTCCGT TTTGCCTGTG   2520
ACTGTAAAGA GTAGCCATTC TTTTCCCATG TATTGAAGAG GATATTCTTC TCTTGCTTTA   2580
TACTACTCAC GTCCTTGGGG AGGGAAATGC ACAATTTTTT TTGTTAGGC TGTAAAGAAT    2640
TTAAGCTGTA AATTACATAA GTTAGAACAA GCCCAAATTT AATTTGCAAC CATCAGAATT   2700
CAGAATCTAT AGTGACCAGT GATCAAGGCT AATTGGAAAA GAGTTATCGG CCCATAGCTA   2760
ATAAGTAGTG ACAGACAACC AAGCTTCAAT ATTTTTCTAA AGAAATTACA GGTGGGATAT   2820
GCTAGAAAAG GCATTTGGG GTTATGTTTA AAAAAACATT ATTGTCCCAC AATATTACCT    2880
TAAGATTTTT CTTTTCCGCA CTACCTGAAC ATTGTAATAC AGACAAACTT GATTCTTCT   2940
AGAAGATAAC ATTTTCAATA CTGTCCCACT TCTCATCTTA AAAATATTGT CATGTTTATT   3000
CTAATATCCA ACGCAACTAT CAAAATTGCC TTTTTCTCTA GAGGATGAAG GCTGTGAAAA   3060
AACCGTTCAA ATTCTCTTCT TTTTCTTTTT TATTACCAGG TCCATTTTGC CTGACAATTG   3120
CAAATCAGAG CATACAAAAT AAAACTGTGC AGTTTTGTTT GGTTTACTTT CAAAAGAGTA   3180
GAAAGCTTGA AAAGATTCTG AAACCACAGT TTCATTATTC TCATAATCCT TCTGCAACTG   3240
AAATTACATA TTGCAGGAGA CATTTTCATA TCATCAATCT GACATTTACA CCACACTTTC   3300
AAAGACAATC ACTGAAACAA AAATTGTCTT TATGAGCTAA AAATATGCAG AATCTCTGCC   3360
TAGAATCTTT ATTCAAACTT TTATTAGCCA GTGAAACACT TGCTTGCCAA CTGCCAAGCC   3420
ATACTTATTA AGTTCGAACA TGTTTCACTT AAGGAGAGAC ACCTAGCTTA GTCATGGCAA   3480
GTTGCCATTT TGTAAACTAA GGATTTTGGA CTGAGATTTC TTAAATCTTT CTTCAAATCT   3540
CCCACAAGTA TATACTTTTA AATTATGGAG TATTTAAGT CTACAAAAAG GTATAAATAA    3600
TAATATAATG AATTCCTATA TACCTAATAC CCAGTTTAAG ACACCAAATA TAACAAGTAT   3660
AATTACATCC TCCAATGTAC CGTTTCCTTA TTCCACAGAT ATCTTTTTCA TTATTGTGAA   3720
GTGATGTTCA GATTTCTAGT TTTTTTTTCT AGTTTTTAAT TTAACATCA GAACTGAAAT    3780
AAAAAATTAT GGATACGTGT TTTGAATTGC AAACTATTCC TCAGGAATTC CAATTAAATT   3840
TATTTTACTT GAATAGGAAT GATCATAAAA GTGATTCTTT TTTTGTGACT AGAAATTCTT   3900
AAGCCGATGG TCACTATAGC TCATCCTTAA TGTATGGCTC ATTTGCTTTT GTCACTAAAC   3960
```

```
GGTTTTGTGT TAGAACCACC AAAATTATAG CTTTTAAGAG CTTCCTTTGA CCACTGTCTT    4020

TTTCTTACCC TACTTCTCTT ATCTTTGATC GTATATTTCT CATAATGTGA AATATGATGA    4080

GATTCACTTA GGGGCAGCAT GTTAGTTTTG GGAGGCAATG TCAACTGTGT CTCTGAATTC    4140

CTGTCTTCCA AATTGAAGCC AGACCATGCT GATGACCTCA AGTAGCACTG ACTATTTGAC    4200

AATAGGGCTG ATAATGTAAT CGGCTTGAAT TTTGACTTAG TAACTTTTTA TGTAATACTT    4260

TCGGAGAAAT TCTCTTTAGG ACAAAGCAGA GAGTCCAATT TATTGAGGGA TAGATTGTAT    4320

CTC                                                                  4323
```

(2) INFORMATION FOR SEQ ID NO:163:

(i) SEQUENCE CHARACTERISTICS:
        (A) LENGTH: 612 amino acids
        (B) TYPE: amino acid
        (C) STRANDEDNESS: single
        (D) TOPOLOGY: linear (xi) SEQUENCE DESCRIPTION: SEQ ID NO:163:

```
Met Ser His Pro Ser Trp Leu Pro Pro Lys Ser Thr Gly Glu Pro Leu
 1               5                  10                  15

Gly His Val Pro Ala Arg Met Glu Thr Thr His Ser Phe Gly Asn Pro
                20                  25                  30

Ser Ile Ser Val Ser Thr Gln Gln Pro Pro Lys Lys Phe Ala Pro Val
            35                  40                  45

Val Ala Pro Lys Pro Lys Tyr Asn Pro Tyr Lys Gln Pro Gly Gly Glu
50                  55                  60

Gly Asp Phe Leu Pro Pro Pro Pro Pro Leu Asp Asp Ser Ser Ala
65                  70                  75                  80

Leu Pro Ser Ile Ser Gly Asn Phe Pro Pro Pro Pro Leu Asp Glu
                85                  90                  95

Glu Ala Phe Lys Val Gln Gly Asn Pro Gly Lys Thr Leu Glu Glu
            100                 105                 110

Arg Arg Ser Ser Leu Asp Ala Glu Ile Asp Ser Leu Thr Ser Ile Leu
        115                 120                 125

Ala Asp Leu Glu Cys Ser Ser Pro Tyr Lys Pro Arg Pro Pro Gln Ser
130                 135                 140

Ser Thr Gly Ser Thr Ala Ser Pro Val Ser Thr Pro Val Thr Gly
145                 150                 155                 160

His Lys Arg Met Val Ile Pro Asn Gln Pro Pro Leu Thr Ala Thr Lys
                165                 170                 175

Lys Ser Thr Leu Lys Pro Gln Pro Ala Pro Gln Ala Gly Pro Ile Pro
            180                 185                 190

Val Ala Pro Ile Gly Thr Leu Lys Pro Gln Pro Gln Pro Val Pro Ala
        195                 200                 205

Ser Tyr Thr Thr Ala Ser Thr Ser Ser Arg Pro Thr Phe Asn Val Gln
210                 215                 220

Val Lys Ser Ala Gln Pro Ser Pro His Tyr Met Ala Ala Pro Ser Ser
225                 230                 235                 240

Gly Gln Ile Tyr Gly Ser Gly Pro Gln Gly Tyr Asn Thr Gln Pro Val
                245                 250                 255

Pro Val Ser Gly Gln Cys Pro Pro Ser Thr Arg Gly Gly Met Asp
            260                 265                 270

Tyr Ala Tyr Ile Pro Pro Pro Gly Leu Gln Pro Glu Pro Gly Tyr Gly
        275                 280                 285
```

```
Tyr Ala Pro Asn Gln Gly Arg Tyr Tyr Glu Gly Tyr Tyr Ala Ala Gly
        290                 295                 300

Pro Gly Tyr Gly Gly Arg Asn Asp Ser Asp Pro Thr Tyr Gly Gln Gln
305                 310                 315                 320

Gly His Pro Asn Thr Trp Lys Arg Glu Pro Gly Tyr Thr Pro Pro Gly
                325                 330                 335

Ala Gly Asn Gln Asn Pro Pro Gly Met Tyr Pro Val Thr Gly Pro Lys
                340                 345                 350

Lys Thr Tyr Thr Thr Asp Pro Val Ser Ala Pro Cys Ala Pro Pro Leu
            355                 360                 365

Gln Pro Lys Gly Gly His Ser Gly Gln Leu Gly Pro Ser Ser Val Ala
    370                 375                 380

Pro Ser Phe Arg Pro Glu Asp Leu Glu His Leu Thr Lys Lys Met
385                 390                 395                 400

Leu Tyr Asp Met Glu Asn Pro Pro Ala Asp Glu Tyr Phe Gly Arg Cys
                405                 410                 415

Ala Arg Cys Gly Glu Asn Val Val Gly Glu Gly Thr Gly Cys Thr Ala
            420                 425                 430

Met Asp Gln Val Phe His Val Asp Cys Phe Thr Cys Ile Ile Cys Asn
        435                 440                 445

Asn Lys Leu Arg Gly Gln Pro Phe Tyr Ala Val Glu Lys Lys Ala Tyr
    450                 455                 460

Cys Glu Pro Cys Tyr Ile Asn Thr Leu Glu Gln Cys Asn Val Cys Ser
465                 470                 475                 480

Lys Pro Ile Met Glu Arg Ile Leu Arg Ala Thr Gly Lys Ala Tyr His
                485                 490                 495

Pro His Cys Phe Thr Cys Val Met Cys His Arg Ser Leu Asp Gly Ile
                500                 505                 510

Pro Phe Thr Val Asp Ala Gly Gly Leu Ile His Cys Ile Glu Asp Phe
        515                 520                 525

Glu Lys Lys Phe Ala Pro Arg Cys Ser Val Cys Lys Glu Pro Ile Met
    530                 535                 540

Pro Ala Pro Gly Gln Glu Glu Thr Val Arg Ile Val Ala Leu Asp Arg
545                 550                 555                 560

Asp Phe His Val His Cys Tyr Arg Cys Glu Asp Cys Gly Gly Leu Leu
                565                 570                 575

Ser Glu Gly Asp Asn Gln Gly Cys Tyr Pro Leu Asp Gly His Ile Leu
                580                 585                 590

Cys Lys Thr Cys Asn Ser Ala Arg Ile Arg Val Leu Thr Ala Lys Ala
            595                 600                 605

Ser Thr Asp Leu
    610

(2) INFORMATION FOR SEQ ID NO:164:

(i) SEQUENCE CHARACTERISTICS:
        (A) LENGTH: 4067 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:164:

CTTGAATCTT GGGGCAGGAA CTCAGAAAAC TTCCAGCCCG GGCAGCCCGC GTTTGGTGCA     60

AGACTCAGGA GCTAGCAGCC CGTCCCCCTC CGACTCTCCG GTGCCGTTGC TGCCTGCTCC    120
```

-continued

```
CGCCACCCTA GGAGGCGCGG TGCCACCCAC TACTCTGTCC TCTGCCTGTG CTCCGTGCCC    180
GACCCTATCC CGGCGGAGTC TCCCCATCCT CCTTTGCTTT CCGACTGCCC AAGGCACTTT    240
CAATCTCAAT CTCTTCTCTC TCTCTCTCTC TCTCTCTGTC TCTCTCTCTC TCTCTCTCTC    300
TCTCTCTCTC GCAGGGTGGG GGGAAGAGGA GGAGGAATTC TTTCCCCGCC TAACATTTCA    360
AGGGACCACA ATCACTCCAA GTCTCTTCCC TTTCCAAGCC GCTTCCGAAG TGCTCCCGGT    420
GCCCGCAACT CCTGATCCCA ACCCGCGAGA GGAGCCTCTG CGACCTCAAA GCCTCTCTTC    480
CTTCTCCCTC GCTTCCCTCC TCCTCTTGCT ACCTCCACCT CCACCGCCAC CTCCACCTCC    540
GGCACCCACC CACCGCCGCC GCCGCCACCG GCAGCGCCCTC CTCCTCTCCT CCTCCTCCTC    600
CCCTCTTCTC TTTTTGGCAG CCGCTGGACG TCCGGTGTTG ATGGTGGCAG CGGCGGCAGC    660
CTAAGCAACA GCAGCCCTCG CAGCCCGCCA GCTCGCGCTC GCCCCGCCGG CGTCCCCAGC    720
CCTATCACCT CATCTCCCGA AAGGTGCTGG GCAGCTCCGG GGCGGTCGAG GCGAAGCGGC    780
TGCAGCGGCG GTAGCGGCGG CGGGAGGCAG GATGAGCGCA CGCGGTGAGG GCGCGGGGCA    840
GCCGTCCACT TCAGCCCAGG GACAACCTGC CGCCCCAGCG CCTCAGAAGA GAGGACGCGG    900
CCGCCCCAGG AAGCAGCAGC AAGAACCAAC CGGTGAGCCC TCTCCTAAGA GACCCAGGGG    960
AAGACCCAAA GGCAGCAAAA ACAAGAGTCC CTCTAAAGCA GCTCAAAAGA AAGCAGAAGC   1020
CACTGGAGAA AAACGGCCAA GAGGCAGACC TAGGAAATGG CCACAACAAG TTGTTCAGAA   1080
GAAGCCTGCT CAGGAGGAAA CTGAAGAGAC ATCCTCACAA GAGTCTGCCG AAGAGGACTA   1140
GGGGGCGCAA CGTTCGATTT CTACCTCAGC AGCAGTTGGA TCTTTTGAAG GGAGAAGACA   1200
CTGCAGTGAC CACTTATTCT GTATTGCCAT GGTCTTTCCA CTTTCATCTG GGGTGGGGTG   1260
GGGTGGGGTG GGGGAGGGGG GGGTGGGGTG GGGAGAAATC ACATAACCTT AAAAAGGACT   1320
ATATTAATCA CCTTCTTTGT AATCCCTTCA CAGTCCCAGG TTTAGTGAAA AACTGCTGTA   1380
AACACAGGGG ACACAGCTTA ACAATGCAAC TTTTAATTAC TGTTTTCTTT TTTCTTAACC   1440
TACTAATAGT TTGTTGATCT GATAAGCAAG AGTGGGCGGG TGAGAAAAAC CGAATTGGGT   1500
TTAGTCAATC ACTGCACTGC ATGCAAACAA GAAACGTGTC ACACTTGTGA CGTCGGGCAT   1560
TCATATAGGA AGAACGCGGT GTGTAACACT GTGTACACCT CAAATACCAC CCCAACCCAC   1620
TCCCTGTAGT GAATCCTCTG TTTAGAACAC CAAAGATAAG GACTAGATAC TACTTTCTCT   1680
TTTTCGTATA ATCTTGTAGA CACTTACTTG ATGATTTTTA ACTTTTTATT TCTAAATGAG   1740
ACGAAATGCT GATGTATCCT TTCATTCAGC TAACAAACTA GAAAAGGTTA TGTTCATTTT   1800
TCAAAAGGG AAGTAAGCAA ACAAATATTG CCAACTCTTC TATTTATGGA TATCACACAT   1860
ATCAGCAGGA GTAATAAATT TACTCACAGC ACTTGTTTTC AGGACAACAC TTCATTTTCA   1920
GGAAATCTAC TTCCTACAGA GCCAAAATGC CATTTAGCAA TAAATAACAC TTGTCAGCCT   1980
CAGAGCATTT AAGGAAACTA GACAAGTAAA ATTATCCTCT TTGTAATTTA ATGAAAAGGT   2040
ACAACAGAAT AATGCATGAT GAACTCACCT AATTATGAGG TGGGAGGAGC GAAATCTAAA   2100
TTTCTTTTGC TATAGTTATA CATCAATTTA AAAAGCAAAA AAAAAAAGGG GGGGCAATC    2160
TCTCTCTGTG TCTTTCTCTC TCTCTCTCCC TCTCCCTCTC TCTTTTCATG TGTATCAGTT   2220
TCCATGAAAG ACCTGAATAC CACTTACCTC AAATTAAGCA TATGTGTTAC TTCAAGTAAT   2280
ACGTTTTGAC ATAAGATGGT TGACCAAGGT GCTTTTCTTC GGCTTGAGTT CACCATCTCT   2340
TCATTCAAAC TGCACTTTTA GCCAGAGATG CAATATATCC CCACTACTCA ATACTACCTC   2400
TGAATGTTAC AACGAATTTA CAGTCTAGTA CTTATTACAT GCTGCTATAC ACAAGCAATG   2460
```

-continued

```
CAAGAAAAAA ACTTACTGGG TAGGTGATTC TAATCATCTG CAGTTCTTTT TGTACACTTA    2520
ATTACAGTTA AAGAAGCAAT CTCCTTACTG TGTTTCAGCA TGACTATGTA TTTTTCTATG    2580
TTTTTTTAAT TAAAAATTTT TAAAATACTT GTTTCAGCTT CTCTGCTAGA TTTCTACATT    2640
AACTTGAAAA TTTTTTAACC AAGTCGCTCC TAGGTTCTTA AGGATAATTT TCCTCAATCA    2700
CACTACACAT CACACAAGAT TTGACTGTAA TATTTAAATA TTACCCTCCA AGTCTGTACC    2760
TCAAATGAAT TCTTTAAGGA GATGGACTAA TTGACTTGCA AAGACCTACC TCCAGACTTC    2820
AAAAGGAATG AACTTGTTAC TTGCAGCATT CATTTGTTTT TTCAATGTTT GAAATAGTTC    2880
AAACTGCAGC TAACCCTAGT CAAAACTATT TTTGTAAAAG ACATTTGATA GAAAGGAACA    2940
CGTTTTTACA TACTTTTGCA AAATAAGTAA ATAATAAATA AAATAAAGCC AACCTTCAAA    3000
GAACTTGAAG CTTTGTAGGT GAGATGCAAC AAGCCCTGCT TTTGCATAAT GCAATCAAAA    3060
ATATGTGTTT TTAAGATTAG TTGAATATAA GAAAATGCTT GACAAATATT TTCATGTATT    3120
TTACACAAAT GTGATTTTTG TAATATGTCT CAACCAGATT TATTTTAAAC GCTTCTTATG    3180
TAGAGTTTTT ATGCCTTTCT CTCCTAGTGA GTGTGCTGAC TTTTTAACAT GGTATTATCA    3240
ACTGGGCCAG GAGGTAGTTT CTCATGACGG CTTTTGTCAG TATGGCTTTT AGTACTGAAG    3300
CCAAATGAAA CTCAAAACCA TCTCTCTTCC AGCTGCTTCA GGGAGGTAGT TTCAAAGGCC    3360
ACATACCTCT CTGAGACTGG CAGATCGCTC ACTGTTGTGA ATCACCAAAG GAGCTATGGA    3420
GAGAATTAAA ACTCAACATT ACTGTTAACT GTGCGTTAAA TAAGCAAATA AACAGTGGCT    3480
CATAAAAATA AAAGTCGCAT TCCATATCTT TGGATGGGCC TTTTAGAAAC CTCATTGGCC    3540
AGCTCATAAA ATGGAAGCAA TTGCTCATGT TGGCCAAACA TGGTGCACCG AGTGATTTCC    3600
ATCTCTGGTA AAGTTACACT TTTATTTCCT GTATGTTGTA CAATCAAAAC ACACTACTAC    3660
CTCTTAAGTC CCAGTATACC TCATTTTTCA TACTGAAAAA AAAAGCTTGT GGCCAATGGA    3720
ACAGTAAGAA CATCATAAAA TTTTTATATA TATAGTTTAT TTTTGTGGGA GATAAATTTT    3780
ATAGGACTGT TCTTTGCTGT TGTTGGTCGC AGCTACATAA GACTGGACAT TTAACTTTTC    3840
TACCATTTCT GCAAGTTAGG TATGTTTGCA GGAGAAAAGT ATCAAGACGT TTAACTGCAG    3900
TTGACTTTCT CCCTGTTCCT TTGAGTGTCT TCTAACTTTA TTCTTTGTTC TTTATGTAGA    3960
ATTGCTGTCT ATGATTGTAC TTTGAATCGC TTGCTTGTTG AAAATATTTC TCTAGTGTAT    4020
TATCACTGTC TGTTCTGCAC AATAAACATA ACAGCCTCTG TGATCCC                 4067
```